United States Patent
Kiessling et al.

(10) Patent No.: US 10,413,588 B2
(45) Date of Patent: Sep. 17, 2019

(54) PROBIOTIC FUNCTION OF HUMAN INTELECTIN

(71) Applicant: Wisconsin Alumni Research Foundation, Madison, WI (US)

(72) Inventors: Laura L. Kiessling, Madison, WI (US); Darryl A. Wesener, Saint Louis, MO (US); Federico Rey, Madison, WI (US); Kittikhun Wangkanont, Bangkok (TH)

(73) Assignee: Wisconsin Alumni Research Foundation, Madison, WI (US)

( * ) Notice: Subject to any disclaimer, the term of this patent is extended or adjusted under 35 U.S.C. 154(b) by 137 days.

(21) Appl. No.: 15/342,360

(22) Filed: Nov. 3, 2016

(65) Prior Publication Data

US 2017/0136088 A1    May 18, 2017

Related U.S. Application Data

(60) Provisional application No. 62/251,453, filed on Nov. 5, 2015.

(51) Int. Cl.

| | |
|---|---|
| *A23L 33/17* | (2016.01) |
| *A61K 38/17* | (2006.01) |
| *A61K 47/60* | (2017.01) |
| *A23L 33/135* | (2016.01) |
| *A61K 35/745* | (2015.01) |
| *A61K 35/747* | (2015.01) |
| *G01N 33/569* | (2006.01) |

(52) U.S. Cl.
CPC ........ *A61K 38/1732* (2013.01); *A23L 33/135* (2016.08); *A23L 33/17* (2016.08); *A61K 35/745* (2013.01); *A61K 35/747* (2013.01); *A61K 47/60* (2017.08); *G01N 33/56911* (2013.01); *G01N 2333/4724* (2013.01)

(58) Field of Classification Search
None
See application file for complete search history.

(56) References Cited

U.S. PATENT DOCUMENTS

| | | | | |
|---|---|---|---|---|
| 2002/0192201 | A1* | 12/2002 | Shafran ................. | A61K 31/415 424/93.43 |
| 2003/0082533 | A1* | 5/2003 | Yue ..................... | C07K 14/4726 435/6.12 |
| 2016/0131649 | A1* | 5/2016 | Kiessling ......... | G01N 33/56911 514/3.1 |

OTHER PUBLICATIONS

Tomassoni, Daniele et al. Effects of in vitro altered microflora on immunolocalization of ladderlectin and intelectin in trout intestine. Italian Journal of Anatomy and Embryology, [S.I.], p. 190, Feb. 2013. ISSN 2038-5129. (Year: 2013).*
Chen et al., "A zebrafish intelectin ortholog agglutinates both Gram-negative and Gram-positive bacteria with binding capacity to bacterial polysaccharide," *Fish Shellfish Immunol.*, 55:729-736, 2016.
Garlatti et al. "Structural insights into the innate immune recognition specificities of L- and H-ficolins," *EMBO J.*, 26:623-633, 2007.
Gerwick et al., "Gene transcript changes in individual rainbow trout livers following an inflammatory stimulus," *Fish Shellfish Immunol.*, 22(3):157-171, 2007.
Hempel et al., "Probiotics for the Prevention and Treatment of Antibiotic-Associated Diarrhea: A Systematic Review and Meta-analysis," *JAMA*, 307(18):1959-1969, 2012.
Hiramatsu-Ito et al., "Omentin attenuates atherosclerotic lesion formation in apolipoprotein E-deficient mice," *Cardiovasc. Res.*, 110:107-117, 2016.
Lee et al., "Human homologs of the Xenopus oocyte cortical granule lectin XL35," *Glycobiology*, 11(1):65-73, 2001.
Lin et al., "Characterization and comparative analyses of zebrafish intelectins: highly conserved sequences, diversified structures and functions," *Fish Shellfish Immunol.*, 26(3):396-405, 2009.
Peatman et al., "Expression analysis of the acute phase response in channel catfish (*Ictalurus punctatus*) after infection with a Gram-negative bacterium," *Develop. Compar. Immunol.*, 31(11):1183-1196, 2007.
Tsuji et al., "Human Intelectin is a Novel Soluble Lectin that Recognizes Galactofuranose in Carbohydrate Chains of Bacterial Cell Wall," *J. Biol. Chem.*, 276:23456-23463, 2001.
Wangkanont et al., "Structures of Xenopus Embryonic Epidermal Lectin Reveal a Conserved Mechanism of Microbial Glycan Recognition," *J. Biol. Chem.*, 291(11):5596-5610, 2016.
Watanabe et al., "Counteractive effects of omentin-1 against atherogenesis," *Cardiovasc. Res.*, 110:118-128, 2016.
Wesener et al., "Recognition of microbial glycans by human intelectin-1," *Nat. Struct. Mol. Biol.*, 22(8):603-610, 2015.

* cited by examiner

*Primary Examiner* — Blaine Lankford
(74) *Attorney, Agent, or Firm* — Parker Highlander PLLC

(57) ABSTRACT

The present disclosure provides for methods providing a pre/probiotic agent to a subject. Human Intelectin 1 (hIntL-1) has been shown to bind selectively to glycan components on bacteria, thereby promoting and protecting the microbiome.

9 Claims, 28 Drawing Sheets
Specification includes a Sequence Listing.

Figure 5A:
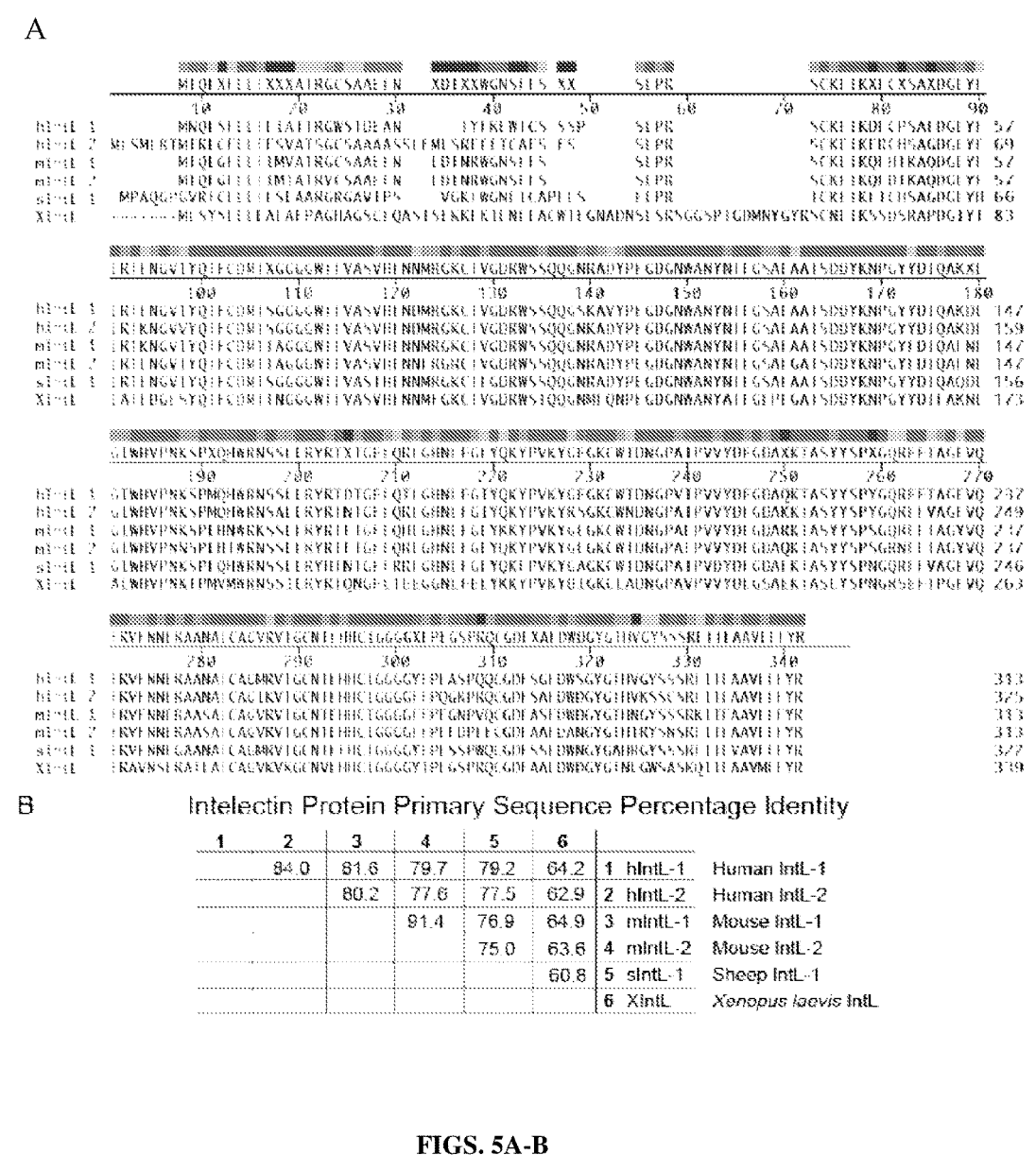

[Sequence alignment of intelectin proteins with conserved regions highlighted, showing hIntL-1, hIntL-2, mIntL-1, mIntL-2, sIntL-1, and XIntL aligned across positions 1-340, with final residue counts of 313, 325, 313, 313, 327, and 339 respectively.]

B

Intelectin Protein Primary Sequence Percentage Identity

| 1 | 2 | 3 | 4 | 5 | 6 | | |
|---|---|---|---|---|---|---|---|
| | 84.0 | 81.6 | 79.7 | 79.2 | 64.2 | 1 hIntL-1 | Human IntL-1 |
| | | 80.2 | 77.6 | 77.5 | 62.9 | 2 hIntL-2 | Human IntL-2 |
| | | | 91.4 | 76.9 | 64.9 | 3 mIntL-1 | Mouse IntL-1 |
| | | | | 75.0 | 63.6 | 4 mIntL-2 | Mouse IntL-2 |
| | | | | | 60.8 | 5 sIntL-1 | Sheep IntL-1 |
| | | | | | | 6 XIntL | *Xenopus laevis* IntL |

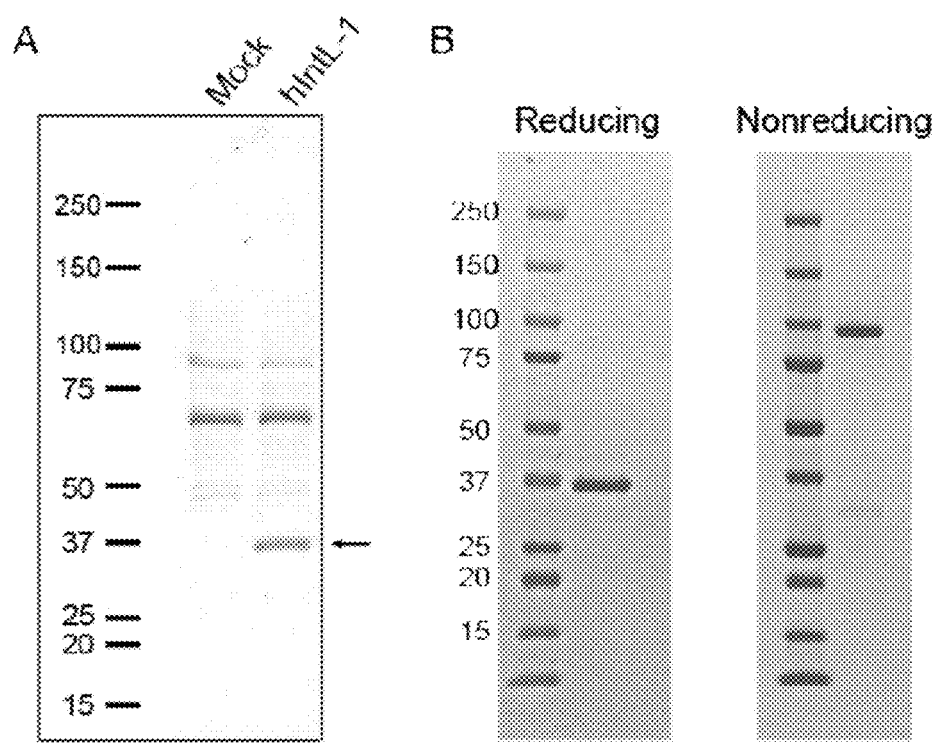
FIGS. 7A-B

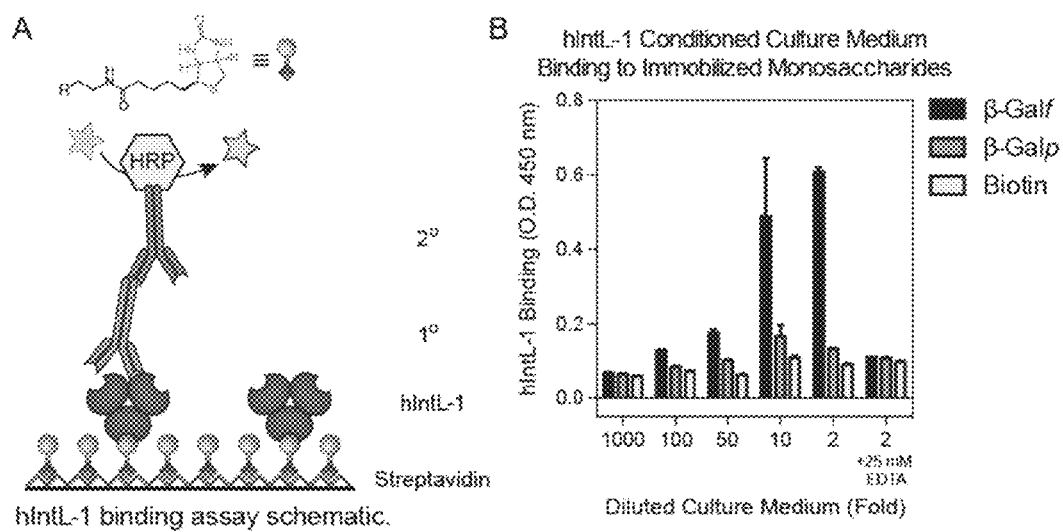
FIGS. 8A-B

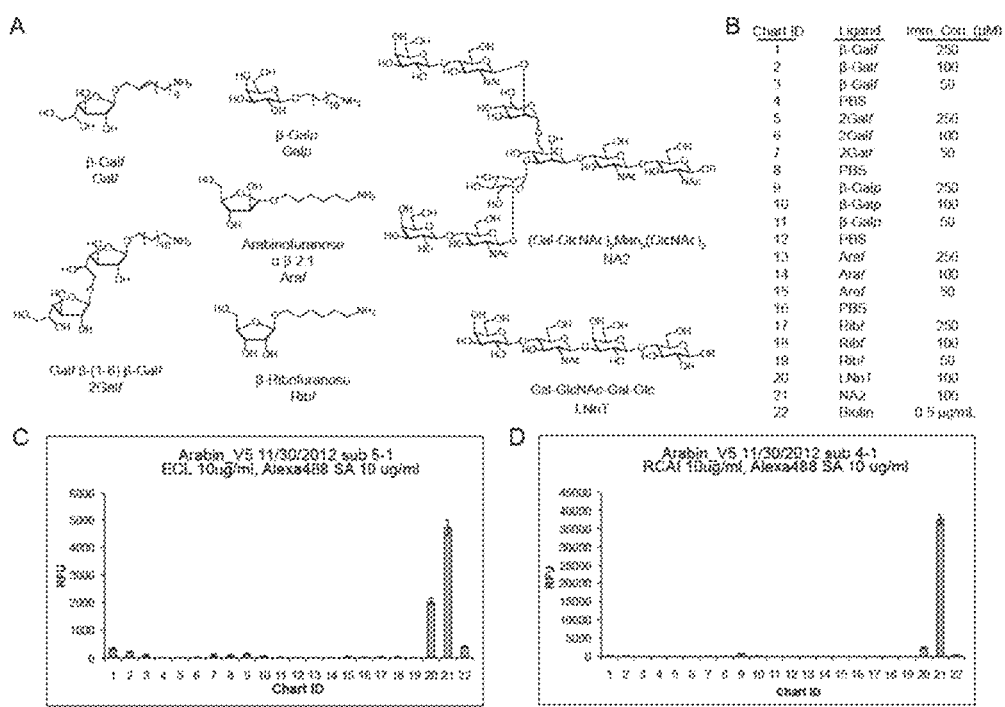
FIGS. 10A-D

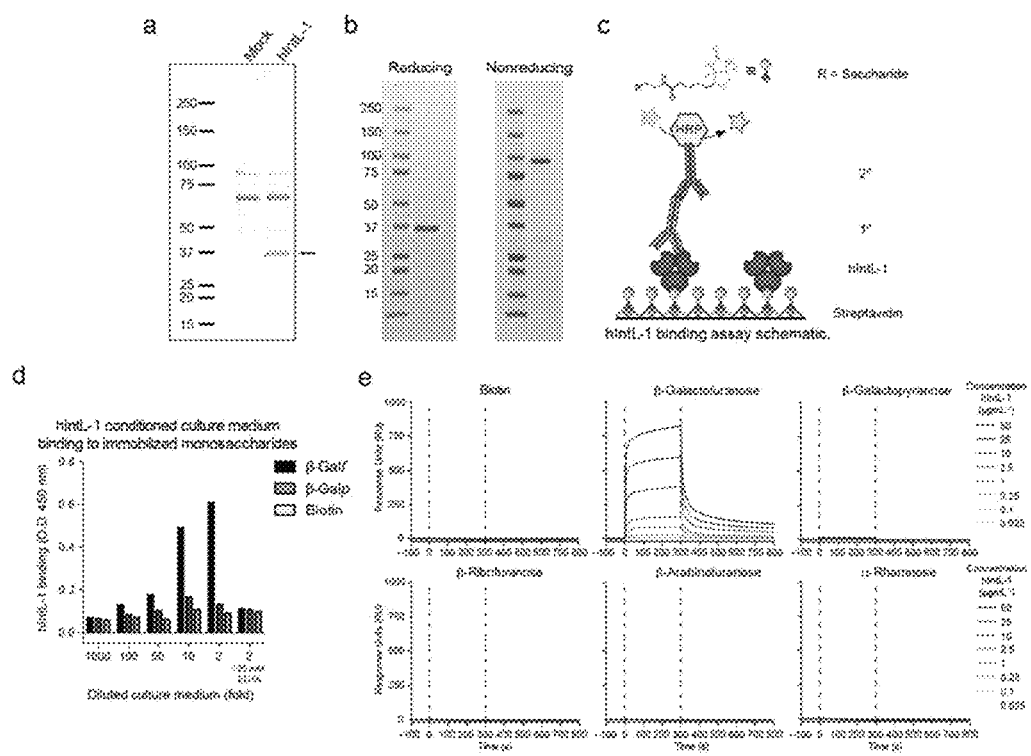
FIGS. 11A-E

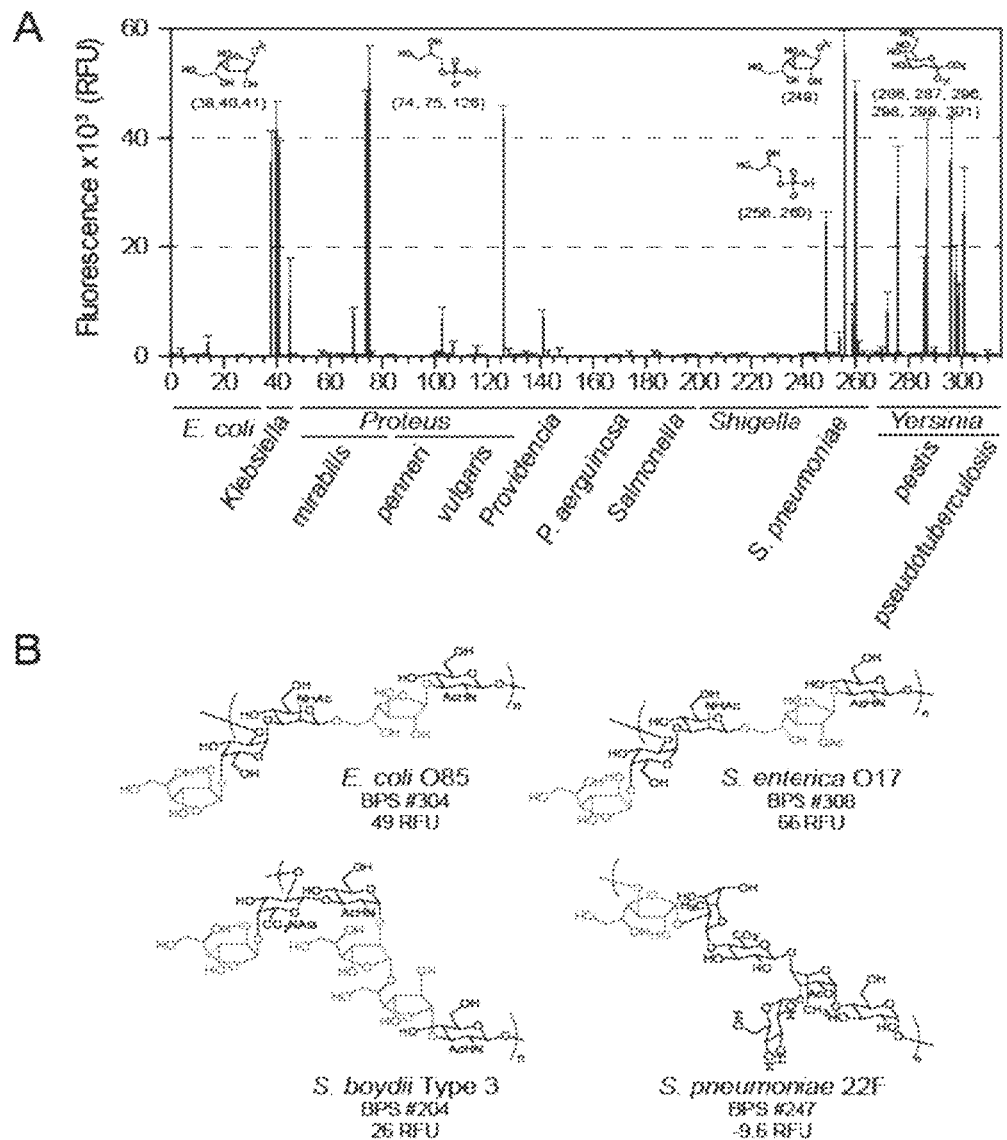
FIGS. 12A-B

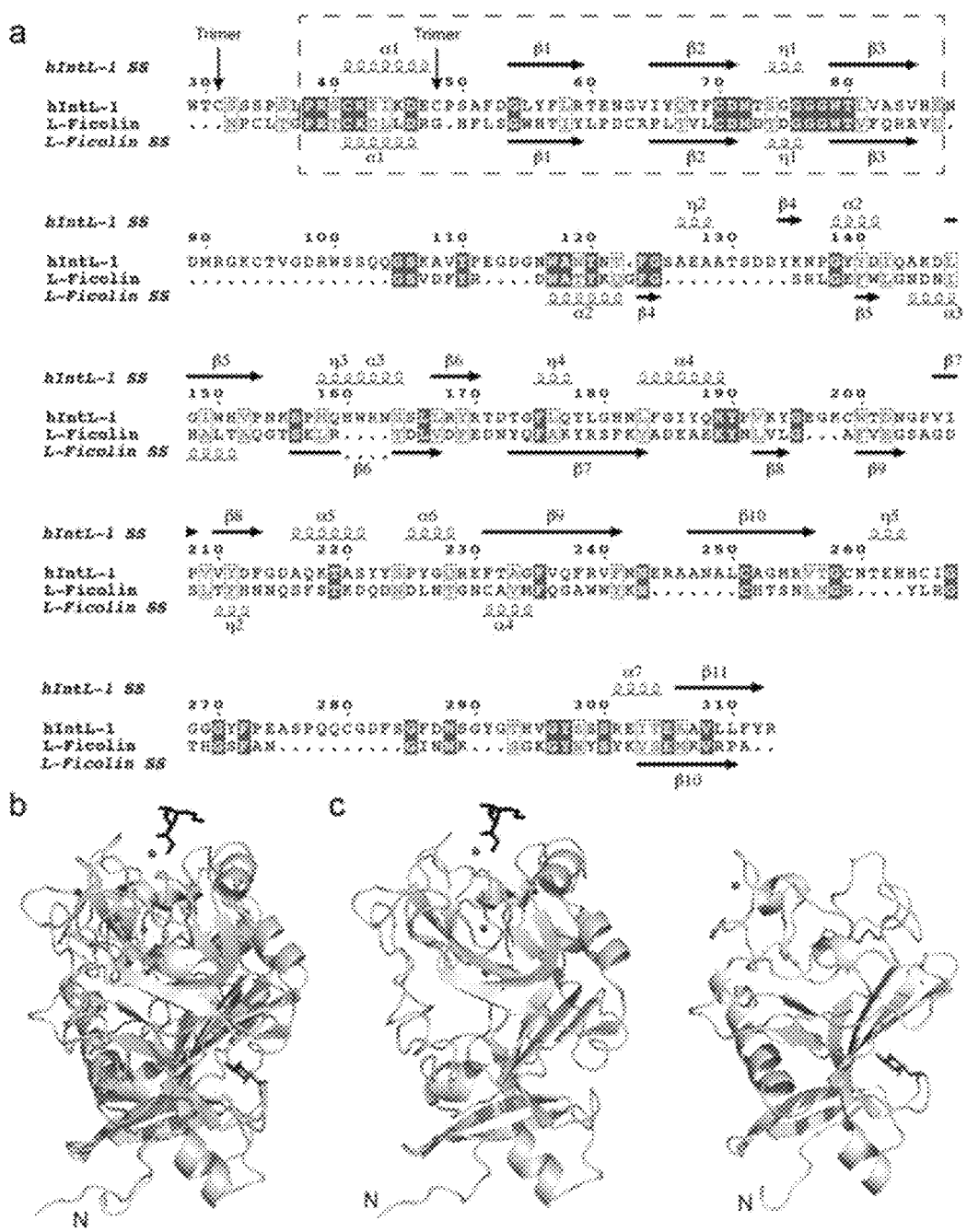
FIGS. 13A-C

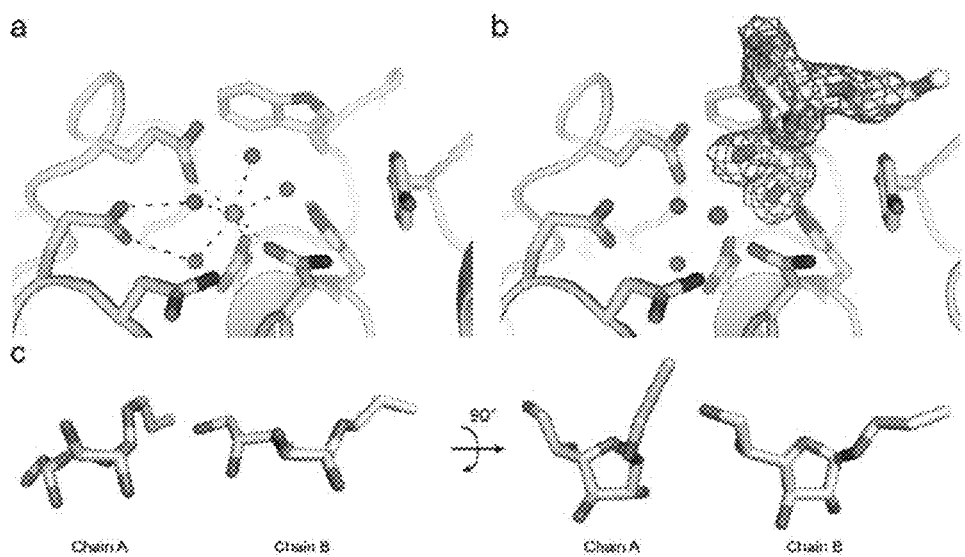
FIG. 14A-D

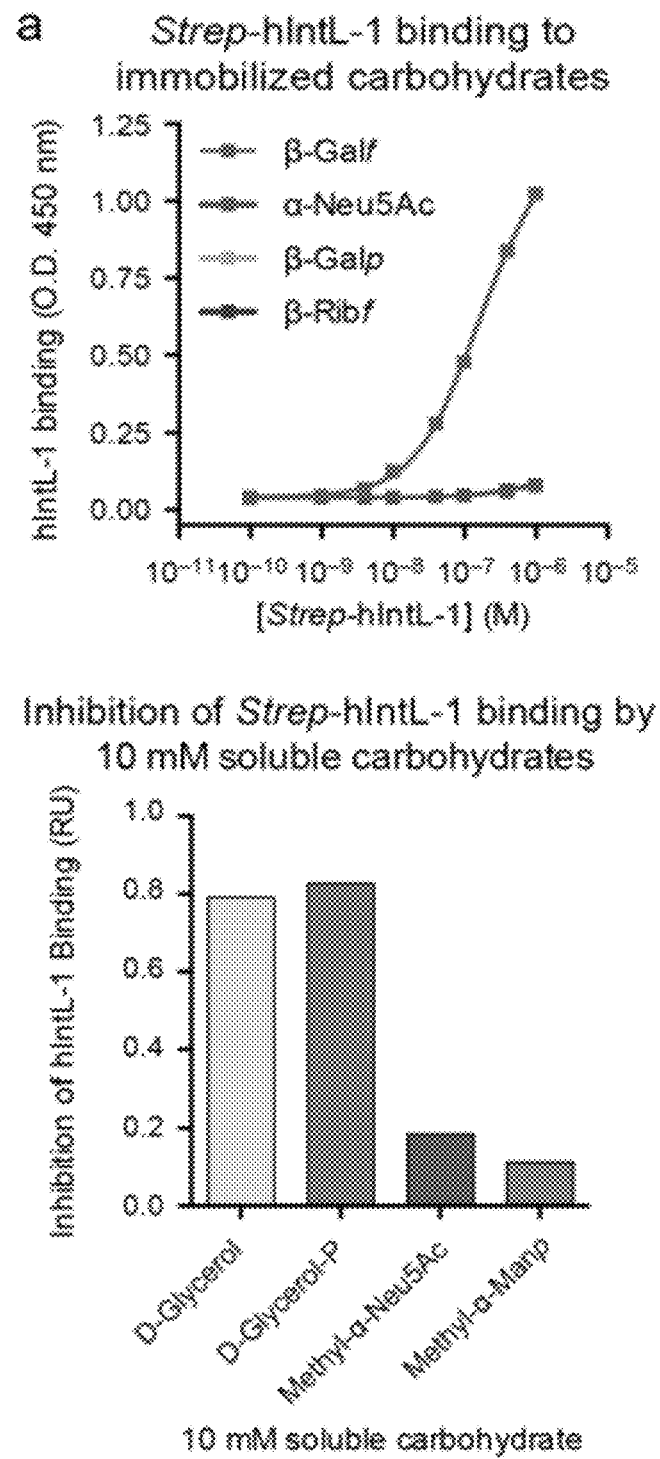
FIG. 15A-B

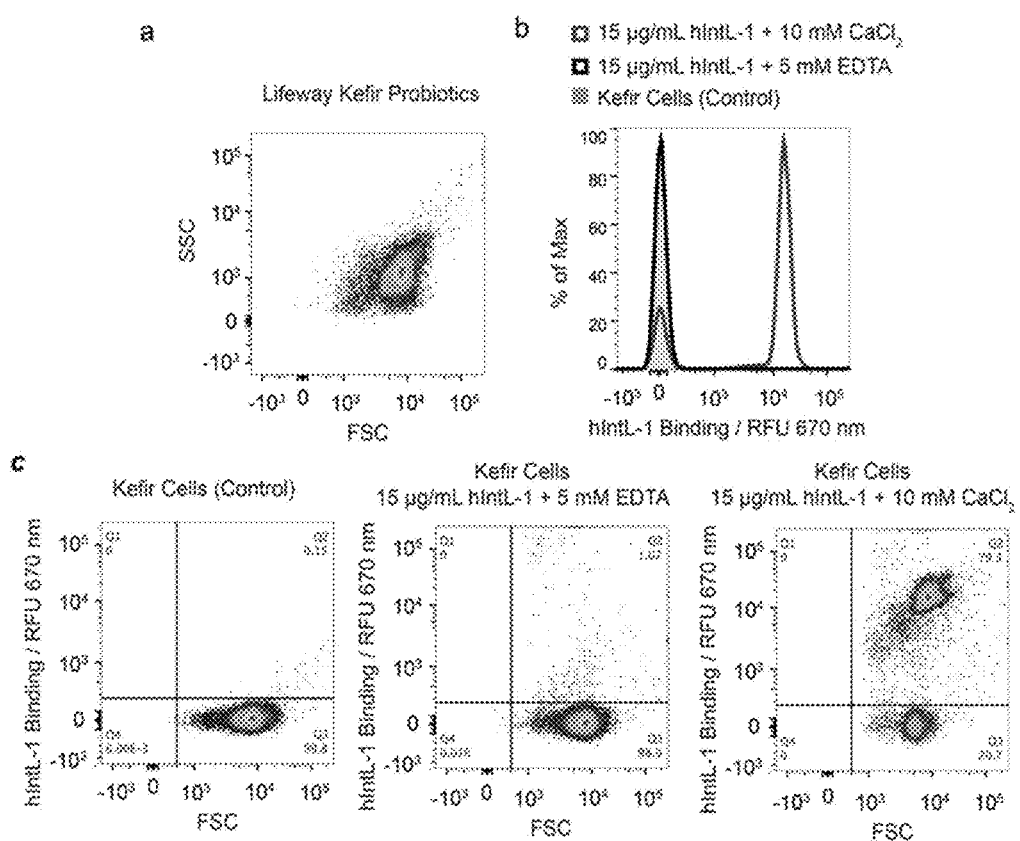
FIGS. 18A-C

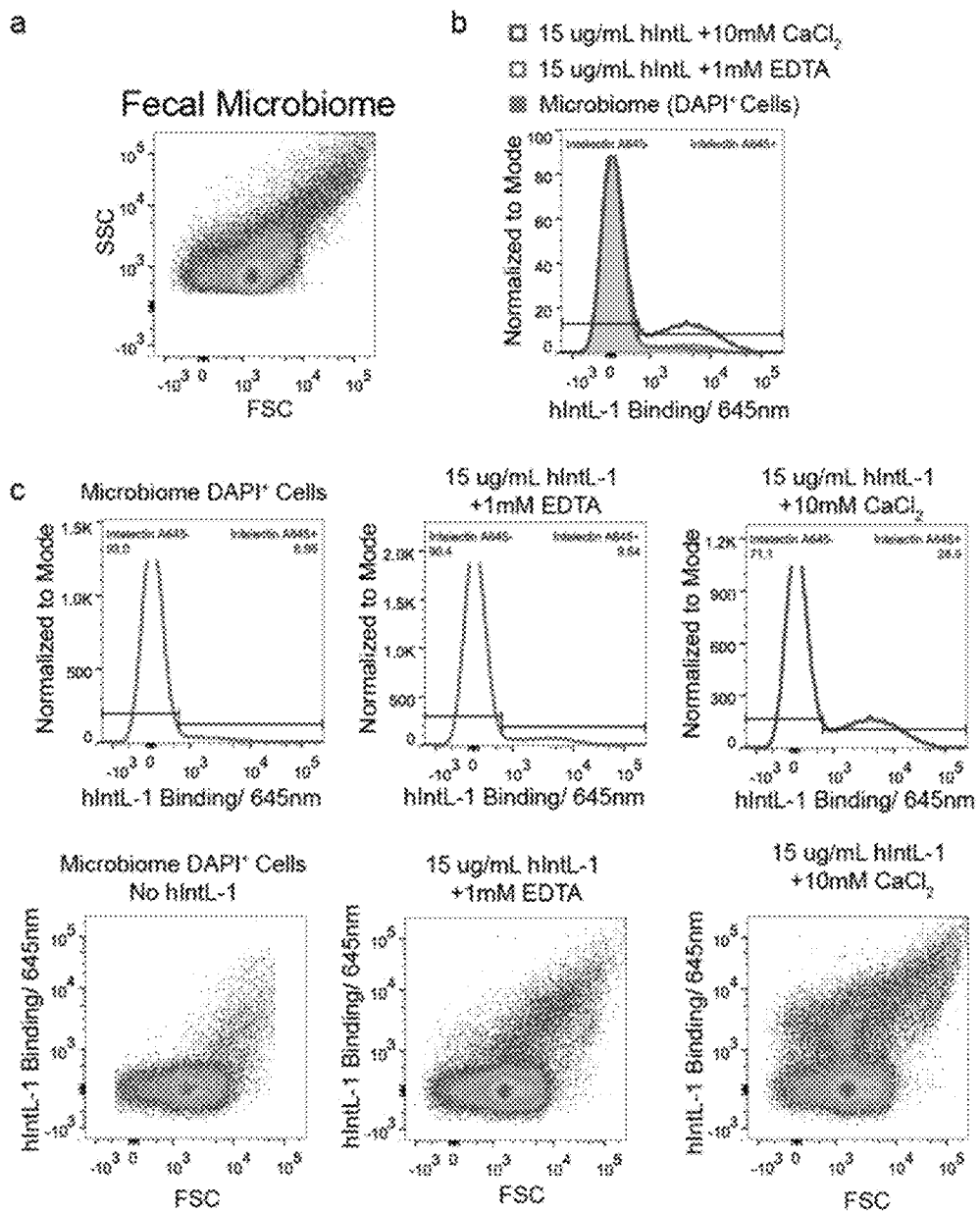
FIGS. 19A-C

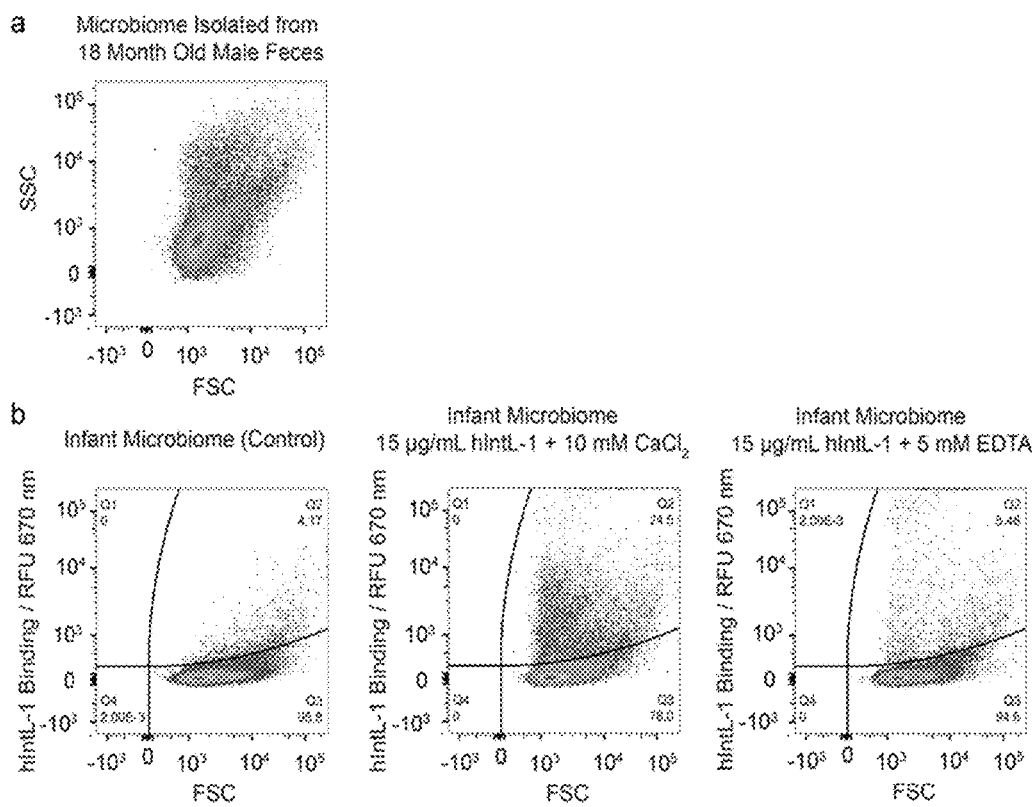
FIGS. 20A-B

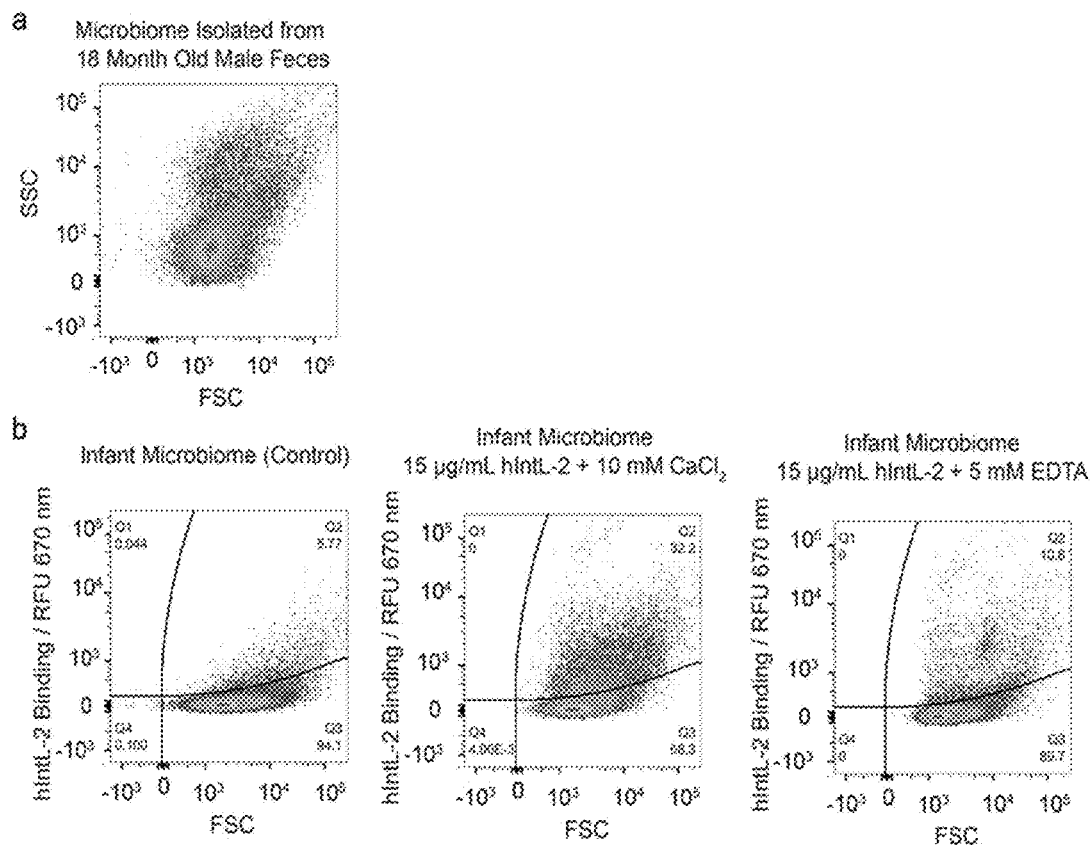
FIGS. 21A-B

PROBIOTIC FUNCTION OF HUMAN INTELECTIN

This application claims benefit of priority to U.S. Provisional Application Ser. No. 62/251,453, filed Nov. 5, 2015, the entire contents of which are hereby incorporated by reference.

This invention was made with government support under AI063596 awarded by the National Institutes of Health. The government has certain rights in the invention.

BACKGROUND

1. Field

The present disclosure relates generally to the fields of biology and medicine. More particularly, it concerns molecular interactions between human intelectins and microbial glycans. Specifically, the disclosure relates to the use of intelectins to promote and protect the human microbiome.

2. Description of Related Art

The human body is an ecological niche populated by an estimated $10^{14}$ microbial cells. The human gastrointestinal (GI) tract, often referred to as the intestinal microbiome, is thought to contain between 500 and 1,000 different species of bacteria. These resident bacteria are thought to play an important role in human health and disease. Specifically, the intestinal microbiome has been linked to infant immunity, obesity, diabetes, cardiovascular health, Crohn's disease, and irritable bowel disease (IBS). Methods to regulate the composition and population of these bacteria are being sought because of their potential to improve human health.

The manipulation of the intestinal microbiome can have benefits, as has been observed in studies documenting the positive effects of fecal transplants for treatment of *Clostridium difficile* infection. Fecal transplants are also being evaluated for treatment of other diseases, including colitis and IBS. While fecal transplants are a dramatic means of manipulating the composition of the microbiome, augmentation and supplementation of the intestinal microbiome with specific bacterial species has been suggested to produce overall health benefits. Specifically, "probiotics"—mixtures of intact and/or alive organisms that are thought to augment an individual's microbiome—are often suggested as supplements when individuals are prescribed strong antibiotics. The available data (Hempel et al., 1959) suggest that these agents can mitigate the effects of antibiotic associate diarrhea and other conditions. These data have fueled interest in using probiotics to promote human health, and there remains a need to provide improved probiotic formulations with advantageous properties.

SUMMARY

Thus, in accordance with the present disclosure, there is provided a method a method of promoting the growth and/or stability of a microbiome in a subject comprising administering to the subject an intelectin molecule. The intelectin molecule may be administered in probiotic formulation containing one or more beneficial microorganisms, such as microorganisms from the genus *Lactobacillus* or *Bifidobacterium*, or a species selected from the group consisting of the bacteria set forth in Table 1. The intelectin may bind to a β-linked D-galactofuranose, a glycan containing a heptose, D-glycero-D-talo-oct-2-ulosonic acid (KO) and/or 3-deoxy-D-manno-oct-2-ulosonic acid (KDO) residue, and/or a saccharide residue modified with a phospho-glycerol (Gro-P) substituent. The intelectin may be hIntL-1 or hIntL-2, and the subject is a human. The intelectin may be a non-human intelectin, and the subject is a non-human mammal of the same species as the intelectin, such as where the intelectin is mouse intelectin-1, and the subject is a mouse, or where the intelectin is a fish intelectin, and the subject is a fish. The intelectin may be PEGylated. The intelectin may be administered orally, rectally, vaginally, topically or via inhalation. The subject may suffer from one or more of lactose intolerance, antibiotic-induced diarrhea, eczema, *Heliobacter pylori* infection, irritable bowel syndrome, colitis, necrotizing enterocolitis, bacterial vaginosis, inflammation, high blood pressure, elevated cholesterol, atherosclerosis, obesity, Crohn's Disease, an allergy, asthma, cancer (e.g., colorectal cancer) and/or vitamin deficiency.

Also provided is a formulation comprising an intelectin molecule and one or more beneficial microorganisms. The intelectin may bind to a β-linked D-galactofuranose, a glycan containing a heptose, D-glycero-D-talo-oct-2-ulosonic acid (KO) and/or 3-deoxy-D-manno-oct-2-ulosonic acid (KDO) residue, and/or a saccharide residue modified with a phospho-glycerol (Gro-P) substituent. The intelectin may be hIntL-1 or hIntL-2, and the subject is a human. The intelectin may be a non-human intelectin, and the subject is a non-human mammal of the same species as the intelectin, such as where the intelectin is mouse intelectin-1, and the subject is a mouse. The formulation may contain a probiotic supplement, a nutritional supplement, a vitamin supplement, a flavoring agent, and/or a probiotic bacterium. The formulation may be a yogurt, a kefir or a nutritional/health drink. The one or more of the beneficial microorganisms may express said intelectin. The intelectin may be PEGylated. The formulation may be an aerosol formulation or an oral formulation.

In still yet another embodiment, there is provided a method of detecting a bacterium or mixture of bacteria in a sample comprising (a) contacting said sample with an intelectin; and (b) detecting the binding of said intelectin to a bacterium or mixture of bacteria in said sample. The sample may be a fecal sample. The intelectin may be human intelectin-1, human intelectin-2 or mouse intelectin-1. Step (b) may comprise flow cytometry, wherein a label associated with said intelectin is detected. The result of step (b) may be compared to a standard, such as a comparable result from a healthy subject, or a comparable result from a diseased subject. The diseased subject may have dysbiosis, lactose intolerance, antibiotic-induced diarrhea, eczema, *Heliobacter pylori* infection, irritable bowel syndrome, colitis, necrotizing enterocolitis, or colorectal cancer. Step (b) may further comprise quantitation of said bacterium or bacterial mixture, and/or taxonomic identification of said bacterium or bacterial mixture. The sample may be a probiotic sample.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

(FIG. 1A) Structure of ligands used for characterization of hIntL-1 by ELISA and SPR. (FIG. 1B) The specificity of hIntL-1 for β-Galf, β-ribofuranose and β-galactopyranose was tested in an ELISA. Error bars represent the s.d. of the mean (n=3). (FIG. 1C) Affinity of hIntL-1 for carbohydrate ligands as measured in the ELISA. Affinities are reported as apparent Kd as they are calculated for the hIntL-1 disulfide-linked trimer, which can engage in multivalent binding (below). (FIG. 1D) SPR sensorgrams of hIntL-1 binding to immobilized carbohydrates. Complete data set is available in FIG. 9.

(FIG. 2A) Recombinant hIntL-1 binding to mammalian glycan microarray CFG v5.1 and a custom furanoside array. Error bars represent the standard deviation of the mean (n=4). (FIG. 2B) Recombinant IntL-1 ligands were identified using the microbial glycan array. The glycan array data are organized by genus in FIG. 11. Error bars represent the standard deviation of the mean (n=4). (FIG. 2C) Top 15 ligands identified in the microbial array. Species are designated to provide a sense of the breadth of hIntL-1 recognition. Of the top 15, *Y. pestis* KM260(11)-Δ0187 and KM260 (11)-6C are the only uncharacterized glycans. (FIG. 2D) Structural representation of the proposed ligands of hIntL-1 and which microbial glycans they are present in FIG. 2C. All of the ligands identified here have an exocyclic vicinal diol. L,D-α-heptose has an epimer, D,D-α-heptose with opposite sterochemisty at C(6). N-Acetylneuraminic acid (Neu5Ac) is included to depict its acyclic vicinal diol.

(FIG. 3A) Structure of the hIntL-1 disulfide-linked trimer complexed with allyl-β-D-Galf. Each monomer unit is depicted in a different color, while the β-Galf ligand is in black, calcium ions in green, and ordered water molecules in red. Two orientations are shown to indicate the relative positioning of the ligand-binding sites within the trimer. (FIG. 3B) Close-up of the ligand binding site. Residues involved in calcium coordination and ligand binding are highlighted using the three letter amino acid code.

FIGS. 5A-B. Intelectin Protein Primary Sequences are Highly Conserved Across Species. (FIG. 5A) Graphic representation of intelectin protein primary sequences aligned using Clustal W (hIntL-1=SEQ ID NO:4; hIntL-2=SEQ ID NO:5; mIntL-1=SEQ ID NO:6; mIntL-2=SEQ ID NO: 7; sIntL-1=SEQ ID NO:8; xIntL=SEQ ID NO:9). The consensus sequence is represented on the top (SEQ ID NO:10). Residues identical in every sequence are denoted with a red box. (FIG. 5B) Percentage sequence identity between intelectin proteins depicted in FIG. 5A.

FIGS. 6A-B. Intelectin and Ficolin Proteins are Significantly Divergent Despite Both Containing a Fibrinogen-Like Domain. (FIG. 6A) Graphic representation of intelectin and ficolin protein primary sequences aligned using Clustal W (hIntL-1=SEQ ID NO:4; mIntL-1=SEQ ID NO:6; xIntL=SEQ ID NO:9; h H-Ficolin=SEQ ID NO:11; h_L-Ficolin=SEQ ID NO:12; h_M-Ficolin=SEQ ID NO:13). The consensus sequence is represented on the top (SEQ ID NO:14). Resides identical in every sequence are denoted with a red box. Ficolin proteins contain a collagen-like domain near the N-terminus that is not present in intelectins, this region is highlighted with a box. (FIG. 6B) Percentage sequence identity between intelectin and ficolin proteins depicted in FIG. 6A. While both families of proteins are similar internally, intelectins and ficolins are divergent.

FIGS. 7A-B. Expression and Purification of hIntL-1. (FIG. 7A) Silver staining of a reducing SDS-PAGE analysis of hIntL-1 transfected conditioned culture media. These samples were taken 48 hours post transfection. hIntL-1 is indicated by the arrow. (FIG. 7B) Coomassie stained reducing and nonreducing SDS-PAGE analysis of hIntL-1 purified on an immobilized β-Galf column. The molecular weight of hIntL-1 when analyzed under nonreducing conditions is indicative of a disulfide-linked homotrimer.

FIGS. 8A-B. hIntL-1 Conditioned Culture Media Specifically Binds β-Galf. (FIG. 8A) Schematic of streptavidin based ELISA-like carbohydrate binding assay developed for assessing hIntL-1 ligand specificity. Any biotin functionalized carbohydrate can be immobilized and assayed. (FIG. 8B) hIntL-1 conditioned HEK culture media dose dependently binds β-Galf. Addition of 25 mM EDTA completely abolished binding. Error bars represent the standard deviation (n=2) of a technical replicate.

FIGS. 10A-D. Construction of a Furanoside Glycan Array. (FIG. 10A) Chemical structure of amine functionalized carbohydrates used in the furanoside glycan array. Carbohydrates were immobilized at varying density on an NETS-ester activated glass coverslip according to standard protocols (cite). NA2 and LNnT served as positive controls for immobilization. (FIG. 10B) and (FIG. 10C) specific recognition of LNnT and NA2 by *Erythrina cristagalli* lectin (ECL; FIG. 10B) and *Ricinus communis* agglutinin I lectin (RCAI; FIG. 10C) confirm the printing efficiency of the array. (FIG. 10D) The identity and ligand density of each spot on the furanoside array is shown for ease of analysis.

FIGS. 11A-E. Expression, purification and carbohydrate binding activity of hIntL-1. (FIG. 11A) Reducing SDS-PAGE analysis of HEK 293T culture medium from hIntL-1 transfected cells. Samples were analyzed by silver stain 48 hours post transfection. An arrow indicates the band corresponding to the molecular weight of a hIntL-1 reduced monomer. (FIG. 11B) Coomassie stained gels of samples subjected to reducing and nonreducing SDS-PAGE analysis of hIntL-1 purified on an immobilized β-Galf column. The molecular weight of the sample analyzed under non-reducing conditions corresponds to that of a disulfide-linked hIntL-1 homotrimer. (FIG. 11C) Schematic of streptavidin-based, ELISA-like carbohydrate binding assay developed for assessing hIntL-1 ligand specificity. Biotinfunctionalized carbohydrate is immobilized. Bound hIntL-1 is detected the enzyme horseradish peroxidase (HRP) conjugated to an antibody (either a secondary or directly conjugated primary), and a chromogenic HRP substrate. (FIG. 11D) Carbohydrate-binding activity of HEK 293T cell conditioned culture medium following transfection with hIntL-1 expression plasmid. The calcium ion dependence was tested by the addition of 25 mM EDTA. Data are presented as the mean (n=2 of a technical replicate and is representative of >3 independent experiments). (FIG. 11E) Complete data set of hIntL-1 SPR analysis presented in FIG. 1C. β-Ribofuranose and β-arabinofuranose were included as they were reported to be ligands of hIntL-1 (Tsuji et al., 2001). α-Rhamnose was included as a non-human monosaccharide.

FIGS. 12A-B. hIntL-1 Ligand Specificty Revealed by Microbial Glycan Array. (FIG. 12A) Results of the Microbial Glycan Microarray organized by genus and species, alphabetically. The fluorescence values are identical to those presented in FIG. 2B. The chemical epitope that is proposed to be a hIntL-1 ligand is depicted. The chart identification number from this graph is provided in parenthesis below the graphically depicted ligand. Data are presented as the mean±s.d. (n=4 of a technical replicate for each immobilized glycan). (FIG. 12B) Chemical structures of terminal α-Galf containing glycans that failed to bind hIntL-1. The Galf residues in each glycan are depicted in red. The BPS number (BPS #) that references each glycan (Stowell et al., 2014), and the hIntL-1 signal (from FIG. 2B) are shown.

FIGS. 13A-C. Structural alignment of hIntL-1 and human L-ficolin (PDB 2J3U). (FIG. 13A) Primary protein sequence and secondary structure comparison of hIntL-1 (SEQ ID NO:15) and L-ficolin (SEQ ID NO:16) (PDB: 2J3U; Garlatti et al., 2007) generated using ESPript 3.0 (Robert & Gouet, 2014). The figure was produced from a Clustal W alignment of hIntL-1 (residues 29-313) and L-ficolin (Residues 96-313). The residues depicted correspond to those that were resolvable in each protein structure. This alignment omits the collagen-like domain of L-ficolin. The box denotes the proposed fibrinogen-like domain (FBD) of each molecule. A red box highlights identical residues. The cysteine residues from hIntL-1 that are involved in intermolecular trimerization are identified with an arrow. (FIG. 13B) A hIntL-1 monomer (wheat) aligned to a L-ficolin monomer (PDB: 2J3U) (grey) using Gesamt v6.4 (Krissinel, E., 2012). Reported RMSD=3.6 Å for 165 superimposable Cα atoms between the two structures. After the first 165 Cα atoms, the structures are too divergent to assign Cα atoms as superimposable, and they are not included in this calculation. The co-crystallized carbohydrate ligands are depicted to highlight differences in ligand binding sites. The hIntL-1 ligand is shown in black and the L-ficolin ligand is shown in red. Calcium ions are shown in green. Human IntL-1 binds three calcium ions, while L-ficolin binds one. The N-termini are highlighted with an N. (FIG. 12C) The alignment shown in FIG. 13B, except that L-ficolin is translated by 45 Å for clarity. The N-terminus of each monomer is denoted with an N.

FIGS. 14A-D. hIntL-1 bound to allyl-β-D-Galf. (FIG. 14A) Structure of the ligand-binding site in Apo-hIntL-1 (4WMQ). Calcium ions are shown in green, and ordered water molecules in red. Dashed lines highlight functional groups important for the heptavalent coordination of the ligand binding site calcium ion. (FIG. 14B) Close-up view of the ligand-binding site of the β-GalfβhIntL-1 protein structure (4WMY). This image is the same as depicted in IG. 3B, although surface mesh is depicted around the β-Galf ligand to highlight the ligand electron density. Mesh represents a difference density map (mFo-DFc, 3σ). Calcium ions are depicted in green and ordered waters are shown in red. The ligand O(5) and O(6) hydroxyl groups coordinate to the calcium ion and displace two ordered water molecules. (FIG. 14C) Structural comparison of the crystallized allyl-β-D-Galf ligands. The molecule from Chain A is shown in wheat, while the molecule shown in Chain B is shown in grey. The furanosides were overlaid using the C(2)-C(3) bond and translated apart by 8 Å. (FIG. 14D) Table summarizing Chain A and Chain B in the β-Galf-hIntL-1 protein structure (4WMY).

FIG. 15A-B. hIntL-1 exhibits specificity for microbial glycan epitopes bearing terminal 1,2-diols. (FIG. 15A) hIntL-1 does not bind to immobilized α-Neu5Ac assayed by the ELISA-like carbohydrate-binding assay (FIG. 11C). Data are fit to a one site binding equation (solid lines). Data are presented as the mean (n=2 of a technical replicate and is representative of three independent experiments). (FIG. 15B) Inhibition of hIntL-1 binding to immobilized β-Galf. Four compounds (glycerol, 1-phosphoglycerol, the methyl-α-glycoside of Neu5Ac, and the methyl-α-D-mannopyranoside) were dissolved in binding buffer and included during the hIntL-1 incubation. Binding data shown are relative to a control where no competitor was added to the binding buffer. Data are presented as the mean (n=2 of a technical replicate and is representative of three independent experiments).

(FIG. 16A) Human intelectin-1 topology diagram. Amino acid residues important for calcium ion coordination and ligand binding are highlighted in blue, and magenta, respectively. (FIG. 16B) *Xenopus laevis* Intelectin-1 (XIntL-1 or XEEL) topology diagram. Amino acid residues important for calcium ion coordination and ligand binding are highlighted in blue, and magenta, respectively.

FIGS. 18A-C. hIntL-1 binding to the bacteria isolated from Lifeway® Kefir. (FIG. 18A) Forward vs. side scatter depiction of the bacteria isolated from Lifeway® Kefir. The scatter plot reports on its size and shape complexity of the sample. Similar to what is reported, the sample is composed of many species of microorganisms. (FIG. 18B) Overlay of the histograms of unstained, cells stained in the presence of calcium ions, and cells stained in the presence of EDTA. The cells stained in the presence of hIntL-1 and calcium ions split into two populations, one that is bound strongly by hIntL-1 and one that is not. (FIG. 18C) Each sample is shown individually. Included in each image is a quantitative assignment of the fraction of cells bound by hIntL-1. In the Kefir Cell+15 μg/mL hIntL-1+10 mM $CaCl_2$, 79% of the cells are bound by hIntL-1.

FIGS. 19A-C. hIntL-1 binding to an adult male fecal microbiome. (FIG. 19A) Forward vs. side scatter plot from a human fecal microbiome sample. (FIG. 19B) Overlay of the histograms of unstained, cells stained in the presence of calcium ions, and cells stained in EDTA. A second population of cells that are bound by hIntL-1 is present when stained in the presence of calcium ions. (FIG. 19C) Each sample is shown individually. Included within each image is a quantitative assignment of the fraction of cells bound by hIntL-1. These data provide an indication of the diversity of the cell population bound by hIntL-1.

FIGS. 20A-B. hIntL-1 binding to an infant male fecal microbiome. (FIG. 20A) Forward vs. side scatter plot from a human infant fecal microbiome sample. (FIG. 20B) Each sample is shown individually. Included within each image is a quantitative assignment of the fraction of cells bound by hIntL-1. These data provide an indication of the diversity of the cell population bound by hIntL-1. In the Infant microbiome sample+15 µg/mL hIntL-1+10 mM $CaCl_2$, 24.5% of the cells are bound by hIntL-1.

FIGS. 21A-B. hIntL-2 binding to an infant male fecal microbiome. (FIG. 21A) Forward vs. side scatter plot from a human infant fecal microbiome sample. (FIG. 21B) Each sample is shown individually. Included within each image is a quantitative assignment of the fraction of cells bound by hIntL-2. These data provide an indication of the diversity of the cell population bound by hIntL-2. In the Infant microbiome sample+15 µg/mL hIntL-2+10 mM $CaCl_2$, 32.2% of the cells are bound by hIntL-1.

Figure 22A:
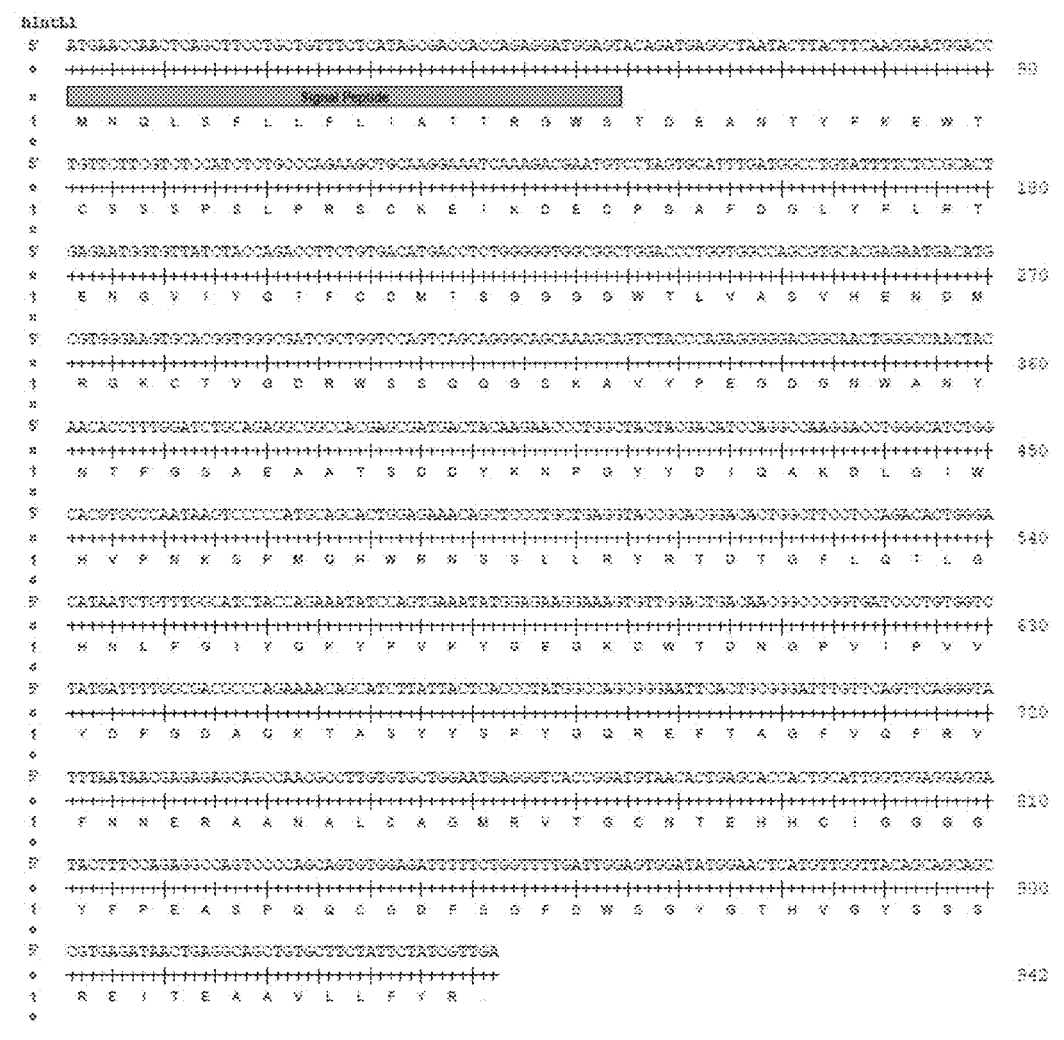
Figure 22B:
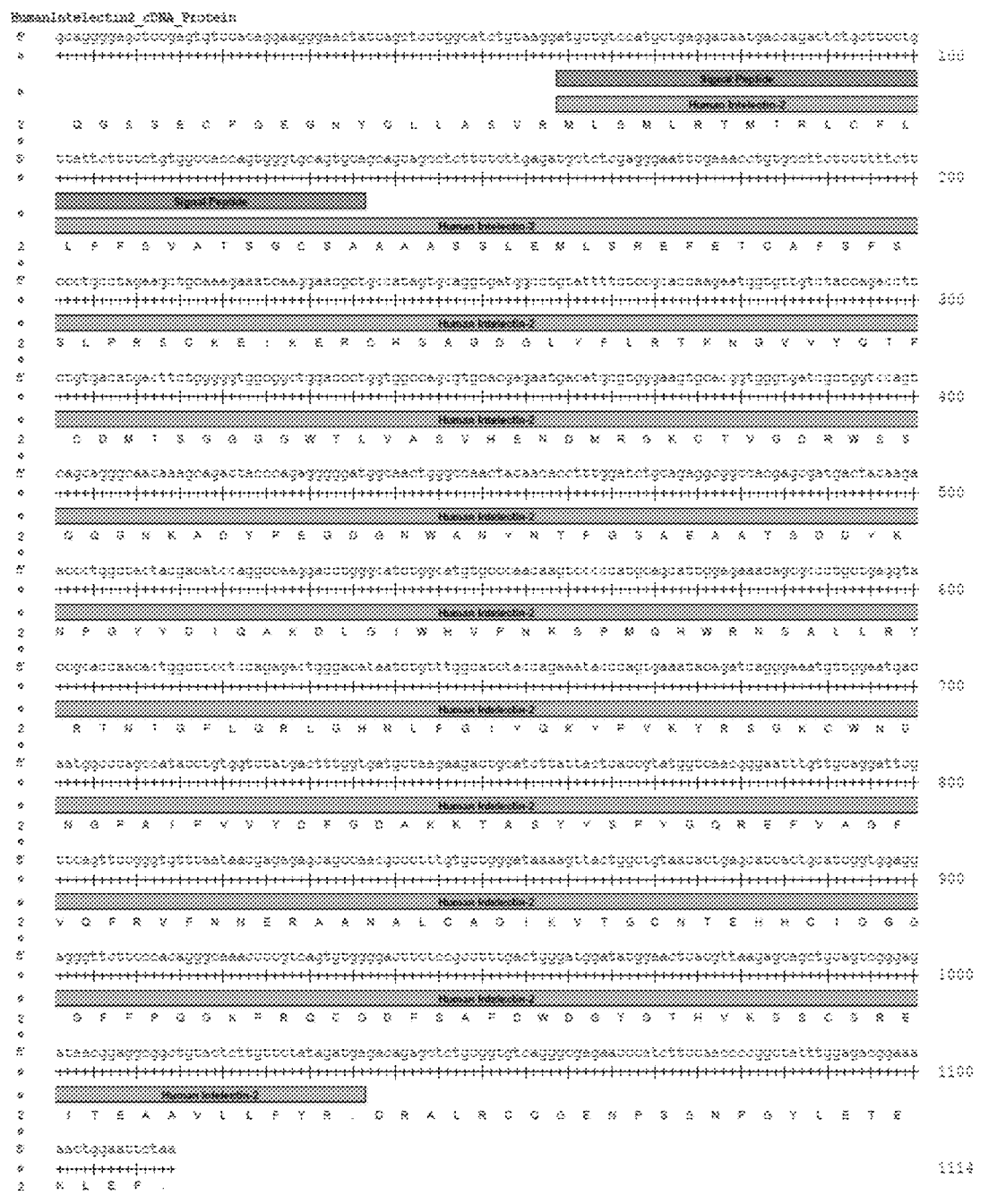
Figure 22C:
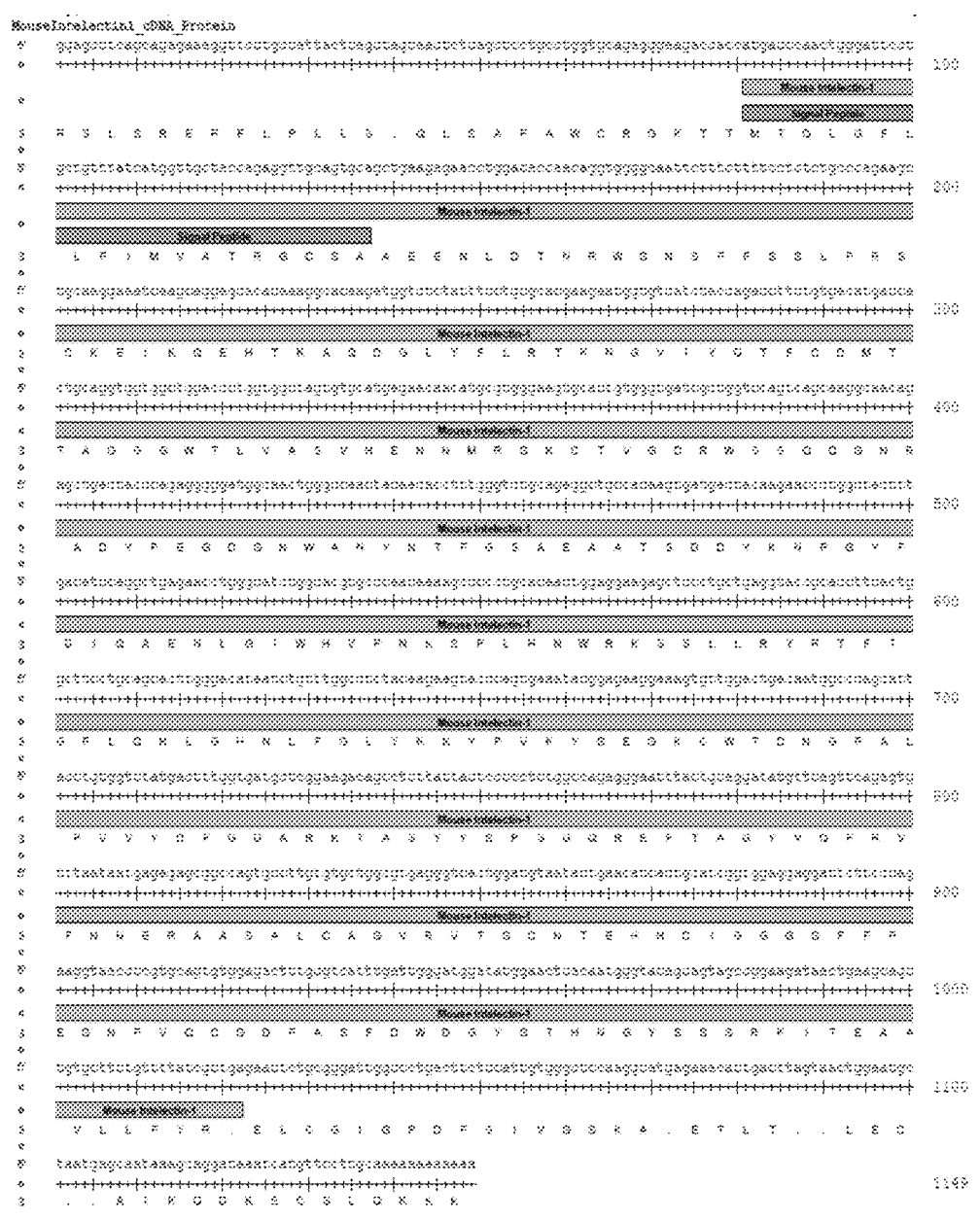
Figure 22D:
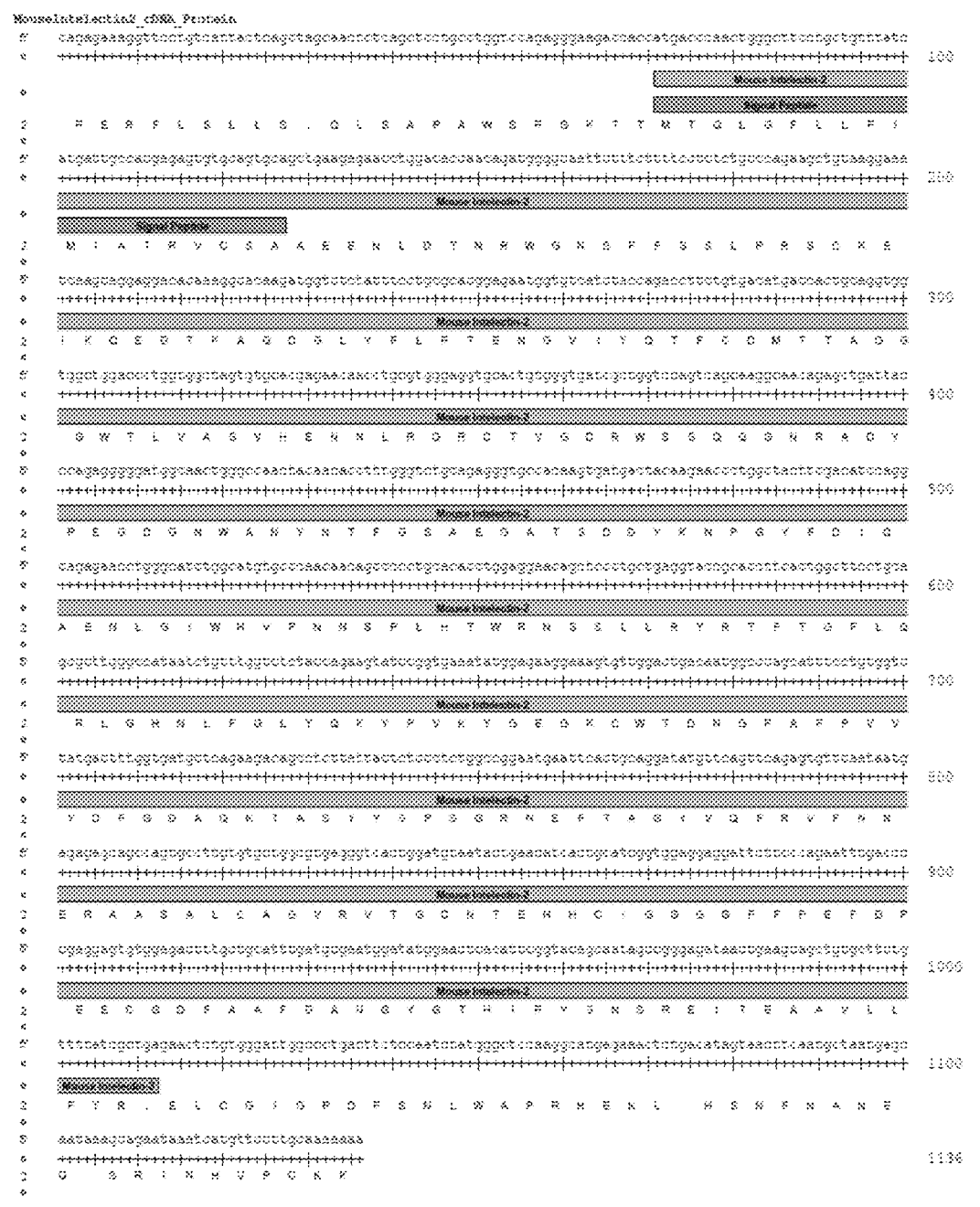

FIGS. 22A-D. Intelectin sequences. (FIG. 22A) Human intelectin 1 sequences (nucleic acid=SEQ ID NO:17; amino acid=SEQ ID NO:18). (FIG. 22B) Human intelectin 2 sequences (nucleic acid=SEQ ID NO:19; amino acid=SEQ ID NO:20). (FIG. 22C) Mouse intelectin 1 sequences (nucleic acid=SEQ ID NO:21; amino acid=SEQ ID NO:22). (FIG. 22D) Mouse intelectin 2 sequences (nucleic acid=SEQ ID NO:23; amino acid=SEQ ID NO:24).

DETAILED DESCRIPTION OF ILLUSTRATIVE EMBODIMENTS

Figure 1:
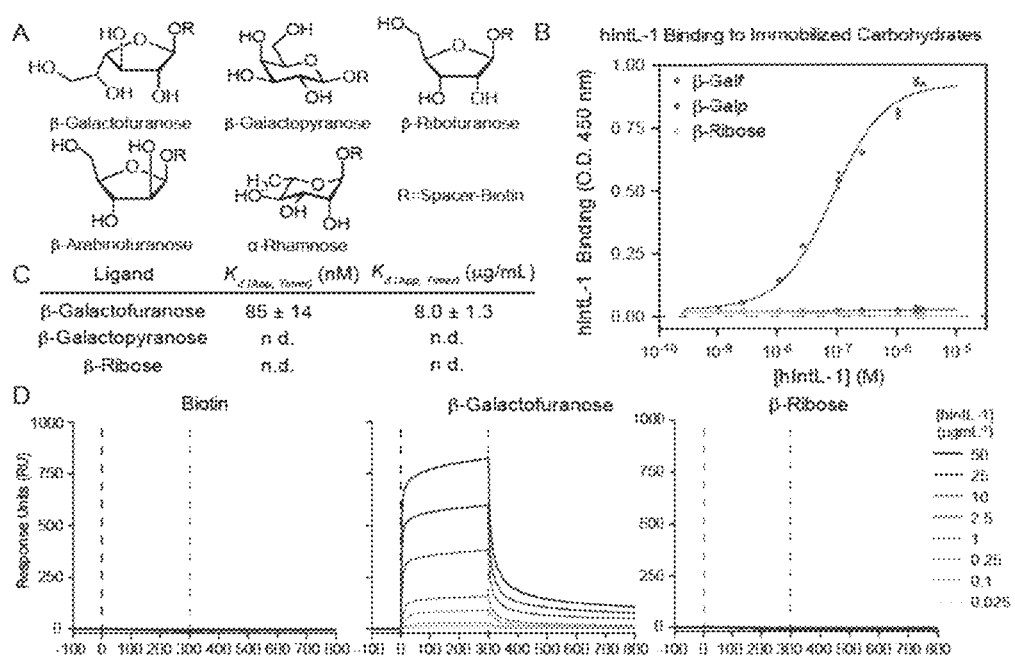
FIGS. 1A-D. hIntL-1 selectively binds β-Galf with high affinity.

The physiological mechanisms by which humans influence their microbiome are unclear. As discussed in the Examples, and reported in Wesener et al. (2015), the inventors have determined the human lectin intelectin-1 (hIntL-1) exhibits the remarkable ability to bind to many different glycans that occur on microbial cell surfaces. Human IntL-1 is expressed predominantly by the goblet and paneth cells of the intestine and lung. Its presence at these mucosal barriers is intriguing, and human mutations are associated with asthma and Crohn's Disease.

This lectin fails to bind surface carbohydrates produced by mammalian cells, but rather recognizes a variety of glycans on bacterial cells. The epitope on the glycans bound by hIntL-1 is an exocyclic-1,2-diol. The inventors solved the structure of hIntL-1 bound to β-Galf and demonstrated that the protein uses a bound calcium ion to selectively coordinate to the shared acyclic diol epitope. The high selectivity of hIntL-1 for microbial glycans is unique amongst lectins, as it only recognizes nonhuman carbohydrates. The available data are consistent with a role for hIntL-1 in influencing the composition of the microbiome.

The physiological role for hIntL-1 is predicted to be a prebiotic (i.e., a molecule that itself can augment individuals microbiomes, hIntL-1 may bind to "good bacteria" to capture and maintain them in the GI) or as an antibiotic (i.e., it helps preserve mucosal barriers by targeting bacteria that breach those barriers). In the latter capacity, hIntL-1 may collaborate with the intestinal mucus layer to help spatially regulate the microbiome. This spatial segregation is important for reducing one hallmark of IBS symptoms, a chronic state of inflammation. The inventors propose that increasing the levels of hIntL-1 will facilitate regeneration and fortification of the mucosal layer responsible for spatially regulating the microbiome. Increasing the amount of hIntL-1 can be achieved genetically, or through supplementation of hIntL-1 through ingestion. In this way, it can serve to improve patient microbiome profiles and health.

Alternatively, hIntL-1 may function as a prebiotic and help to recruit and retain beneficial microbiome bacteria. This role also suggests that hIntL-1 could be exploited. For example, the influence of probiotics is temporary, as the beneficial bacteria are retained for only a short time period (1 day). Adding recombinant hIntL-1 protein as a prebiotic to a probiotic regimen may help to retain beneficial bacteria. This type of approach would be especially beneficial in addressing dysbiosis (microbial imbalance). Infant dysbiosis is an important problem that occurs in infant that are not breastfeeding or that require a course of antibiotics. Intriguingly, hIntL-1 preferentially interacts with multiple *Bifidobactium* species (vide infra), which preferentially colonize the gut of breast fed infants. It is the *Bifidobactium* species that are thought to contribute to some of the benefits of breast-feeding for immune function and overall health. Thus, the specificity of hIntL-1 suggests that it could be used to boost overall health. These and other aspects of the disclosure are discussed in detail below.

I. INTELECTINS

Mammals place glycans on their cell surfaces that differ markedly from many of those present on microbes. Lectins that selectively recognize microbial glycans would be useful to distinguish between host and microbe, but the human lectins described to date can interact with human glycans. All cells are covered with a coat of glycans. Differences in the glycan coat can serve as markers of a cell's identity—its developmental state, its tissue type, or whether it is self- or non-self. To specifically recognize differences in glycosylation, humans use carbohydrate binding proteins, or lectins. The importance of glycosylation to human health is highlighted by the fact that 1-2% of the genes of any organism encode for enzymes predicted to be involved in glycosylation. Indeed, glycans are key biomolecules of molecular recognition.

Figure 6A:
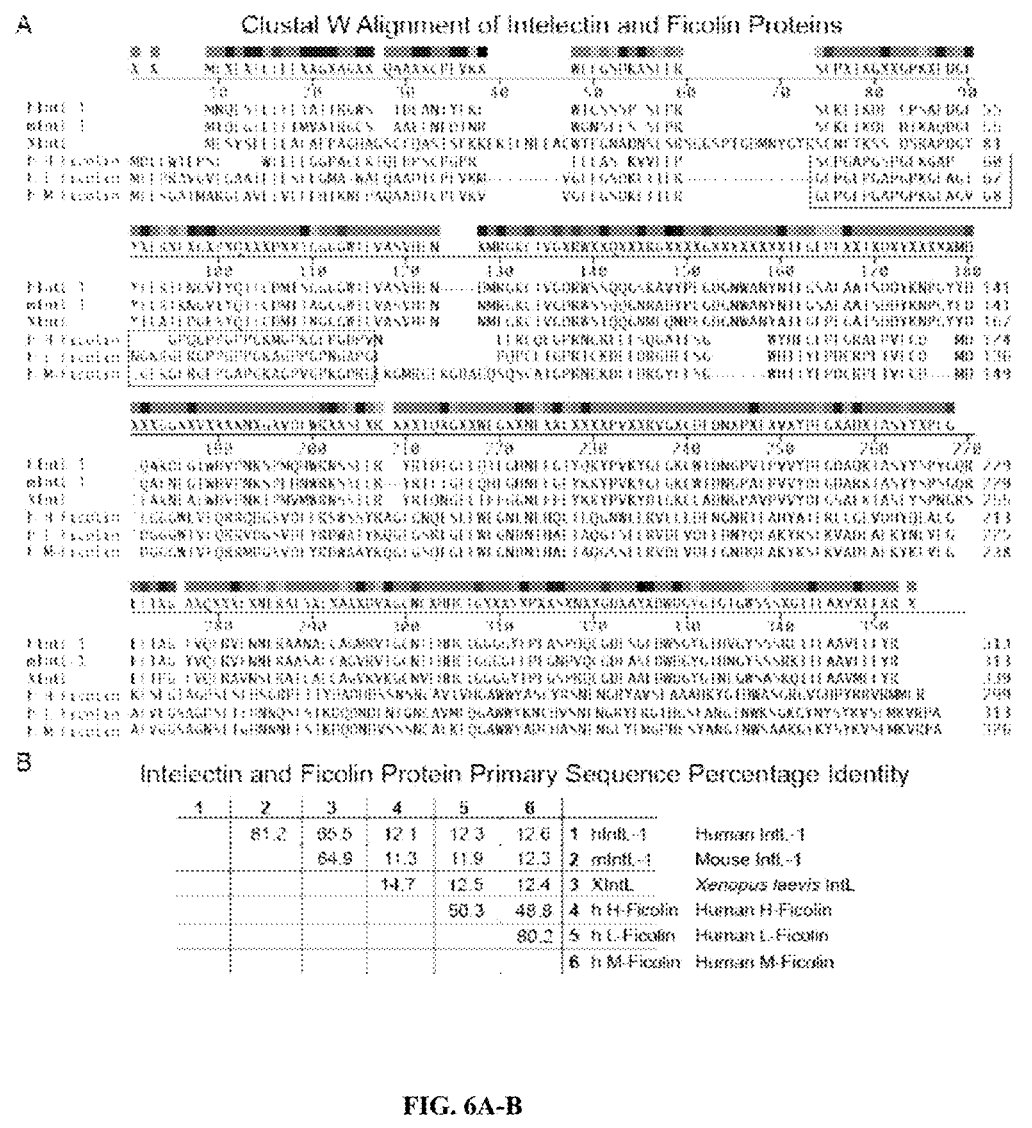

Intelectins are a recently discovered class of animal lectins not sequence identical to known C-type lectins (Drickamer, 1993), but in many cases have been shown to bind carbohydrates in a calcium dependent manner. The first intelectin protein was identified in *Xenopus laevis* oocytes and assigned the name XL-35 (Lee et al., 1997). Since then, homologs have been identified in a wide variety of animals; notable examples include lamprey, trout, sheep, mice and humans. Although intelectin family members share a high degree of sequence identity (FIGS. 5A-B), only a small 45-residue (residues 37-82 in hIntL-1 (Tsuji et al., 2001)) fibrinogen-like domain (FBD) shares sequence similarity to other proteins (Thomsen et al., 2011). In addition to intelectins, the FBD is found in other lectins, the best studied being innate immune lectins from the ficolin family. However the predicted domain architecture and primary sequence differ significantly between intelectins and ficolins (FIGS. 6A-B).

Compared to other lectin families, little is known about intelectins biochemically and biologically. There are no definitive experiments that define their carbohydrate binding specificity and no high resolution protein structures available. Mammalian intelectins are expressed by lung and intestinal goblet cells and by intestinal paneth cells. Based on their expression localization and inclusion of a FBD, intelectins are proposed to be lectins of the innate immune system. Expression upregulation of mammalian intelectins in sheep and mice upon infection with intestinal parasitic nematodes support this (Pemberton et al., 2004; Datta et al., 2005; Voehringer et al., 2007; French et al., 2008). Confoundingly, several other biological roles have been suggested for human intelectins independent of their proposed lectin function. Intelectin is proposed to bind lactoferrin and serve as a GPI-anchored intestinal lactoferrin receptor (Suzuki et al., 2001). Studies in humans (Pemberton et al., 2008; Kerr et al., 2014) and mice (Kuperman et al., 2005) have linked intelectin to asthma and airway inflammation. And lastly, intelectin is believed to act as a novel human adipokine, termed omentin, that stimulates insulin-mediated glucose uptake and serves as a predictive biomarker of metabolic disease (Yang et al., 2006). All of these biological roles have been linked to intelectins.

Two human intelectin homologs have been identified; they were termed intelectin-1 and -2 (Lee et al., 2001). The calcium dependent carbohydrate binding activity of hIntL-1 was examined soon after (Tsuji et al., 2001). Data from this study suggested that hIntL-1 promiscuously bound carbohydrate ligands with low affinity. The highest affinity ligand identified was the pentose furanoside, D-ribose, with an apparent $K_D$ 5 mM. Among the other ligands identified for hIntL-1 in this study was the disaccharide 2-acetamido-2-deoxy-4-O-beta-D-galactofuranosyl-D-glucopyranose, with a reported apparent affinity of 9 mM. The carbohydrate D-galactofuranose (Galf) is the thermodynamically disfavored five-membered ring isomer of D-galactose. Examples of Galf have been described in bacteria, protozoans, fungi, and nematodes (Nassau et al., 1996; Tefsen et al., 2012; Wesener et al., 2013; Pederson & Turco, 2003). Mammals lack the enzyme uridine 5'-diphosphate (UDP) galactopyranose mutase (UGM) that is requisite for biosynthesis of the Galf glycosyl donor (Blixt et al., 2004). Hence, Galf is a nonhuman glycan epitope and could be used to specifically assign non-self status to cells. Combined with the previously mentioned expression profile, data suggest a role for hIntL in detecting microbial specific glycan epitopes in the lung and gastrointestinal tract.

II. MICROBIOME AND HEALTH

A. Probiotics

Probiotics are microorganisms that are believed to provide health benefits when consumed. The term probiotic is currently used to name ingested microorganisms associated with beneficial effects to humans and animals. The term came into more common use after 1980. The introduction of the concept is generally attributed to recipient Élie Metchnikoff, who in 1907 suggested that "the dependence of the intestinal microbes on the food makes it possible to adopt measures to modify the flora in our bodies and to replace the harmful microbes by useful microbes." A significant expansion of the potential market for probiotics has led to higher requirements for scientific substantiation of putative beneficial effects conferred by the microorganisms. Studies on the medical benefits of probiotics have yet to reveal a cause-effect relationship, and their medical effectiveness has yet to be conclusively proven for most of the studies conducted thus far.

Commonly claimed benefits of probiotics include the decrease of potentially pathogenic gastrointestinal microorganisms, the reduction of gastrointestinal discomfort, the strengthening of the immune system, the improvement of the skin's function, the improvement of bowel regularity, the strengthening of the resistance to cedar pollen allergens, the decrease in body pathogens, the reduction of flatulence and bloating, the protection of DNA, the protection of proteins and lipids from oxidative damage, and the maintaining of individual intestinal microbiota in subjects receiving antibiotic treatment. Scientific evidence to date has been insufficient to substantiate any antidisease claims or health benefits from consuming probiotics.

1. Definition

The World Health Organization's 2001 definition of probiotics is "live micro-organisms which, when administered in adequate amounts, confer a health benefit on the host". Following this definition, a working group convened by the FAO/WHO in May 2002 issued the "Guidelines for the Evaluation of Probiotics in Food". This first global effort was further developed in 2010, two expert groups of academic scientists and industry representatives made recommendations for the evaluation and validation of probiotic health claims. The same principles emerged from those groups as the ones expressed in the Guidelines of FAO/WHO in 2002. This definition, although widely adopted, is not acceptable to the European Food Safety Authority because it embeds a health claim which is not measurable.

A consensus definition of the term "probiotics", based on the available information and scientific evidence, was adopted after a joint Food and Agricultural Organization of the United Nations and World Health Organization expert consultation. In October 2001, this expert consultation defined probiotics as: "live micro-organisms which, when administered in adequate amounts, confer a health benefit on the host". The FAO/WHO consultation was also a first effort towards the assessment of probiotics efficacy and resulted in May 2002 in a document named "Guidelines for the Evaluation of Probiotics in Food". This effort is accompanied by local governmental and supra-governmental regulatory bodies' requirements to better characterize health claims substantiations.

2. Use

Probiotics have to be alive when administered. One of the concerns throughout the scientific literature resides in the viability and reproducibility on a large scale of the observed results, as well as the viability and stability during use and storage, and finally the ability to survive in stomach acids and then in the intestinal ecosystem. Probiotics must have undergone controlled evaluation to document health benefits in the target host. Only products containing live organisms shown in reproducible human studies to confer a health benefit can actually claim to be a probiotic. The correct definition of health benefit, backed with solid scientific evidence, is a strong element for the proper identification and assessment of the effect of a probiotic. This aspect represents a major challenge for scientific and industrial investigations because several difficulties arise, such as variability in the site for probiotic use (oral, vaginal, intestinal) and mode of application.

The probiotic candidate must be a taxonomically defined microbe or combination of microbes (genus, species, and strain level). It is commonly admitted that most effects of probiotic are strain-specific and cannot be extended to other probiotics of the same genus or species. This calls for a precise identification of the strain, i.e. genotypic and phenotypic characterization of the tested microorganism.

Probiotics must be safe for their intended use. The 2002 FAO/WHO guidelines recommend that, though bacteria may be generally recognized as safe (GRAS), the safety of the potential probiotic should be assessed by the minimum required tests:
  determination of antibiotic resistance patterns
  assessment of certain metabolic activities (e.g., D-lactate production, bile salt deconjugation)
  assessment of side effects during human studies
  epidemiological surveillance of adverse incidents in consumers (after market)

If the strain under evaluation belongs to a species that is a known mammalian toxin producer, it must be tested for toxin production. One possible scheme for testing toxin production has been recommended by the EU Scientific Committee on Animal Nutrition If the strain under evaluation belongs to a species with known hemolytic potential, determination of hemolytic activity is required In Europe, EFSA has adopted a premarket system for safety assessment of microbial species used in food and feed productions, to set priorities for the need of risk assessment. The assessment is made for a selected group of microorganisms, which if favorable, leads to the "Qualified Presumption of Safety" status.

Finally, probiotics must be supplied in adequate numbers, which may be defined as the number able to trigger the targeted effect on the host. It depends on strain specificity, process, and matrix, as well as the targeted effect. Most of reported benefits demonstrated with the traditional probiotics have been observed after ingestion of a concentration around $10^7$ to $10^8$ probiotic cells per gram, with a serving size around 100 to 200 mg per day.

B. Beneficial Bacteria

1. Lactobacilli

*Lactobacillus acidophilus* is the most well known probiotic and one of the most important for the health of the small intestine. Besides the linging of the intestine, *Acidophilus* can also take up residence in the vagina, cervix or urethra. *Acidophilus* inhibits pathogens, and produces such natural antibiotics as lactocidin and acidophilin, which enhance immunity. *Acidophilus* has anti-microbial effects against *Staphylococcus aureus, Salmonella, E. coli* and *Candida albicans*.

Other Lactobacilli include *Lactobacillus brevis*, a lactic acid producing probiotic that is helpful in synthesizing Vitamins D and K. *L. bulgaricus*, used in yogurt fermentation plays a protective role by producing lactic acid, which creates a friendly environment for other species. *L. plantarum* makes lactolin, another natural antibiotic. *Plantarum* can also synthesize L-lysine, an anti-viral amino acid. This organism eliminates nitrate, promoting nitric oxide levels and decreases pathogens.

*L. rhamnosus* has a high tolerance to bile salts, surviving in less than favorable environments. This species has shown benefit to the elderly and infants alike. *Rhamnosus* helps with lactose intolerance, protects the small intestine, and produces lactic acid in the large intestine.

Other strains of Lactobacilli include *L. fermentum, L. caucasicus, L. helveticus, L. lactis, L. reuteri* and *L. casei*.

2. Bifidobacteria *Bifidobacterium bifidum* is the most recognized of this category. Living within the mucus lining of the large intestine and/or vaginal tract, *bifidum* prevents pathogenic bacteria and yeast from invading. *Bifidum* creates favorable changes in pH levels by producing lactic and acetic acids. In addition, this species increase absorption of iron, calcium, magnesium and zinc.

*B. infantis* simulates the production of cytokines that affect the immune system, and can kill off such pathogens as *Clostrida, Salmonella* and *Shigella*. *B. longum* colonizes the large intestine. It prevents unfriendly bacteria and yeast from taking residence. This can decrease the frequency of gastrointestinal problems, such as diarrhea, and nausea during antibiotic use.

3. Other Strains

*Streptococcus thermophilus* is another probiotic used to make yogurt. Breaking down lactose to create lactase, the enzyme that digests milk sugars, this species can help with lactose intolerance. Other Streptococcal strains include *S. cremoris, S. faecium* and *S. infantis*.

*Enterococcus faecium* has shown in studies to be helpful for diarrhea, shortening duration of symptoms. It kills pathogenic microbes, such as rotavirus. Studies have also shown this strain to lower LDL or bad cholesterol. This organism is very resistant to antibiotics. Although a transient guest, *Enterococcus faecium* is a welcome natural resident in the human body.

C. Disease States Addressed by Probiotics

The following disease states are exemplary of conditions that can be ameliorated with the use of probiotics.

1. Diarrhea

Some probiotics are suggested as a possible treatment for various forms of gastroenteritis, and a Cochrane Collaboration meta-analysis on the use of probiotics to treat acute infectious diarrhea based on a comprehensive review of medical literature through 2010 (35 relevant studies, >4500 participants) reported that use of any of the various tested probiotic formulations appeared to reduce the duration of diarrhea by a mean of 25 hours (vs. control groups, 95% confidence interval, 16-34 hours), also noting, however, that "the differences between the studies may be related to other unmeasured and unexplored environmental and host factors" and that further research was needed to confirm reported benefits.

Some of the best evidence in support of probiotic health benefits is in the treatment of antibiotic-associated diarrhea (AAD). Antibiotics are a common treatment for children, and 20% of antibiotic-treated children develop diarrhea. AAD results from an imbalance in the colonic microbiota caused by antibiotic therapy. Microbiota alteration changes carbohydrate metabolism, with decreased short-chain fatty acid absorption and osmotic diarrhea as a result. The preventive role of some probiotics has been correctly assessed in randomized, controlled clinical trials. A review assessing the work of 16 different studies representing the evaluation of more than 3,400 patients concluded that the evidence gathered suggested a protective effect of some probiotics in this condition. In adults, some probiotics showed a beneficial role in reducing the occurrence of AAD. Another consequence of antibiotic therapy leading to diarrhea is the overgrowth of potentially pathogenic organisms such as *Clostridium difficile*.

Probiotic treatment might reduce the incidence and severity of AAD as indicated in several meta-analyses. For example, treatment with probiotic formulations including *L. rhamnosus* may reduce the risk of AAD, improve stool consistency during antibiotic therapy, and enhance the immune response after vaccination. However, further documentation of these findings through randomized, double-blind, placebo-controlled trials is required to confirm specific effects and obtain regulatory approval, which currently does not exist.

The potential efficacy of probiotic AAD prevention is dependent on the probiotic strain(s) used and on the dosage. A Cochrane Collaboration systematic review, in which 16 randomized clinical trials (n=3432 participants) were analyzed, concluded that treatments with less than 5000 million CFUs/day did not show a significant decrease of AAD. However, patients treated with ≥5000 million CFUs/day (including *L. rhamnosus* and *Saccharomyces boulardii*) had 60% lower relative risk (95% CI: 44-71%) of experiencing AAD than untreated patients.

2. Lactose Intolerance

Ingestion of certain active strains may help lactose-intolerant individuals tolerate more lactose than they would otherwise have tolerated.

3. Cholesterol

Preliminary human and animal studies have demonstrated the efficacy of some strains of lactic acid bacteria (LAB) for reducing serum cholesterol levels, presumably by breaking down bile in the gut, thus inhibiting its reabsorption (where it enters the blood as cholesterol). A meta-analysis that included five double-blind trials examining the short-term (2-8 weeks) effects of a yogurt with probiotic strains on serum cholesterol levels found a minor change of 8.5 mg/dL (0.22 mmol/L) (4% decrease) in total cholesterol concentration, and a decrease of 7.7 mg/dL (0.2 mmol/L) (5% decrease) in serum LDL concentration. A slightly longer study evaluating the effect of a yogurt with probiotic strains on 29 subjects over six months found no statistically significant differences in total serum cholesterol or LDL values. However, the study did note a significant increase in serum HDL from, 50 to 62 mg/dL (1.28 to 1.6 mmol/L) following treatment. This corresponds to a possible improvement of LDL/HDL ratio.

4. Blood Pressure

The consumption of probiotics may effect a modest benefit in helping to control high blood pressure.

5. Immune Function and Infections

Some strains of LAB may affect pathogens by means of competitive inhibition (i.e., by competing for growth) and some evidence suggests they may improve immune function by increasing the number of IgA-producing plasma cells and increasing or improving phagocytosis, as well as increasing the proportion of T lymphocytes and natural killer cells. Clinical trials have demonstrated that probiotics may decrease the incidence of respiratory-tract infections and dental caries in children. LAB products might aid in the treatment of acute diarrhea, and possibly affect rotavirus infections in children and travelers' diarrhea in adults, but no products are approved for such indications.

6. *Helicobacter pylori*

Some strains of LAB may affect *Helicobacter pylori* infections (which may cause peptic ulcers) in adults when used in combination with standard medical treatments, but no standard in medical practice or regulatory approval exists for such treatment.

7. Inflammation

Some strains of LAB may modulate inflammatory and hypersensitivity responses, an observation thought to be at least in part due to the regulation of cytokine function. Clinical studies suggest they can prevent reoccurrences of inflammatory bowel disease in adults, as well as improve milk allergies. How probiotics may influence the immune system remains unclear, but a potential mechanism under research concerns the response of T lymphocytes to proinflammatory stimuli.

Other areas in which inflammatory activity may be modulated by the microbiome include the lung, such as with asthma.

8. Irritable Bowel Syndrome and Colitis

Probiotics may help people with irritable bowel syndrome, although uncertainty remains around which type of probiotic works best, and around the size of the effect.

9. Necrotizing Enterocolitis

Several clinical studies provide evidence for the potential of probiotics to lower the risk of necrotizing enterocolitis (NEC) and mortality in premature infants. One meta-analysis indicated that probiotics reduce all-cause mortality and risk of having NEC by more than 50% compared with controls.

10. Vitamin Production

Probiotic treatment has been studied as a means of addressing maladies associated with vitamin deficiency, e.g., of vitamin K, folic acid, and vitamin B12.

11. Eczema

Probiotics are commonly given to breast-feeding mothers and their young children to prevent eczema, but some doubt exists over the strength of evidence supporting this practice.

12. Bacterial Vaginosis

Probiotic treatment of bacterial vaginosis is the application or ingestion of bacterial species found in the healthy vagina to cure the infection of bacteria causing bacterial vaginosis. This treatment is based on the observation that 70% of healthy females have a group of bacteria in the genus *Lactobacillus* that dominate the population of organisms in the vagina. Currently, the success of such treatment has been mixed since the use of probiotics to restore healthy populations of *Lactobacillus* has not been standardized. Often, standard antibiotic treatment is used at the same time that probiotics are being tested. In addition, some groups of women respond to treatment based upon ethnicity, age, number of sexual partners, pregnancy, and the pathogens causing bacterial vaginosis. In 2013, researchers found that administration of hydrogen peroxide producing strains, such as *L. acidophilus* and *L. rhamnosus*, were able to normalize vaginal pH and rebalance vaginal flora, preventing and alleviating bacterial vaginosis.

13. Obesity

Obesity has become a major health problem in the United States and other developed nations. In the United States, 65% of the adult population is considered overweight or obese, and more than 30% of adults meet the criteria for obesity. The World Health Organization has estimated that more than 1 billion adults worldwide are overweight, with 300 million of these considered clinically obese. The incidence of obesity in children is also growing rapidly in many countries. Obesity is a major risk factor for cardiovascular disease, stroke, insulin resistance, type 2 diabetes, liver disease, neurodegenerative disease, respiratory diseases and other severe illnesses, and has been implicated as a risk factor for certain types of cancer including breast and colon cancer.

Aside from its impacts on physical health, obesity has significant adverse effects on quality of life and psychological well-being. The incidence of obesity, already high, is likely to grow as a result of increasingly sedentary lifestyles in many countries. In addition, certain widely used psychiatric drugs, notably atypical antipsychotics, are associated with weight gain and increased risk of diabetes. Since these drugs must be used chronically to achieve adequate control of psychiatric symptoms, and treatment compliance in patients with mental disorders is frequently poor, these side effects present both a barrier to compliance and a significant additional health risk to patients.

There is evidence that lower intelectin levels correlate with obesity. Therefore, a probiotic regimen involving intelectins may help control of weight gain, or perhaps even promote weight loss.

14. Atherosclerosis

Atherosclerosis (also known as arteriosclerotic vascular disease or ASVD) is a specific form of arteriosclerosis in which an artery-wall thickens as a result of invasion and accumulation of white blood cells (WBCs) (foam cell) and proliferation of intimal-smooth-muscle cell creating a fibro-fatty plaque.

The accumulation of the white blood cells is termed "fatty streaks" early on because of the appearance being similar to that of marbled steak. These accumulations contain both living, active WBCs (producing inflammation) and remnants of dead cells, including cholesterol and triglycerides. The remnants eventually include calcium and other crystallized materials within the outermost and oldest plaque. The "fatty streaks" reduce the elasticity of the artery walls. However, they do not affect blood flow for decades because the artery muscular wall enlarges at the locations of plaque. The wall stiffening may eventually increase pulse pressure; widened pulse pressure is one possible result of advanced disease within the major arteries.

Atherosclerosis is therefore a syndrome affecting arterial blood vessels due to a chronic inflammatory response of WBCs in the walls of arteries. This is promoted by low-density lipoproteins (LDL, plasma proteins that carry cholesterol and triglycerides) without adequate removal of fats and cholesterol from the macrophages by functional high-density lipoproteins (HDL). It is commonly referred to as a "hardening" or furring of the arteries. It is caused by the formation of multiple atheromatous plaques within the arteries.

There is some evidence that intelectins can counteract atherosclerosis (Watanabe et al., 2016; Hiramatsu-Ito et al., 2016). Therefore, a probiotic regimen involving intelectins may help reduce atherosclerotic lesion formation.

III. POLYPEPTIDES/PEPTIDES/FUSIONS

A. Intelectins and Variants Thereof

The present disclosure contemplates the production and use of various intelectin polypeptides. The sequences (cDNA and protein) of human intelectins-1 and -2, and moues intelectins-1 and -2 are provided in FIGS. 22A-D, respectively. Variants of human intelectin-1 include a Val109Asp substitution sometimes found in diabetic and chronic IBD patients.

Intelectins have also been identified in various fish, including zebrafish (intelectins 1-3), catfish and rainbow trout.

B. Synthesis

1. Recombinant Techniques

For producing larger protein sequences, recombinant techniques are preferred. Such techniques are well known to those of skill in the art. Such techniques generally rely on the use of expression vectors that contain the machinery necessary to produce the protein of interest. Hence, the term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1989 and Ausubel et al., 1994, both incorporated herein by reference).

The term "expression vector" refers to any type of genetic construct comprising a nucleic acid coding for an RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control" and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous" or "homologous." Similarly, an enhancer may be one naturally associated with a nucleic acid sequence, located either downstream or upstream of that sequence. Alternatively, certain advantages will be gained by positioning the coding nucleic acid segment under the control of a recombinant, exogenous or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in prokaryotic recombinant DNA construction include the β-lactamase (penicillinase), lactose and tryptophan (trp) promoter systems.

Naturally, it will be important to employ a promoter and/or enhancer that effectively directs the expression of the DNA segment in the organelle, cell, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

Vectors can include a multiple cloning site (MCS), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression.

The vectors or constructs will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In expression, particularly eukaryotic expression, one will typically include a polyadenylation signal to effect proper polyadenylation of the transcript. The nature of the polyadenylation signal is not believed to be crucial to the successful expression, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

In certain embodiments, cells containing a nucleic acid constructs may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

In certain embodiments, a plasmid vector is contemplated for use to transform a host cell. In general, plasmid vectors containing replicon and control sequences which are derived from species compatible with the host cell are used in connection with these hosts. In addition, phage vectors containing replicon and control sequences that are compatible with the host microorganism can be used as transforming vectors in connection with these hosts. The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells).

Suitable non-viral methods for nucleic acid delivery for transformation of an organelle, a cell, a tissue or an organism for use with the current disclosure are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection, by injection, including microinjection; by electroporation; by calcium phosphate precipitation; by using DEAE-dextran followed by polyethylene glycol; by direct sonic loading; by liposome-mediated transfection and receptor-mediated transfection; by microprojectile bombardment; and any combination of such methods. Through the application of techniques such as these, organelle(s), cell(s), tissue(s) or organism(s) may be stably or transiently transformed.

As used herein, the terms "cell," "cell line," and "cell culture" may be used interchangeably. All of these terms also include their progeny, which includes any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Numerous expression systems exist that comprise at least a part or all of the compositions discussed above. Prokaryote- and/or eukaryote-based systems can be employed for use with the present disclosure to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE® COMPLETE CONTROL™ Inducible Mammalian Expression System, which involves a synthetic ecdysone-inducible receptor, or its pET Expression System, an E. coli expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

2. Chemical Synthesis

In certain aspects, it will be advantageous to produce peptides using solid-phase synthetic techniques. Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the disclosure are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the 20 standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a post-translational modification of proline.

C. Fusion Proteins

Fusion proteins are created by a head-to-tail linking of two proteinaceous molecules such that peptide sequences not normally found together in nature are joined in a single protein chain. These may be entire molecules, or domains derived from larger sequences. The joining may be mechanical, as where a "linker" molecule is just to connect the two proteins/domains, or genetically, where coding sequences for the proteins/domains are fused at the DNA level and a single transcript and protein product are synthesis.

hIntL-1 shares some sequence homology with the ficolin lectins. Ficolin proteins, along with other examples like mannan-binding lectin (NCBI mRNA RefSeq NM_000242), have an additional domain outside of their carbohydrate recognition domain that allows them to activate human complement for cell killing. This domain is usually located N-terminal of the carbohydrate recognition domain and is easy to recognize because of the presence of a collagen-like domain. hIntL-1 lacks this domain.

The inventors propose the fusion of ficolin and mannan-binding lectin complement activation domains onto the N-terminus of hIntL-1 to create a new molecule able to recognize cells and to kill them. These proteins have several advantages in that they are already human proteins and will likely be well tolerated by the human immune system. A variety of examples of such fusion proteins are provided in FIGS. 20-24. These molecules may optionally include a Strep-tagII or other similar motif for use for purification (not shown). Another type of fusion appends peptide sequences to the N-terminus of hIntL-1 that can target the protein to specific cell types (see FIG. 19). One example is polypeptide chains that target CD3, which are engineered antibody Fab sequences bind to CD3 with nanomolar affinity.

D. Linkers

Linkers or cross-linking agents may be used to fuse peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

Another use of linkers in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge the physically constrains the peptide into its native α-helical shape. In addition to helping retain the native structure needed to interact with a target molecule, this conformation also provides stability against peptidases as well as cell-permeating properties. U.S. Pat. Nos. 7,192,713 and 7,183,059, describing this technology, are hereby incorporated by reference. See also Schafmeister et al. (2000).

E. Modifications, Variants and Analogs

The inventors also contemplate that variants of the sequences may be employed. For example, certain natural and non-natural amino acids that satisfy the structural constraints of native sequences may be used to replace a native residue without a loss, and perhaps with an improvement in, biological function. In addition, the present inventors also contemplate that structurally similar compounds may be formulated to mimic the key portions of peptide or polypeptides of the present disclosure. Such compounds, which may be termed peptidomimetics, may be used in the same manner as the peptides of the disclosure and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

As used herein, "molecular modeling" means quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. Computer programs that use X-ray crystallography data are particularly useful for designing such compounds. Programs such as RasMol, for example, can be used to generate three dimensional models. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. The methods can involve the additional step of outputting to an output device a model of the 3-D structure of the compound. In addition, the 3-D data of candidate compounds can be compared to a computer database of, for example, 3-D structures. Compounds of the disclosure also may be interactively designed from structural information of the compounds described herein using other structure-based design/modeling techniques (see, e.g., Jackson, 1997; Jones et al., 1996). Candidate compounds can then be tested in standard assays familiar to those skilled in the art. Exemplary assays are described herein.

Also of interest are peptidomimetic compounds that are designed based upon the amino acid sequences of compounds of the disclosure. Peptidomimetic compounds are synthetic compounds having a three-dimensional conformation "motif" that is substantially the same as the three-dimensional conformation of a selected peptide. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Polypeptides may be modified for in vivo use by the addition, at the amino- and/or carboxyl-terminal ends, of a blocking agent to facilitate survival of the polypeptide in vivo. This can be useful in those situations in which the polypeptide termini tend to be degraded by proteases. Such blocking agents can include, without limitation, additional related or unrelated sequences that can be attached to the amino and/or carboxyl terminal residues of the peptide to be administered. These agents can be introduced by recombinant DNA technology using methods familiar in the art. Alternatively, blocking agents such as pyroglutamic acid or other molecules known in the art can be attached to the amino- and/or carboxyl-terminal residues.

It may also be useful to include "tags" in polypeptides of the present disclosure. Such tags may permit purification of the polypeptides, and include biotin, Strep-tag, or 6xHis tags. The tages may also permit identification of the molecule through the use of an agent that recognizes the tag. Polypeptides may also be "labeled" with a detectable label, such as a fluorescent moiety, a chemiluminescent moiety, a dye, a radiolabel, a chromophore, a bioluminescent moiety, a nanoparticle and/or bead.

IV. METHODS OF PROMOTING THE MICROBIOME

A. Therapeutic Regimens and Pharmacologic Preparations

The present disclosure contemplates the provision of intelectin polypeptides to a subject. The provision may be in the context of treating a particular disorder, or instead, it may be a generalized treatment to sustain, improve, enhance, stabilize or protect the microbiome in the subject. Where such clinical applications are contemplated, pharmaceutical compositions will be prepared in a form appropriate for the intended application. Generally, this will entail preparing compositions that are essentially free of pyrogens, as well as other impurities that could be harmful to humans or animals.

In particular embodiments, the delivery may involve delivery the intelectins themselves in a variety of classical pharmaceutical formulations and probiotic formulations. Alternatively, recombinantly engineered cells (e.g., a probiotic organism discussed above, or a non-pathogenic organism such as *Pichia pistoris*) may encode a gene for an intelectin and express and secrete the polypeptide once delivered to the subject.

One will generally desire to employ appropriate salts and buffers to stabilize the formulation. Aqueous compositions of the present disclosure comprise an effective amount of polypeptide, dissolved or dispersed in a pharmaceutically acceptable carrier or aqueous medium. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present disclosure, its use in therapeutic compositions is contemplated. Supplementary active ingredients also can be incorporated into the compositions, provided they do not inactivate the vectors or cells of the compositions.

The active compositions of the present disclosure may include classic pharmaceutical preparations. Administration of these compositions according to the present disclosure may be via any common route so long as the target tissue is available via that route. This includes oral, nasal, rectal, vaginal, topical or buccal. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms may be provided as aqueous solutions or dispersions and powders for the extemporaneous preparation of solutions or dispersions. Preparations should be stable under the conditions of manufacture and storage. Appropriate solvents or dispersion media may contain, for example, water, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. In many cases, it will be preferable to include isotonic agents, for example, sugars or sodium chloride. In the case of powders for the preparation of solutions, the preferred methods of preparation include vacuum-drying and freeze-drying techniques which yield a powder of the active ingredient(s) plus any additional desired ingredient from a previously sterile-filtered solution thereof.

For oral administration the polypeptides of the present disclosure generally may be incorporated with excipients typically used in foodstuffs and probiotic formulations, which are discussed below.

The compositions of the present disclosure generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective, i.e., to achieve one of the above-stated goals. The formulations may easily be administered in a variety of dosage forms such as solutions, capsules, tablets, douches, and the like. By way of illustration, a single dose may be dissolved in 1 ml of isotonic NaCl solution and either added to 1000 ml of hypodermoclysis fluid at the proposed site (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet pyrogenicity, general safety, and purity standards as required by FDA Office of Biologics standards.

B. Foodstuffs

Probiotic polypeptides may advantageously be incorporated into a comestible food directly ingestible by a user, i.e., foodstuffs, such as nutrient supplements, health drinks and probiotic foods. Generally, the components of the various types of food formulations will be conventional, although precise amounts of individual components and the presence of some of the conventional components may well be unconventional in a given formulation.

The food product may be a cooked product. It may incorporate meat or animal-derived material (such as beef, chicken, turkey, lamb, fish, blood plasma, marrowbone, etc or one or more thereof). The product alternative may be meat-free (preferably including a meat substitute such as soya, maize gluten or a soya product) in order to provide a protein source. The product may contain additional protein sources such as soya protein concentrate, milk, protein, gluten, etc. The product may also contain a starch source such as one or more grains (e.g., wheat, corn, rice, oats, barley, etc.) or may be starch-free. The product may incorporate or be a gelatinized starch matrix. The product may incorporate one or more types of fiber such as sugar beet pulp, chicory pulp, chicory, coconut endosperm fiber, wheat fiber, etc. Dairy products may be suitable.

For many foods, it is accepted practice for the user to add the required amount of eggs in the course of preparation and this practice may be followed just as well herein. If desired, however, the inclusion of egg solids, in particular, egg albumen and dried yolk, in the food are allowable alternatives. Soy isolates may also be used herein in place of the egg albumen.

Dry or liquid flavoring agents may be added to the formulation. These include cocoa, vanilla, chocolate, coconut, peppermint, pineapple, cherry, nuts, spices, salts, flavor enhancers, among others. Acidulants commonly added to foods include lactic acid, citric acid, tartaric acid, malic acid, acetic acid, phosphoric acid, and hydrochloric acid.

Other added agents may include anti-oxidants, pH buffers, flavor masking agents, odor masking agents, preservatives, timed-release mechanisms, vitamins, minerals, electrolytes, hormones, herbal material, botanicals, amino acids, carbohydrates, fats, or the like.

V. PURIFICATION OF PEPTIDES/PROTEINS

It will be desirable to purify peptides and polypeptides according to the present disclosure. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present disclosure concern the purification, and in particular embodiments the substantial purification, of a protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High performance liquid chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of non-antibody proteins that recognize carbohydrate epitopes of polysaccharides and glycoproteins. Lectins can be coupled to agarose by cyanogen bromide to generate affinity resins. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present disclosure is discussed below.

A particular embodiment that can be employed with intelectins is purification using affinity to carbohydrates. Specifically for hIntL-1, linear carbohydrates (specifically sorbitol), or other carbohydrates that contain an exocyclic diol (like β-galactofuranose), can be immobilized on a resin. The terminal exocyclic diol on most linear carbohydrates is an excellent ligand for intelectins, so when they are immobilized on a resin, they capture intelectins in a calcium ion dependent manner. They can be eluted by EDTA or the addition of excess exocyclic diol containing compounds (such as glycerol or sorbitol). This has been demonstrated with a galactofuranose and a sorbitol column, but other carbohydrate ligands function as well. In a particular aspect, the inventors use sorbitol that is immobilized on a sepharose resin through divinyl sulfone chemistry. Divinyl sulfone chemistry for carbohydrate resins is well established.

VI. EXAMPLES

The following examples are included to further illustrate various aspects of the disclosure. It should be appreciated by those of skill in the art that the techniques disclosed in the examples which follow represent techniques and/or compositions discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Clustal W Alignment.

Intelectin and ficolin proteins were selected for Clustal W analysis using MegAlign in the Lasergene 8 Suite (DNASTAR). Intelectins include human intelectin-1 (hIntL-1), accession no. Q8WWA0; human intelectin-2 (hIntL-2), Q8WWU7; mouse intelectin-1 (mIntL-1), O88310; mouse intelectin-2 (mIntL-2), Q80ZA0; sheep intelectin-1 (sIntL-1), Q3LAF 5; *Xenopus laevis* intelectin-1 (XIntL-1), Q5PPM0; human H-ficolin (h H-ficolin), O75636; human L-ficolin (h_L-ficolin), Q15485; human M-ficolin (h_M-ficolin), O00602. Proteins were aligned using the default Clustal W Method parameters on the slow and accurate mode.

Native Human Intelectin-1 Expression and Purification.

The cDNA for hIntL-1 (Accession Number: NM_017625) was obtained from Open Biosystems Clone LIFESEQ2924416 as a glycerol stock (GE Healthcare). The full coding sequence, residues 1-313, were amplified using PRC with the forward primer 5'-CGTGGGATCCTG-GAGGGAGGGAGTGAAGGAGC-3' (SEQ ID NO: 1) and the reverse primer 5'-GCCAGCTCGAGACCT-TGGGATCTCATGGTTGGGAGG-3' (SEQ ID NO: 2). The primers installed restriction endonuclease sites for BamHI and XhoI, respectively. The doubly digested hIntL-1 PCR fragment was ligated into a doubly digested pcDNA4/myc-HisA vector backbone (Life Technologies). Correct insertion was confirmed with DNA sequencing (UW-Madison Biotechnology Center).

hIntL-1 was expressed via transient transfection of suspension adapted HEK 293T cells. Cells were transfected in Opti-mem I Reduced Serum Medium (Life Technologies) at ~2×10$^6$ cells/mL using Lipofectamine 2000 (Life Technologies), according to the manufacturers protocol. Six hours post transfection, the culture medium was changed to Free-Style F17 expression medium (Life Technologies) supplemented with 50 U/mL penicillin-streptomycin, 4 mM L-glutamine, 1× nonessential amino acids, 0.1% fetal bovine serum and 0.1% Pluronic F-68 (Life Technologies). Cells were left to express hIntL-1 for up to 6 days, or until viability decreased below 60%, at which point the conditioned expression medium was harvest by centrifugation and sterile filtration.

Conditioned media was adjusted to pH=7.4 by slow addition of 0.1 M NaOH and CaCl$_2$ was added to 10 mM. hIntL-1 was purified by binding to a β-Galf column generated from reaction of Compound 51, an amine functionalized β-Galf, and UltraLink Biosupport (Piere). Resin was washed with 20 mM HEPES (7.4) 150 mM NaCl and 10 mM CaCl$_2$. hIntL-1 was eluted with addition of 20 mM HEPES (7.4) 150 mM NaCl and 10 mM EDTA and concentrated using a 10,000 MWCO Amicon Ultra Centrifugal Filter. Buffer was exchanged to 20 mM HEPES (7.4) 150 mM NaCl and 1 mM EDTA. Protein purity was assessed by SDS-PAGE electrophoresis and coomassie blue staining, and was often >95%. The concentration of hIntL-1 was determined using absorbance at 280 nm with a calculated $\varepsilon = 237{,}4000$ cm$^{-1}$M$^{-1}$ for the trimer, and an estimated trimer molecular mass of 101,400 Da (to account for glycosylation). Typical yields from a 30 mL transfection were 400 µg.

hIntL-1 Carbohydrate Binding ELISA-Like Assay.

To fabricate carbohydrate-displaying surfaces, 0.5 µg of streptavidin (Prozyme, cat. no. SA20) was adsorbed onto a Maxisorp (Nunc) flat bottom 96 well plate in PBS. Wells were washed with PBS and then coated with 5 µM of carbohydrate-biotin ligand in PBS for 1 hour at 22° C. Wells were blocked with bovine serum albumin (BSA) in ELISA buffer (20 mM HEPES (7.4) 150 mM NaCl, 10 mM CaCl$_2$, and 0.1% tween-20). Samples containing hIntL-1 were prepared by serial dilution into ELISA buffer+0.1% BSA and added to wells for 2 hours at 22° C. Wells were washed four times with ELISA buffer. Bound hIntL-1 was detected using 0.75 µg/mL of a sheep IgG hIntL-1 antibody (R&D Systems, cat. no. AF4254) in ELISA buffer+0.1% BSA for 2 hours at 22° C. Wells were washed with ELISA buffer. A donkey anti-sheep IgG horseradish peroxidase (HRP) conjugate (Jackson ImmunoResearch Laboratories) was added at a 1:5,000 dilution in ELISA buffer+0.1% BSA for 1 hour at 22° C. Wells were washed and hIntL-1 was detected colorimetrically with addition of 1-Step Ultra TMB-ELISA (Pierce). Once sufficient signal was achieved (typically <2 min.), the reaction was quenched with addition of equal volume 2 M H$_2$SO$_4$. Plates were read at 450 nm on an ELx800 plate reader (Bio-Tek). When testing the Ca$^{2+}$ dependency of hIntL-1, 1 mM EDTA replaced 10 mM CaCl$_2$ in all steps. Data were analyzed on Prism6 (GraphPad). Data were fit to the one site-specific binding equation.

hIntL-1 Surface Plasmon Resonance (SPR).

All hIntL-1 SPR was performed on a ProteOn XPR36 (Bio-Rad) at the University of Wisconsin-Madison Department of Biochemistry Biophysics Instrumentation Facility (BIF). To measure hIntL-1 binding, ProteOn NLC sensor chips (Bio-Rad) (NeutrAvidin coated chips) were used to capture carbohydrate-biotin ligand. All experiments presented here were conducted at surface saturated levels of ligand, ~200 RU. In all experiments, captured biotin served as a control. Samples containing purified hIntL-1 were prepared by serial dilution into hIntL-1 SPR running buffer (20 mM HEPES (7.4) 150 mM NaCl, 1 mM CaCl$_2$, and 0.005% tween-20). Surfaces were regenerated with short injections of 10 mM HCl. All data was interspot corrected and processed using the Bio-Rad ProteOn software package.

Expression and Purification of *Xenopus laevis* Strep-tagII Intelectin-1.

The cDNA for *Xenopus laevis* i ntelectin-1 (XIntL-1) (accession number NM_001089101). An N-terminal Strep-Tag® II was cloned into the hItnL-1::pcDNA4 vector using site-directed mutagenesis and a primer set comprised of 5'-ACCACCAGAGGATGGAGTACAGATTGGAGC-CATCCGCAGTTT GAAAAGTCTACAGATGAGGCTAATACTTACT-TCAAGGA-3' (SEQ ID NO: 3) and its reverse complement. The correct insertion was confirmed with DNA sequencing. Strep-hIntL-1 was expressed identically to hIntL-1. For purification, conditioned Strep-hIntL-1 medium was adjusted to pH=7.4 using NaOH, avidin was added per the IBA GmbH protocol (IBA GmbH, cat. no. 2-0205-050), CaCl$_2$) was added to 10 mM, and the solution was cleared with centrifugation (15,000 g for 15 minutes). Protein was captured onto 2 mL of Strep-Tactin Superflow resin (IBA GmbH, cat. no. 2-1206-002). The resulting resin was washed with a solution of 20 mM HEPES (7.4), 150 mM NaCl, and 10 mM CaCl$_2$) and then 20 mM HEPES (7.4), 150 mM NaCl, and 1 mM EDTA. The protein was eluted with 5 mM d-desthiobiotin (Sigma) in 20 mM HEPES (7.4), 150 mM NaCl, and 1 mM EDTA and concentrated using a 10,000 MWCO Amicon Ultra Centrifugal Filter. The concentration of Strep-hIntL-1 was determined using absorbance at 280 nm with a calculated $\varepsilon = 237{,}400$ cm-1M-1 for the trimer, and an estimated trimer molecular mass of 101,400 Da. Typical yields were similar to what was measured with untagged hIntL-1.

For protein x-ray crystallography, Strep-hIntL-1 was purified following culture medium dialysis against 20 mM BIS-TRIS (6.7), 150 mM NaCl, and 1 mM EDTA. The pH of the culture medium was adjusted to 6.7, avidin was added per the IBA GmbH protocol, CaCl$_2$ was added to 10 mM and the solution was cleared with centrifugation. Protein was purified by capture onto Strep-Tactin Superflow resin. Resin was washed with 20 mM BIS-TRIS (6.7), 150 mM NaCl, 10 mM CaCl$_2$ and then 20 mM BIS-TRIS (6.7), 150 mM NaCl, 0.5 mM EDTA. Protein was eluted with 5 mM d-desthiobiotin (Sigma) in 20 mM BIS-TRIS (6.7), 150 mM NaCl, 0.5 mM EDTA and concentrated using a 10,000 MWCO Amicon Ultra Centrifugal Filter.

Construction of the Furanoside Glycan Array.

The microarray of furanoside containing glycans was printed as previously described. Briefly, the amine functionalized glycans shown in FIG. 10A were dissolved in 100 mM sodium phosphate (8.0) and printed as 14 arrays on N-hydroxysuccinimidyl (NETS) ester-activated slides (Shott Nexterion, Louisville, Ky.). Arrays were printed in replicates of n=4 at different glycan concentrations (as indicated in FIG. 10B) using a Piezorray printer (Perkin Elmer, Waltham, Mass.) that delivered 0.33 nL per spot. The 2-amino(N-aminoethyl) benzamine (AEAB) derivatives of lacto-N-neotetraose (LNnT) and asialo, galactosylated bi-antennary N-linked glycan (NA2) were printed as controls to confirm glycan immobilization. After printing, covalent coupling of glycans to the surface was facilitated by incubation at 55° C. in an atmosphere of >80% humidity for 1 hour. Slides were dried in a desiccator overnight and blocked using a solution of 50 mM ethanolamine in 50 mM borate buffer (8.0). Prior to interrogating with glycan binding proteins (GBPs), the arrays are rehydrated in binding buffer.

Assay of hIntL-1 on Furanoside and CFG Mammalian Glycan Array.

GBPs at various concentrations were applied to separate furanoside arrays in 70 µL of binding buffer (20 mM HEPES (7.4), 150 mM NaCl, 1 mM EDTA, 10 mM $CaCl_2$, 1% BSA and 0.05% Tween-20) in the wells formed on the slide with a silicon grid (14 wells per slide). After incubation for 1 hr at RT, the slides were washed with wash buffer (20 mM HEPES (7.4), 150 mM NaCl, 1 mM EDTA and 10 mM $CaCl_2$, 0.05% Tween-20). The biotinylated lectins *Erythrina cristagalli* lectin (ECL) and *Ricinus communis* agglutinin I lectin (RCAI) were detected using Alexa Fluor® 488-labeled streptavidin (10 µg/ml) in binding buffer (FIGS. 10C and D). hIntL-1 was detected with a sheep polyclonal IgG antibody specific for hIntL-1 (5 µg/ml) (R&D Systems) and an Alexa Fluor® 488-labeled donkey anti-sheep IgG secondary antibody (5 µg/ml) (Life Technologies). Bound protein was detected using a ProScanArray Scanner (Perkin Elmer) equipped with 4 lasers covering an excitation range from 488 to 633 nm. The data from the furanoside glycan array were analyzed with the ScanArray Express software (Perkin Elmer) as the average of the 4 replicates.

For the analysis of the CFG glycan array (Blixt et al., 2004), hIntL-1 was applied in 70 µl at a concentration of 50 and 200 µg/ml in binding buffer under a coverslip to distribute the solution evenly over the large array of 610 glycans printed in replicates of n=6 (Array v5.1). After washing and scanning, the data from the CFG glycan microarray were analyzed using ImaGene software (BioDiscovery, Hawthorne, Calif.) as the average of 4 values after removing the high and low values of the 6 replicates. With both the furanoside and mammalian glycan array, the images were converted to Excel files, and the data are reported as histograms of average Relative Fluorescence Units (RFU) versus print identification number that identified the glycan targets. Figures were made using Prism6 (GraphPad) or Excel (Microsoft).

Assay of hIntL-1 on the Bacterial Glycan Array.

Strep-hIntL-1 was used to interrogate the Microbial Glycan Microarray version 2 (MGMv2). Construction of the MGMv2 is previously described. Briefly, bacterial polysaccharide samples were dissolved and diluted to 0.5 mg/mL in printing buffer (150 mM sodium phosphate buffer (8.4)+ 0.005% Tween-20). Samples were immobilized on NETS-activated glass slides (SlideH, Schott/Nexterion) using a MicroGrid II (Digilab) contact microarray printer equipped with SMP-4B printing pins (Telechem). Six replicates of each bacterial glycan sample were printed. Covalent coupling of glycans to the surface was facilitated by incubation for 1 hour postprint at 100% relative humidity. The remaining reactive NHS-moieties were quenched using a blocking solution (50 mM ethanolamine in 50 mM borate buffer (9.2)). Blocked slides were stored at −20° C. until assays were performed. To interrogate the MGMv2, Strep-hIntL-1 was diluted to 50 µg/mL in binding buffer (20 mM Tris-HCl (7.4), 150 mM NaCl, 2 mM $CaCl_2$, 2 mM magnesium chloride ($MgCl_2$) 1% BSA, and 0.05% Tween-20) and applied directly to the array surface for 1 hour. Following incubation, the array was washed by dipping into binding buffer four times. The Strep-Tag® II on bound hIntL-1 was detected using StrepMAB-Classic Chromeo647 (10 µg/mL, IBA GmbH Lifesciences) diluted in binding buffer applied directly to the array surface and allowed to incubate for 1 hour. The array was washed in binding buffer (4 dips), binding buffer minus BSA and Tween-20 (4 dips) and de-ionized water (4 dips). Finally, the array was dried by centrifugation and scanned. Interrogated arrays were scanned for Chromeo647 signal using a ProScanArray Express scanner (Perkin Elmer) and resultant images were processed to extract signal data using Imagene (v6.0, Biodiscovery). Signal data was calculated as the average of 4 values after removing the high and low values of the 6 replicates. Data were plotted using Excel (Microsoft) as average Relative Fluorescence Units (RFU) versus print identification number. Figures were made using Prism6 (GraphPad).

Protein X-Ray Crystallography.

The Strep-hIntL-1 protein that was purified using 20 mM BIS-TRIS (6.7) buffers was concentrated to 1.5 mg/mL and crystallization (hanging-drop vapor-diffusion) was achieved by mixing 1 µL of the protein solution and 1 µL of well solution (100 mM BIS-TRIS (6.0) and 25% PEG 3350). Crystals grew to full size in two weeks. Protein crystals of Apo-hIntL-1 were cryoprotected via transfer to well solution supplemented with 35% PEG 3350 for one minute and then vitrified in liquid nitrogen. The allyl-β-Galf-hIntL-1 complex was formed by soaking apohIntL-1 crystals in cryoprotection solution supplemented with 50 mM allyl-β-D-galactofuranose for two weeks.

Single crystal X-ray diffraction experiments were performed at beamline 21-ID-D (Life Sciences Collaborative Access Team, LS-CAT), Advanced Photon Source, Argonne National Laboratory. Integration, scaling, and merging were performed with HKL2000. The structure was solved using the PHENIX suite. The *Xenopus laevis* intelectin structure recently solved in the inventors' lab was used as a search model to determine the structure of apo-hIntL-1 by molecular replacement using Phase r. Because the apo-hIntL-1 and β-Galf-bound hIntL-1 data are isomorphous, the structure of β-Galf-bound hIntL-1 was solved by a difference Fourier method using apo-hIntL-1 as a starting model for rigid-body refinement with phenix.refine. The chemical restraint for β-Galf was generated by PRODRG. Model adjustment and refinement were performed in Coot and phenix.refine, respectively. The model was validated using MolProbity. Crystal structure figures were generated with PyMOL.

XIntL-1 was expressed as a secreted protein in High Five cells (Life Technologies), a derivative of *Trichopulsia ni*, by the addition of 0.5 µL of baculovirus conditioned medium per $1 \times 10^6$ viable cells. For selenomethione labeled XIntL-1 used for phasing, High Five cells were suspension cultured in 921 Delta Series, Methionine Deficient medium (Expression Systems, cat. no. 96-200) supplemented with 1× antibiotic-antimycotic (Life Technologies) and 10 µg/mL gentamicin (Life Technologies). Expression was induced when cells reached a density $\geq 2 \times 10^6$ cells/mL by the addition of 0.5 µL of baculovirus conditioned media per $1 \times 10^6$ viable cells. L-selenomethionine (Acros Organics) was dissolved in water at 10 mg/mL and sterile filtered. The first addition of selenomethionine was 10 mgs at 12 hours post infection, 10 additional mgs were added every 24 hours up until medium harvest. No significant toxicity or growth defect was observed. Cells were allowed to express XIntL-1 for 5 days at 22° C. in a baffled flask shaking at 90 RPM. Conditioned culture medium was harvest by centrifugation and filtration through a 0.22 µM filter unit, the media was stored at 4° C. for at least one week. Conditioned media was dialyzed extensively against 20 mM bis-tris (6.7), 150 mM NaCl, and 1 mM EDTA. The media was slowly adjusted to pH=6.7, $CaCl_2$ was added 10 mM, 4 µL of 7 mg/mL avidin (Calbiochem) per mL of conditioned media was added to absorb excess biotin, and the solution was cleared by centrifugation. Strep-tagII XIntL-1 was purified by binding to Strep-Tactin Superflow resin (IBA GmbH, cat. no. 2-1206-002). The column was washed with 20 mM bis-tris (6.7), 150 mM NaCl, 10 mM $CaCl_2$ and then 20 mM bis-tris (6.7), 150 mM NaCl, 0.5 mM EDTA. Protein was eluted with 5 mM d-desthiobiotin (Sigma) in 20 mM bis-tris (6.7), 150 mM NaCl, 0.5 mM EDTA and concentrated using a 10,000 MWCO Amicon Ultra Centrifugal Filter. During the concentration process, large sheet-like crystals began to form. Crystals were harvested by centrifugation at 2,000 RPM and washed 2 times using 20 mM bis-tris (6.7), 150 mM NaCl, 0.5 mM EDTA. The crystals were resuspended in 20 mM bis-tris (6.7), 150 mM NaCl, 0.5 mM EDTA and $CaCl_2$ was added to 5 mM. Within one minute, the crystals completely redissolved. Protein purity of the redissolved crystals was assessed by SDS-PAGE electrophoresis and coomassie blue staining and was >95%. The concentration of XIntL-1 was determined using absorbance at 280 nm with an estimated $\varepsilon=75,455$ $cm^{-1}M^{-1}$ for the monomer and a calculated molecular mass of 36,258 Da, post signal peptide removal. Typical yields were 0.5 mg per 50 mL of conditioned media. Selenomethionine incorporation was assessed using electrospray ionization mass spectrometry (UW-Madison Biotechnology Center).

Expression and Purification of Strep-tagII hIntL-1 for Crystallography.

An N-terminal Strep-tag II was cloned into the hItnL-1::pcDNA4 vector using site-directed mutagenesis and the primer set 5'-accaccagaggatggagtacagattggagccatccgcagttt-gaaaagtctacagatgaggctaatacttacttcaagga-3' (SEQ ID NO: 3) and its reverse complement. The correct insertion was confirmed with DNA sequencing. Strep-hIntL-1 was expressed identically to hIntL-1 expression. Strep-hIntL-1 was purified following culture medium dialysis against 20 mM bis-tris (6.7), 150 mM NaCl, and 1 mM EDTA. The pH of the culture media was adjusted to 6.7, avidin was added per the IBA GmbH protocol, $CaCl_2$) was added to 10 mM and the solution was cleared with centrifugation. Protein was purified by capture onto Strep-Tactin Superflow resin. Resin was washed with 20 mM bis-tris (6.7), 150 mM NaCl, 10 mM $CaCl_2$) and then 20 mM bis-tris (6.7), 150 mM NaCl, 0.5 mM EDTA. Protein was eluted with 5 mM d-desthiobiotin (Sigma) in 20 mM bis-tris (6.7), 150 mM NaCl, 0.5 mM EDTA and concentrated using a 10,000 MWCO Amicon Ultra Centrifugal Filter. Typical yields were similar to what was measured with untagged hIntL-1.

Commercially Available and Previously Characterized Compounds Used in this Study.

The α-N-acetyl-neuraminic acid-biotin ligand used in this study was purchased from GlycoTech (Gaithersburg, Md.; cat. no. 02-012). Glycerol phosphate was purchased from Sigma Aldrich (Milwaukee, Wis.: cat. no. G7886). The 2-O-methyl-N-acetyl-α-neuraminic acid was purchased from Toronto Research Chemicals (North York, ON, Canada; cat. no. M275400). The synthesis of the α-rhamnose-biotin ligand has been described previously.

Example 2—Results

The investigators were interested in the specific recognition of nonhuman glycans by hIntL-1. A lectin specific for Galf would be an invaluable tool for detecting galactofuranosylated biomolecules in complex mixtures. Previous researchers have explored the carbohydrate-binding specificity of intelectin proteins, although a general trend of ligand preferences could not be determined (Tsuji et al., 2001). The difficulty of accurately determining the carbohydrate preferences of hIntL-1 likely resulted from their use of soluble monosaccharides with a free reducing end as competitors. The presence of a free reducing end, as opposed to a glycoside, results in a mixture of linear and various ring closed isomers. As a result, the precise molecules that compete for intelectin binding with an immobilized polysaccharide were unclear from previous experiments. The investigators first established a robust expression and purification strategy for hIntL-1. Based on the intra- and intermolecular disulfide bonds and reported N-glycosylation, they chose a HEK293-T based mammalian transient expression system. Transfection of suspension cells yields high amounts of properly folded disulfide-linked trimeric hIntL-1. For initial characterization, hIntL-1 was purified by exploiting its carbohydrate binding activity to an immobilized β-Galf agarose column (FIGS. 7A-B). Previous to this successful purification strategy, the investigators attempted unsuccessfully to purify hIntL-1 using an immobilized galactopyranose and an immobilized β-ribofuranose column. This was their first indication that hIntL-1 bound Galf.

Figure 9:
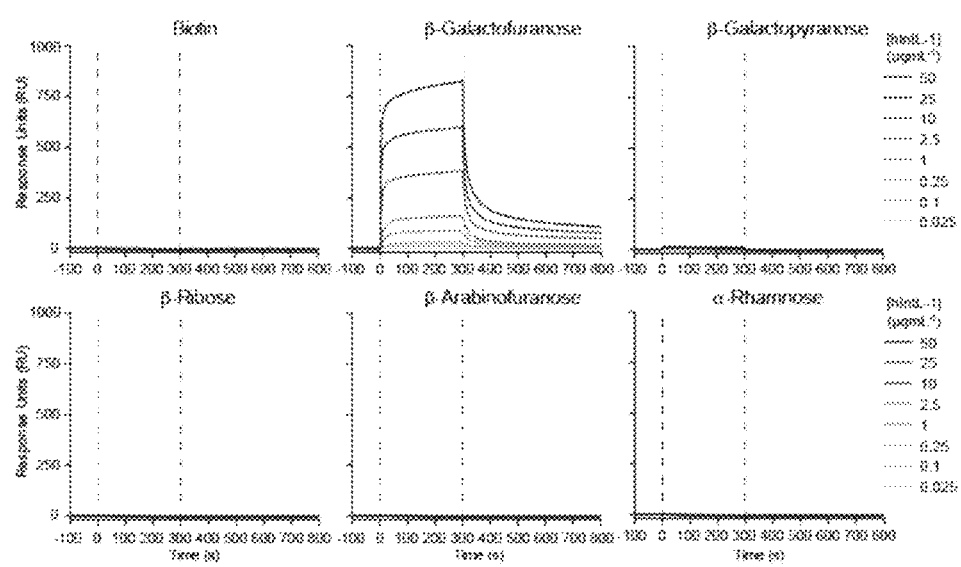
FIG. 9. SPR analysis of hIntL-1. Complete data set of hIntL-1 SPR analysis presented in FIG. 1*d*. No binding to an immobilized carbohydrate is observed other than robust binding to β-Galf. β-Ribofuranose and β-arabinofuranose were included as they were reported to be ligands of hIntL-1 (cite). β-Rhamnose was included as it is a non-human monosaccharide. Data was injection and baseline aligned using the Bio-Rad ProteOn software. Data is interspot corrected.
Figure 16A:
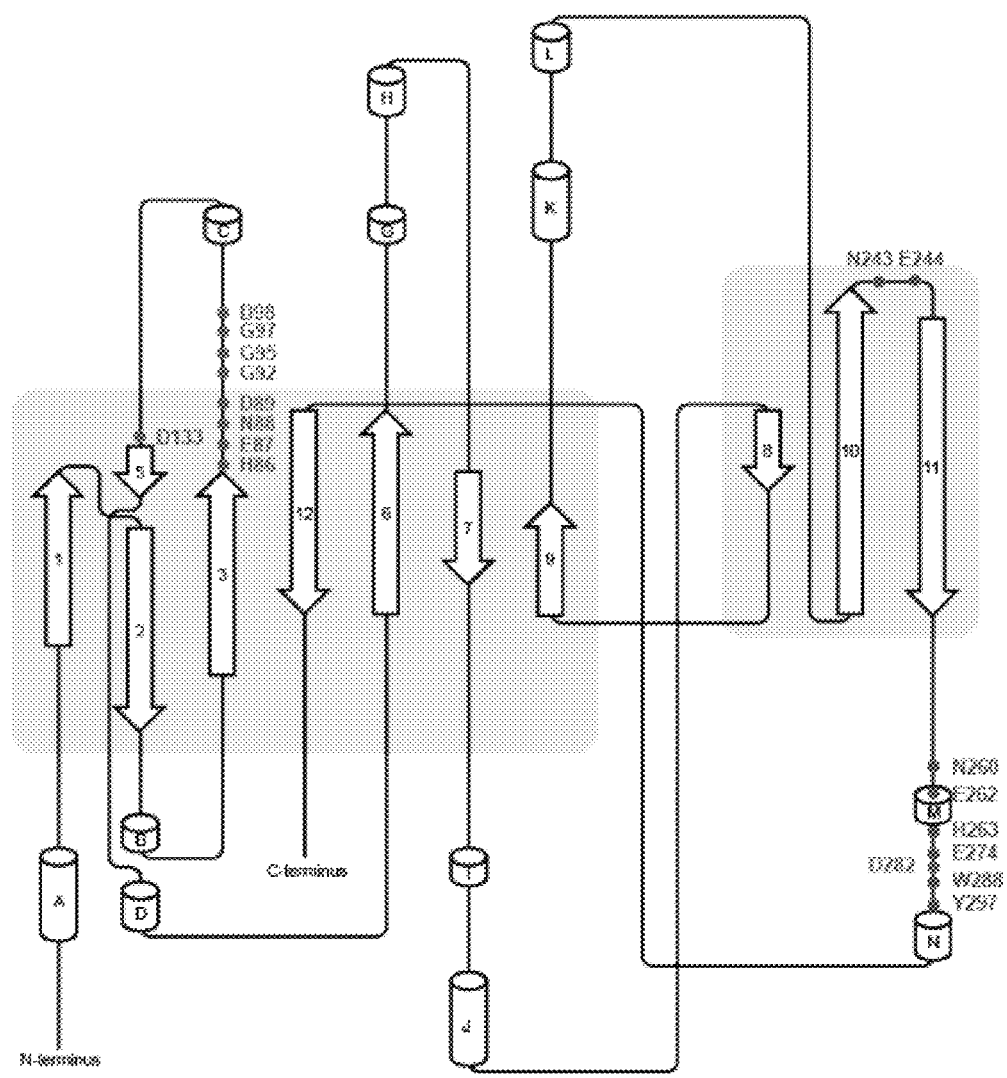
FIGS. 16A-B. Topology diagrams of intelectin proteins.
Figure 16B:
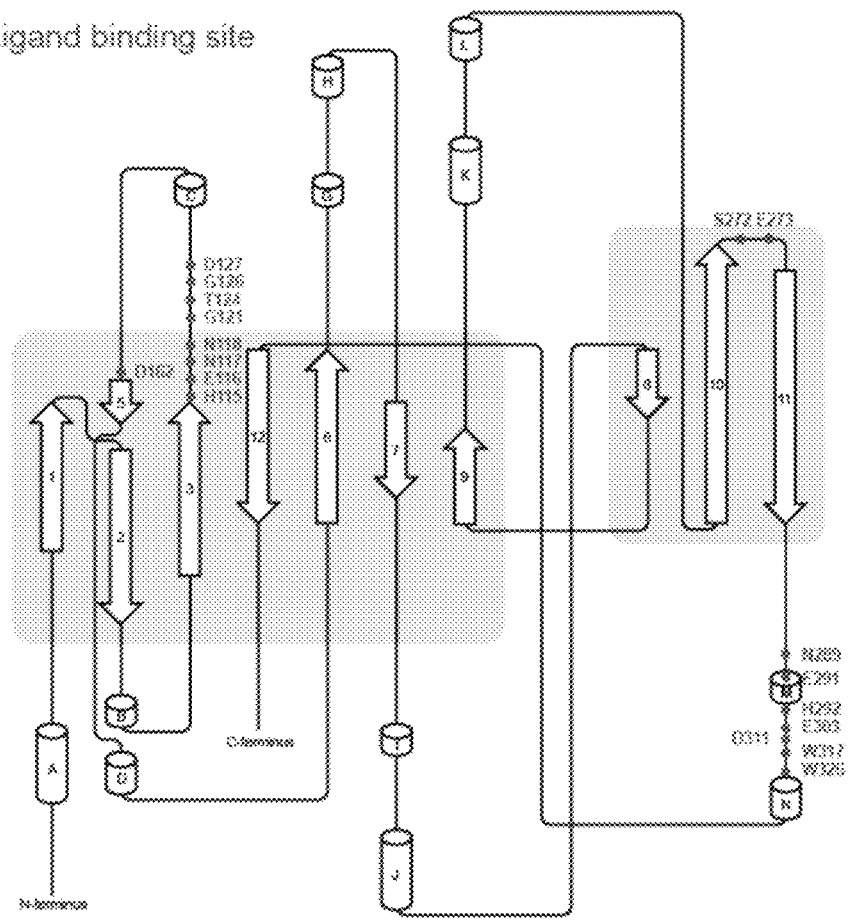

To assess the carbohydrate binding activity of recombinant hIntL-1, the investigators employed biotinylated carbohydrates and an enzyme-linked immunoabsorbent (ELISA) like assay (FIGS. 1A and 8A-B). Using this assay, the investigators show that trimeric hIntL-1 binds immobilized β-Galf with an avidity of 85±14 nM (FIGS. 1B-C). Unlike previous reports, these results reveal that hIntL-1 is exceptionally specific for Galf as binding to other immobilized carbohydrate ligands was not detected. To further probe the ligand specificity of hIntL-1, the investigators chose to investigate binding using surface plasmon resonance (SPR). The results of this ELISA suggested specific binding to β-Galf, but ELISAs are dependent on the dissociation kinetics ($k_d$) of hIntL-1::carbohydrate complexes. The investigators envisioned using SPR as a more biologically relevant assay of lectin binding. In this format, carbohydrate ligands are immobilized in a multivalent display on a cell surface, both lectin and ligand are at steady state concentrations, and ligand binding will be independent of $k_d$. For examining specificity, they added two additional nonhuman glycans; β-arabinofuranose (Araf) and β-rhamnose. Even at concentations 6-fold higher than the β-Galf $K_D$, high specificity of hIntL-1 binding was observed (FIGS. 1D and 9). The small response to immobilized β-galactopyranose (β-Galp) is attributed to the extended anomeric alkyl linker it bears. This SPR result supports the specificity the investigators observed with their ELISA.

Figure 2:
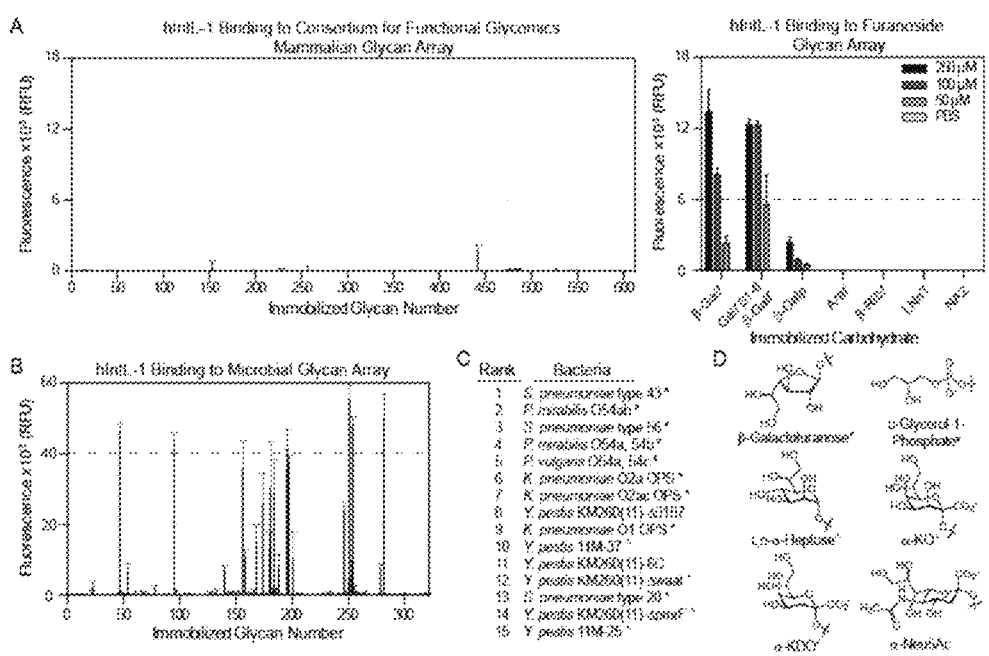
FIGS. 2A-D. hIntL-1 binds microbial glycan epitopes.
Figure 3:
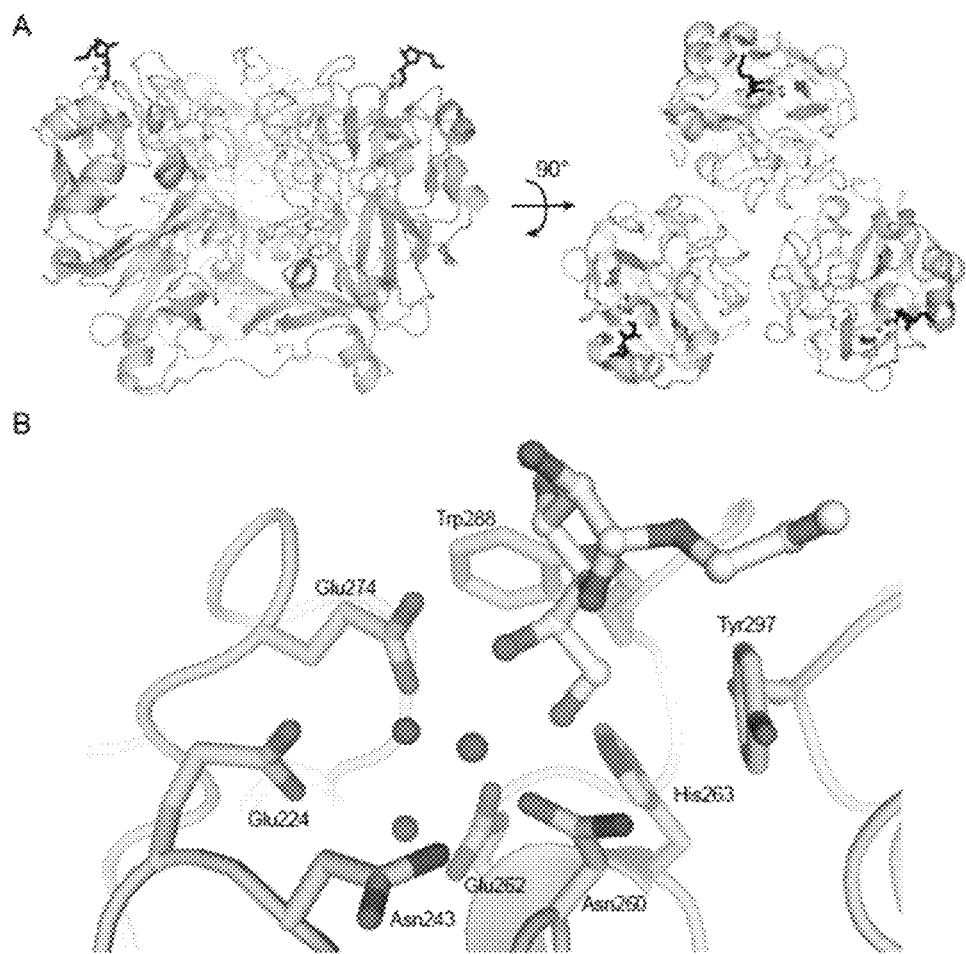
FIGS. 3A-B. Structure of hIntL-1 bound to allyl-β-D-Galf.

Glycan microarray technology has revolutionized the field of glycobiology (Blixt et al., 2004). It enables the high throughput discovery of carbohydrate ligands and simultaneously allows exploration of structure function relationships. Several requests to screen the Consortium for Functional Glycomics (CFG) mammalian glycan array have been made previously (available on the CFG website). An inspection of that data reveals consistently no high affinity ligands. The investigators hypothesized these results stem from a lack of functional hIntL-1 and the lack of a positive control for carbohydrate binding activity. As the investigators had previously demonstrated functionality of hIntL-1, they envisioned using amine-activated carbohydrate ligands to generate a small furanoside array to run as a positive control alongside the mammalian glycan array v5.1 (FIGS. 10A-D). Ligands were immobilized at varying density using standard succinimidyl-ester coupling to a glass overclip. LNnT and NA2 were used as immobilization controls. Similar specificity was measured under the array format for β-Galf as what was observed when using complementary techniques (FIG. 2A). The small furanoside glycan array afforded conditions to screen hIntL-1 on the CFG mammalian glycan array. Using these conditions, no glycans were bound by hIntL-1 to an extent similar to β-Galf on the furanoside array (FIG. 2A). The highest signal came from a disaccharide GalNAcβ1-6GalNAc. The investigators concluded that the putative binding interactions from this array are nonspecific. No general epitope preferences can be inferred, and increasing the hIntL-1 concentration 4-fold identified different ligands with similarly low signal intensity. These data suggest that of the human glycan ligands screen thus far, none are bound by hIntL-1 with appreciable affinity.

In the absence of human-derived glycan ligands for hIntL-1, the investigators turned to the only available, small microbial glycan array (Stowell et al., 2014). Inspection of the glycans immobilized on the microbial array revealed several candidate ligands that contain Galf. When assayed at the same concentration as the previous arrays, 50 µg/mL, several glycans were bound by hIntL-1 (FIG. 2B). The identified ligands include glycans from *Streptococcus pneumonia, Proteus mirabilis, Proteus vulgaris, Klebsiella pneumonia*, and *Yersinia pestis* (FIG. 2C). Of the top 15 glycan ligands for hIntL-1, several contained the β-Galf epitope, including OPS from *Klebsiella* and capsular polysaccharide from *Streptococcus*. Many other ligands, however, lack Galf. Inspection of the chemical structures of each ligand revealed hIntL-1 has an unexpected affinity for terminal D-glycerol-1-phosphate modified glycans and glycans that contained heptose, D-glycero-D-talo-oct-2-ulosonic acid (Ko), or 3-deoxy-D-manno-oct-2-ulosonic acid (Kdo). Each of these glycan modifications share a terminal vicinal diol epitope with the last carbon being nonstereogenic (FIG. 2D). Every characterized ligand from the top 15 hits contains at least one of these terminal epitopes.

Each of the ligands discovered in this array are bacteria-specific glycan epitopes. Earlier the investigators discussed microbial Galf biosynthesis. As with Galf, glycerol modification of glycans is not found in humans. And lastly, heptose, Ko, and Kdo are microbe-specific monosaccharides. Specifically, heptose, Kdo, and Ko are conserved components of gram-negative bacterial lipopolysaccharide (LPS) (Schnaitman & Klena, 1993). It does not appear that hIntL-1 recognizes a single glycan epitope (FIGS. 12A-B). Rather, the vicinal diols present in the ligands identified here comprise allow broad recognition of many microbes. This may explain why LPS derived glycans appear preferentially in the top half of ligands from the microbial glycan array. Despite the apparent simplicity of ligand recognition, other factors such as sterics are involved in binding. For example, the microbial glycan array contains several examples of α-Galf. *S. pneumonia* type 22F (array ligand #238) contains a α-Galf residue with the 5- and 6-hydroxyl free to bind hIntL-1 (FIGS. 12A-B). Inspection of the data reveals this is the 301$^{st}$ ranked ligand on the array, with an average signal of −9.6 RFU. Additional examples of hindered binding to α-Galf include *E. coli* 085 (#295), *Salmonella enterica* O17 (#299), and *Shigella boydii* type 3 (#196); each contains a terminal α-Galf residue but resulted in signals of only 49, 66, and 26 RFU, respectively (FIGS. 12A-B). The investigators suspect the inverted stereochemistry at the anomeric carbon of Galf generates a steric block that prevents binding.

Figure 4:
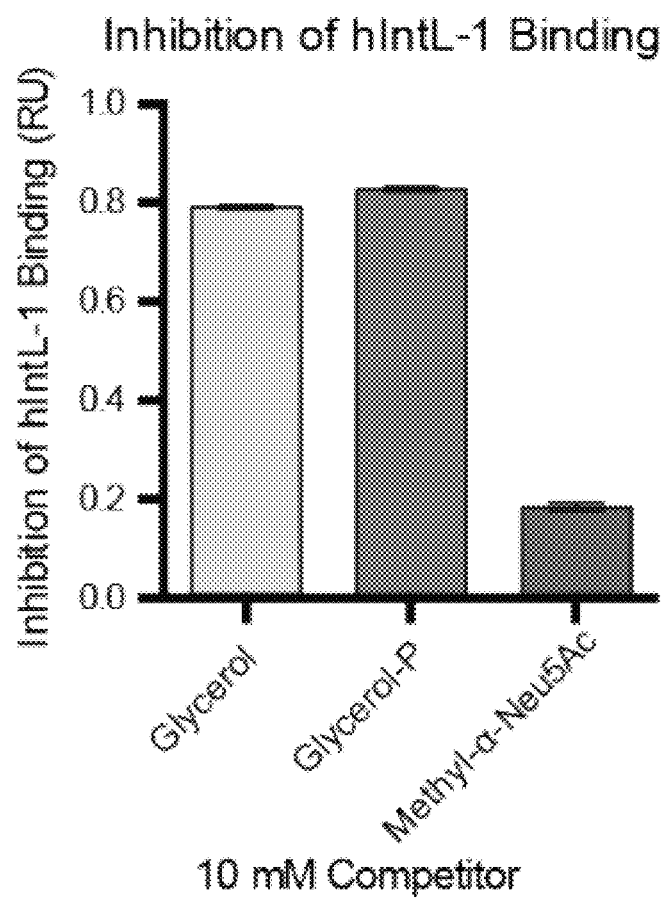
FIG. 4. Competitive binding assay with hIntL-1. Three compounds (glycerol, 1-phosphoglycerol, and α-methylglycoside of Neu5Ac) were tested as competitors for hIntL-1 binding to immobilized β-Galf. Error bars represent the s.d. of the mean (n=2).

Another interesting example of specificity is the lack of affinity for N-acetyl-neuraminic acid (Neu5Ac, 6) in the mammalian glycan array and ELISA (FIGS. 4 and 15A-B). Both Kdo and Neu5Ac belong to the 2-keto-3-deoxy-sugar acid family and contain terminal vicinal diols. A structural difference between these sugars is the replacement of the 5-hydroxyl with a 5-N-acetyl group. This substituent adds steric bulk to the monosaccharide. Another difference is the relative orientation of the carboxylate and the anomeric substituent. The differences in sterics and conformation, may prevent hIntL-1 binding. How hIntL-1 binds carbohydrates was an open question. A search of solved protein structures yielded no candidate template. This is not surprising as there was no structural information available for intelectin proteins or the newly termed X-type sequence motif (Vasta et al., 2007). To this end, the investigators obtained a protein x-ray crystal structure of hIntL-1. Strep-tag II hIntL-1 was purified from transiently transfected suspension HEK 293T (FIGS. 11A-E). After optimization around a lead condition, apo crystals that diffract to 1.8 Å were obtained. Unfortunately, the data could not be phased using structures available in the protein data bank (PDB). The investigators thus turned to *Xenopus laevis* intelectin 1 (XIntL-1) expressed in *Trichoplusia ni* cells using methione dropout medium supplemented with exogenous L-selenomethione. The result was the first structure of an X-type lectin. It reveals the protein forms a disulfide linked trimer with the carbohydrate binding sites located on a single face. The orientation of the carbohydrate-binding sites is consistent with the ability of hIntL-1 to bind avidly to microbial surfaces. The structure reveals why the lectin binds to glycans with terminal 1,2 diols. There is a calcium ion in the binding site to which the terminal 1,2-diol of the glycan coordinates.

How hIntL-1 binds carbohydrates was an open question. A search of solved protein structures yielded no candidate template. This is not surprising as there was no structural information available for intelectin proteins or the newly termed X-type sequence motif (Vasta et al., 2007). To this end, the investigators obtained a protein x-ray crystal structure of hIntL-1. Strep-tag II hIntL-1 was purified from transiently transfected suspension HEK 293T (FIGS. 11A-E). After optimization around a lead condition, apo crystals that diffract to 1.8 Å were obtained. Unfortunately, the data could not be phased using structures available in the protein data bank (PDB). The investigators thus turned to *Xenopus laevis* intelectin 1 (XIntL-1) expressed in *Trichoplusia ni* cells using methione dropout medium supplemented with exogenous L-selenomethione. The result was the first structure of an X-type lectin. It reveals the protein forms a disulfide linked trimer with the carbohydrate binding sites located on a single face. The orientation of the carbohydrate-binding sites is consistent with the ability of hIntL-1 to bind avidly to microbial surfaces. The structure reveals why the lectin binds to glycans with terminal 1,2 diols. There is a calcium ion in the binding site to which the terminal 1,2-diol of the glycan coordinates.

hIntL-1 Binding to Isolated Intestinal Microbiome Stains with Genetically Characterized Backgrounds.

The inventors have begun to examine the binding of hIntL-1 to bacteria known to reside in the human intestine. Strains of relevant bacteria were grown anaerobically. The samples are fixed using 1% formaldehyde for 30 min on ice. This mode of fixation does not perturb or harm the cell surface glycans. Fixed cells are exposed to Strep-tagged (IBS Lifesciences) -hIntL-1. The Strep-tag not necessary for function but added because it facilitates purification and detection. Cells were analyzed by flow cytometry on a BD FACSCalibur or LSRII. Bacterial cells were identified using either propidium iodide (PI) or DAPI. An anti-Strep-tag antibody conjugated to the fluorophore Oyster 645 nm was used to detect the population of bacteria bound by hIntL-1.

Figure 17:
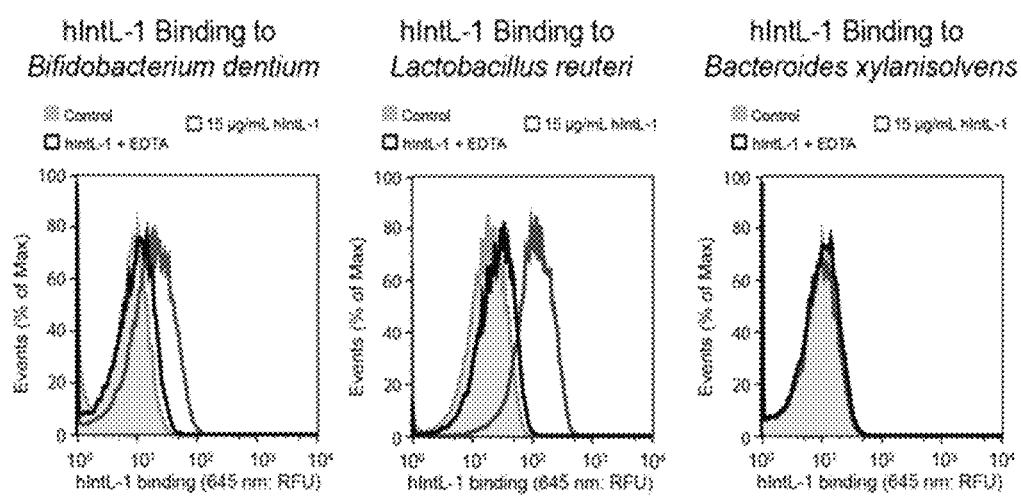
FIG. 17. Representative example of hIntL-1 binding to different strains commonly found in the intestinal microbiome. Unstained cells are shown in grey, cells stained in the presence of calcium ions are in blue, and cells stained in the presence of EDTA in black. From these results, the inventors conclude that hIntL-1 binds to *Bifidobacterium dentium* and *Lactobacillus reuteri*, but not to *Bacteroides xylanisolvens*. This analysis is representative of what has been done on every strain that the inventors have found to be bound by hIntL-1. A more extensive summary of the bacteria bound by hIntL-1 can be found in Tables 1 and 2.
Figure 23:
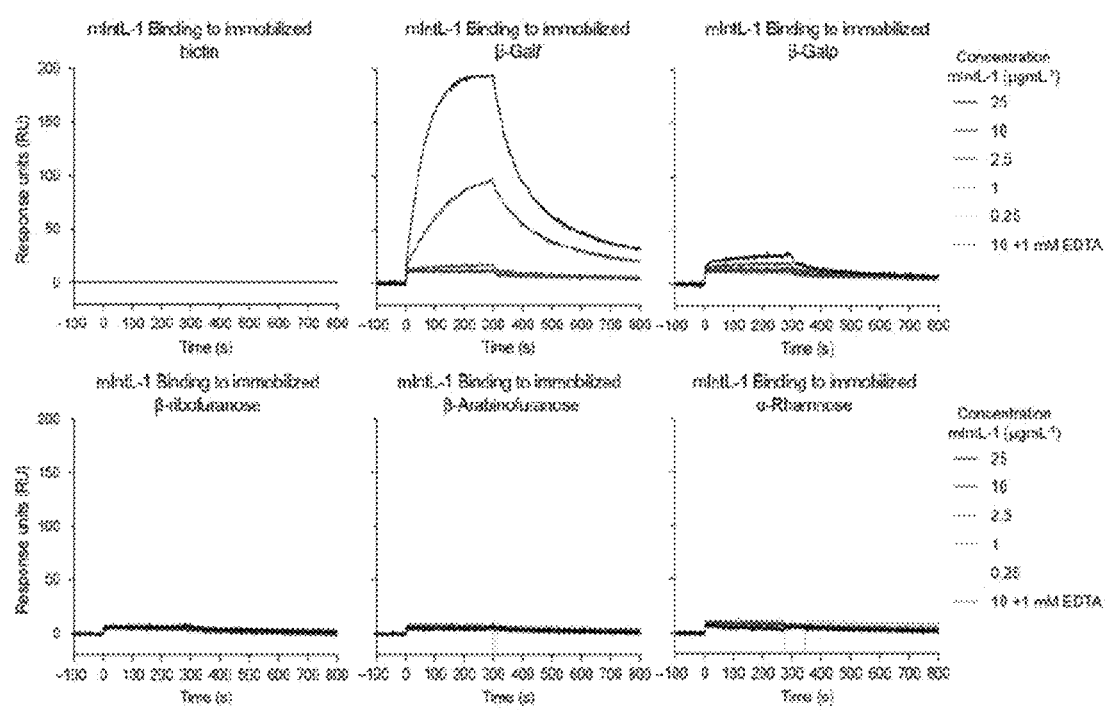
FIG. 23. Mouse intelectin-1 binding to immobilized carbohydrates. Purified Strep-mIntL-1 binding to immobilized carbohydrates monitored using SPR. Addition of EDTA prevents carbohydrate binding, supporting a role for calcium ions in carbohydrate binding. Data are referenced to the biotin channel.
Figure 24:
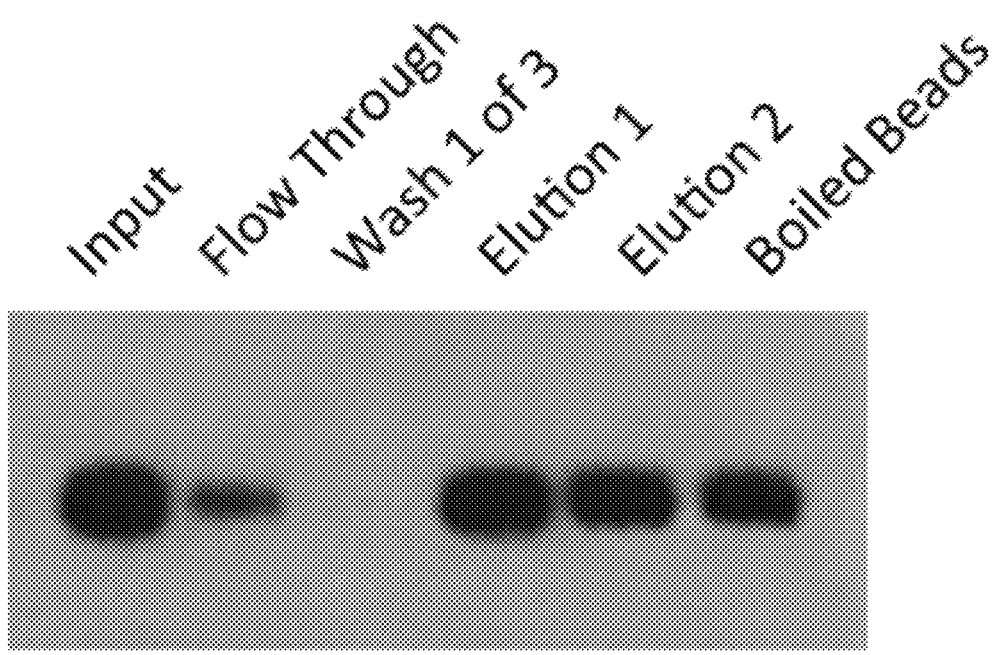
FIG. 24. Representative image of hIntL-1 purification on a sorbitol::sepharose column generated through divinyl sulfone chemistry. Protein was visualized via Western blot using a sheep anti-hntL-1 polyclonal antibody (R&D Systems) and a donkey anti-sheep::HRP conjugate.

To determine whether observed binding is dependent on hIntL-1 interaction with microbial glycans, the inventors take advantage of critical role of calcium ions in hIntL-1 binding. The addition of the calcium ion chelator EDTA, which sequesters bound calcium ions, serves as an important specificity control. Fixed bacteria are incubated in 20 mM HEPES (pH 7.2), 150 mM NaCl, 10 mM $CaCl_2$, 15 µg/mL Strep-tagged-hIntL-1, 0.1% bovine serum albumin (BSA), 0.05% Tween-20, 2 µg/mL StrepMAB-Classic conjugated to Oyster 645 (IBA Lifesciences, cat. no.: 2-1555-050). For the cells incubated in the absence of calcium ions, the following solution is used 20 mM HEPES (pH 7.2), 150 mM NaCl, 5 mM EDTA, 15 µg/mL Strep-tagged-hIntL-1, 0.1% bovine serum albumin (BSA), 0.05% tween-20, 2 µg/mL StrepMAB-Classic conjugated to Oyster 645 (IBA Lifesciences, cat. no.: 2-1555-050). Cell samples were analyzed by flow cytometry consecutively using an identical instrument setting. The percentages of unstained cells, cells stained in the presence of calcium ions, and cells stained in the presence of EDTA were directly compared. Increased hIntL-1 binding signal in the presence of calcium ions when compared to unstained cells or the EDTA sample indicates specific binding to the surface glycans of that strain of bacteria. FIG. 17 is representative of the data obtained. A list of bacteria bound by hIntL-1 can be found in Table 1. Many of these *Bifidobacterium* and *Lactobacillus* species represent "good" bacteria that are supplemented in commercial probiotics (as described above).

hIntL-1 Binding to Commercial Probiotic Supplements.

Commercially available probiotic supplements are commonly taken because of their reported health benefits. The bacteria, however, rarely take up residence in the intestinal GI tract and are typically cleared shortly after ingestion. The inventors hypothesize that hIntL-1 can be supplemented as a prebiotic to these to increase the uptake and retention of these bacteria. To test this hypothesis, they examined the binding of hIntL-1 to the microbes present in a probiotic supplement, Lifeway Kefir. The inventors chose this probiotic because of its complexity, it contains twelve species, including *Lactobacillus lactis, Lactobacillus rhamnoses, Streptococcus diacetylactis, Lactobacillus plantarum, Lactobacillus casei, Saccharomyces florentinus, Leuconostoc cremoris, Bifidobacterium breve, Lactobacillus acidophilus, Bifidobacterium lactis,* and *Lactobacillus reuteri*. They had observed that multiple *Lactobacillus* and *Bifidobacterium* species were bound by hIntL-1. These species are commonly found in other probiotics, including yogurts and dried probiotic supplements.

The probiotic species from Lifeway Keifer were isolated by repeated washing in a phosphate buffered saline solution until the majority of the fat was removed, as evidenced by light microscopy. The microbes (bacteria and yeast) were fixed in 1% formaldehyde. Microbes were stained as described above using 20 mM HEPES (pH 7.2), 150 mM NaCl, 10 mM $CaCl_2$, 15 µg/mL Strep-tagged-hIntL-1, 0.1% BSA, 0.05% Tween-20, 2 µg/mL StrepMAB-Classic conjugated to Oyster 645. For the cells incubated in the absence of calcium ions, the following solution is used 20 mM HEPES (pH 7.2), 150 mM NaCl, 5 mM EDTA, 15 µg/mL Strep-tagged-hIntL-1, 0.1% BSA, 0.05% Tween-20, 2 µg/mL StrepMAB-Classic conjugated to Oyster 645. Cell samples were analyzed by flow cytometry consecutively using an identical instrument setting. The percentages of unstained cells, cells stained in the presence of calcium ions, and cells stained in the presence of EDTA were directly compared. FIG. 18 shows the results of this experiment. The data suggest that approximately 80% of the microbes present in Lifeway® Kefir are targets of hIntL-1 binding.

hIntL-1 Binding to Patient-Specific Fecal Microbiomes.

Human fecal samples provide a non-invasive proxy of the intestinal microbiome of a patient. The inventors have isolated the intestinal microbiome from human fecal samples and analyzed it for hIntL-1 binding. The isolated microbiome was fixed using an aqueous solution of 1% formaldehyde. Cells were stained as described elsewhere, using either a solution including calcium ions (100 mM) or one containing the calcium ion chelator EDTA. Microbes were exposed to 20 mM HEPES (pH 7.2), 150 mM NaCl, 10 mM $CaCl_2$, 15 µg/mL Strep-tagged-hIntL-1, 0.1% bovine serum albumin (BSA), 0.05% tween-20, 2 µg/mL StrepMAB Classic conjugated to Oyster 645 (IBA Lifesciences, cat. no.: 2-1555-050). To test for a role for calcium ions, cells were exposed to a solution of 20 mM HEPES (pH 7.2), 150 mM NaCl, 1 mM EDTA, 15 µg/mL Strep-tagged-hIntL-1, 0.1% bovine serum albumin (BSA), 0.05% tween-20, 2 µg/mL StrepMAB Classic Conjugated to Oyster 645 (IBA Lifesciences, cat. no.: 2-1555-050). Cells are analyzed consecutively on a BD LSRII flow cytometer using identical instrument setting. Unstained cells, cells stained in the presence of calcium ions (10 mM), and cells stained in the presence of EDTA were directly compared. Increased hIntL-1 binding in the presence of calcium ions compared to that observed with unstained cells or with EDTA present was judged to be specific binding to the surface glycans of that strain of bacteria. FIGS. 19A-C show representative images of this analysis. The human fecal microbiome is a complex mixture of microbial species that differ in their size and shape (FSC vs. SSC). Analysis of these bacteria for binding to hIntL-1 indicates approximately 25% of the bacteria that make up the human microbiome are bound by hIntL-1. From the FSC vs. SSC plot, these appear to be diverse bacterial species.

This information highlights that the percentage of the human microbome bound by hIntL-1 is large, suggesting hIntL-1 could act on a significant proportion of the cells within the microbiome. This sort of analysis could be used to rapidly profile the human microbiome and correlate dysbiosis with disease. Specifically, an increase or decrease in binding of hIntL-1 to the fecal microbime may be useful for measuring dysbiosis of the intestine or lung in disease states such as asthma in the latter, or Crohn's disease or IBS in the former.

hIntL-1 Binding to Infant Fecal Microbiomes.

Human fecal samples provide a non-invasive proxy of the intestinal microbiome of a patient, and the inventors sought to examine the microbiome of an infant. These studies were prompted by the observation that hIntL-1 binds bacterial species that are prevalent in infants. The data shown here were generated using a fecal sample from a 18 month old male. The cells were fixed and stained using the procedures described previously. FIGS. 20A-B show representative images of this analysis. As expected from our previous analysis, the human infant fecal microbiome is a complex mixture of microbial species that differ in their size and shape (FSC vs. SSC). As with adults, about 25% of the bacteria that make up the human infant microbiome are bound by hIntL-1. From the FSC vs. SSC plot, these appear to be diverse bacteria that belong to many unique species.

This information demonstrates that the infant microbome, which is known to be essential for infant immune health, contains a large proportion of bacteria that are bound by hIntL-1. The inventors speculate that hIntL-1 may be able to be added to infant probiotics to help retain these bacteria. Additionally, they believe this sort of analysis can be used to rapidly profile the infant microbiome and correlate dysbiosis with disease. Specifically, an increase or decrease in binding of hIntL-1 to the fecal microbime may be useful for measuring dysbiosis of the intestine.

hIntL-2 Binding to Infant Fecal Microbiomes.

Humans have two intelectins: hIntL-1 and human intelectin-2 (hIntL-2). The latter is highly homologous to hIntL-1, although its expression seems more restricted. HIntL-2 is expressed almost exclusively in the GI tract. To compare hIntL-1 and hIntL02, the inventors isolated the intestinal mirobiome from human feces and analyzed it for hIntL-2 binding. The data shown here were generated using a fecal sample from a 18 month old male. The samples were processed and analyzed as described above. Cells were analyzed consecutively on a BD LSRII flow cytometer using identical instrument setting. Unstained cells, cells stained in the presence of calcium ions, and cells stained in the presence of EDTA are directly compared. Increased hIntL-2 binding signal in the presence of calcium ions when compared to unstained cells or the EDTA sample represents specific binding to the surface glycans of that strain of bacteria. FIGS. 21A-B shows representative images of this analysis. When bacteria are analyzed for binding to hIntL-2, the inventors found that ~32% of the bacteria that make up the human infant microbiome are bound by hIntL-2. From the FSC vs. SSC plot, these appear to be diverse bacteria that belong to many unique species.

This information demonstrates that the infant microbome, which is known to be essential for infant immune health, contains a large proportion of bacteria that are bound by hIntL-2. From the appearance of this binding data, the inventors speculate that the bacterial ligands of hIntL-2 differ from hIntL-1. The inventors speculate that hIntL-1 may be able to be added to infant probiotics to help retain these bacteria. Additionally, they believe this sort of analysis can be used to rapidly profile the infant microbiome and correlate dysbiosis with disease. Specifically, an increase or decrease in binding of hIntL-1 to the fecal microbime may be useful for measuring dysbiosis of the intestine.

Purification of hIntL-1 on a Sorbitol::Sepharose Column.

Divinyl sulfone activated sepharose was purchased from US Biological (Salem, Mass.; Cat. no. WU6752). Resin was washed three times with doubly distilled water. Resin was then washed with two resin volumes of 100 mM sodium bicarbonate (pH 10.0). The resin was generated via incubation of resin in a solution of 100 mM sodium bicarbonate (pH 10.0) plus 20 mg/mL sorbitol at 4° C. for at least 18 hours. The resin was washed with the bicarbonate solution. The resin was blocked via incubation of resin in a solution of 100 mM Tris-base (pH 9.5) at 4° C. for at least 4 hours. The resin can then be washed, stored in buffer, and is ready for use.

Human intelectin-1 was bound to the resin through incubation of hintL-1 conditioned culture media plus 10 mM CaCl$_2$. The resin was washed with 10 column volumes of 20 mM HEPES (7.4) 150 mM NaCl, 10 mM CaCl$_2$. Bound hIntL-1 was eluted using 10 column volumes of 20 mM HEPES (7.4) 150 mM NaCl, 15 mM EDTA.

TABLE 1

Microbiome species bound by hIntL-1 as monitored by flow cytometry.

| Genus | Species |
| --- | --- |
| Ruminococcus | torques |
| Anaerococcus | hydrogenalis |
| Roseburia | intestinalis |
| Dorea | longicatena |
| Bifidobacterium | dentium |
| Eubacterium | ventriosum |
| Eubacterium | biforme |
| Escherichia | fergusonii |
| Lactobacillus | reuteri |
| Bacteroides | plebeius |
| Bifidobacterium | angulatum |
| Bifidobacterium | bifidum |
| Lactobacillus | ruminis |

TABLE 2

Microbiome species not bound by hIntL-1 as monitored by flow cytometry.

| Genus | Species |
| --- | --- |
| Escherichia | coli K12 |
| Bacteroides | ovatus |
| Clostridium | bolteae |
| Bacteroides | vulgatus |
| Parabacteroides | merdae |
| Roseburia | intestinalis |
| Bacteroides | xylanisolvens |
| Clostridium | asparagiforme |
| Mitsuokella | multacida |
| Bacteroides | thetaiotaomicron VPI-5482 |
| Bacteroides | uniformis |
| Enterobacter | cancerogenus |
| Desulfovibrio | piger |
| Bifidobacterium | pseudocatenulatum |
| Bacteroides | thetaiotaomicron 3731 |
| Coprococcus | comes |
| Ruminococcus | gnavus |
| Holdemania | filiformis |
| Clostridium | hylemonae |
| Anaerotruncus | colihominis |
| Providencia | alcalifaciens |
| Ruminococcus | obeum |
| Collinsella | stercoris |
| Bacteroides | caccae |
| Clostridium | symbiosum |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

U.S. Pat. No. 5,440,013
U.S. Pat. No. 5,446,128
U.S. Pat. No. 5,475,085
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,840,833
U.S. Pat. No. 5,859,184
U.S. Pat. No. 5,889,155
U.S. Pat. No. 5,929,237
U.S. Pat. No. 7,183,059
U.S. Pat. No. 7,192,713
Ausubel et al., Current Protocols in Molecular Biology, Greene Publishing Associates and Wiley Interscience, N.Y., 1994.
Blixt et al., Proceedings of the National Academy of Sciences of the United States of America 101:17033-17038, 2014.
Bodanszky et al., *J. Antibiot.*, 29(5):549-53, 1976.
Capaldi et al., *Biochem. Biophys. Res. Comm.*, 74(2):425-433, 1977.
Datta et al., *Infect. Immun.* 73:4025-4033, 2005.
Drickamer, K. *Prog Nucleic Acid Res Mol Biol* 45:207-232, 1993.
French et al., *Int. J. Parasitol.* 38:467-475, 2008.
Garlatti et al. *EMBO J.*, 26, 623-633, 2007.
Goodbourn and Maniatis, *Proc. Natl. Acad. Sci. USA*, 85:1447, 1988.
Hempel et al., *AMA*, 2012, 307, 1959.
Hiramatsu-Ito et al., *Cardiovascular Res* 0.110:107-117, 2016.
Jackson, *Seminars in Oncology*, 24:L164-172, 1997.
Johnson et al., In: *Biotechnology and Pharmacy*, Pezzuto et al., eds., Chapman and Hall, New York, 1993.
Jones et al., *J. Med. Chem.*, 39:904-917, 1996.
Kerr et al., Am J Respir Crit Care Med 189:1005-1007, 2014.
Krissinel, E. *J. Mol. Biochem.*, 1:76-85, 2012.
Kuperman et al., *J Allergy Clin Immunol* 116, 305-311, 2005.
Lee et al., *Glycobiology* 7:367-372, 1997.
Lee et al., *Glycobiology* 11, 65-73, 2001.
Merrifield, *J Am. Chem. Soc.*, 85(14):2149-2154, 1963.
Nassau et al., *J Bacteriol* 178:1047-1052, 1996.
Pedersen and Turco, *Cell Mol Life Sci* 60:259-266, 2003.
Pemberton et al., *Proteomics* 4, 1101-1108, 2004.
Pemberton et al., *J Allergy Clin Immunol* 122:1033-1034, 2008.
Peptide Synthesis, 1985.
Physicians Desk Reference.
Protective Groups in Organic Chemistry, 1973
Remington's Pharmaceutical Sciences, 15$^{th}$ ed., 1035-1038 and 1570-1580, Mack Publishing Company, P A, 1980.
Robert & Gouet, *Nucleic Acids Res.*, 42, W320-W324, 2014.
Sambrook et al., In: *Molecular cloning: a laboratory manual*, 2$^{nd}$ Ed., Cold Spring Harbor Laboratory Press, Cold Spring Harbor, N.Y., 1989.
Schafmeister et al., *J Amer. Chem. Soc.*, 122(24):5891-5892, 2000.
Schnaitman and Klena, *Microbiological reviews* 57:655-682, 1993.
Solid Phase Peptide Synthelia, 1984.
Stowell et al., *Nature chemical biology* 10:470-476, 2014.
Stowell et al., *Nat. Chem. Biol.*, 10, 470-6, 2014.
Suzuki et al., *Biochemistry* 40:15771-15779, 2001.
Tefsen et al., *Glycobiology* 22, 456-469, 2012.
The Merck Index, 11th Edition.
Thomsen et al., *Mol Immunol* 48:369-381, 2011.
Tsuji et al., *J Biol Chem* 276:23456-23463, 2001.
Vasta et al., *Advances in experimental medicine and biology* 598:389-406, 2007.
Voehringer et al., *Exp Parasitol* 116:458-466, 2007.
Watanabe et al., *Cardiovascular Res.* 110:118-128, 2016.
Wesener et al., *Biochemistry* 52:4391-4398, 2013.
Wesener et al., *Nature Structural and Molecular Biology.* 22:603-610, 2015.
Yang et al., *Am J Physiol Endocrinol Metab* 290:E1253-1261, 2006.

---

What is claimed is:

1. A method of promoting the growth and/or stability of a microbiome in a subject comprising administering to the subject an intelectin molecule.

2. The method of claim 1, wherein in intelectin molecule is administered in probiotic formulation containing one or more beneficial microorganisms.

3. The method of claim 2, wherein said one or more beneficial microorganisms are from the genus *Lactobacillus* or *Bifidobacterium*, or a species selected from the group consisting of the bacteria set forth in Table 1.

4. The method of claim 1, where the intelectin binds to a β-linked D-galactofuranose, a glycan containing a heptose, D-glycero-D-talo-oct-2-ulosonic acid (KO) and/or 3-deoxy-D-manno-oct-2-ulosonic acid (KDO) residue, and/or a saccharide residue modified with a phospho-glycerol (Gro-P) substituent.

5. The method of claim 1, wherein the intelectin is hIntL-1 or hIntL-2, and the subject is a human, or wherein the intelectin is a non-human intelectin, and the subject is a non-human mammal of the same species as the intelectin.

6. The method of claim 5, wherein the intelectin is mouse intelectin-1, and the subject is a mouse, or the intelectin is a fish intelectin, and the subject is a fish.

7. The method of claim 1, wherein the intelectin is PEGylated.

8. The method of claim 1, wherein the intelectin is administered orally, rectally, vaginally, topically or via inhalation.

9. The method of claim 1, wherein said subject suffers from one or more of lactose intolerance, antibiotic-induced diarrhea, eczema, *Heliobacter pylori* infection, irritable bowel syndrome, colitis, necrotizing enterocolitis, bacterial vaginosis, inflammation, high blood pressure, elevated cholesterol, atherosclerosis, obesity, Crohn's Disease, an allergy, asthma, cancer (e.g., colorectal cancer) and/or vitamin deficiency.

* * * * *

SEQUENCE LISTING

<160> NUMBER OF SEQ ID NOS: 24

<210> SEQ ID NO 1
<211> LENGTH: 32
<212> TYPE: DNA
<213> ORGANISM: Artificial sequence
<220> FEATURE:
<223> OTHER INFORMATION: Synthetic primer

<400> SEQUENCE: 1
cgtgggatcc tggagggagg gagtgaagga gc                                    32

<210> SEQ ID NO 2
<211> LENGTH: 36
<212> TYPE: DNA
<213> ORGANISM: Artificial sequence
<220> FEATURE:
<223> OTHER INFORMATION: Synthetic primer

<400> SEQUENCE: 2

-continued gccagctcga gaccttggga tctcatggtt gggagg                                36

<210> SEQ ID NO 3
<211> LENGTH: 80
<212> TYPE: DNA
<213> ORGANISM: Artificial sequence
<220> FEATURE:
<223> OTHER INFORMATION: Synthetic primer

<400> SEQUENCE: 3
accaccagag gatggagtac agattggagc catccgcagt ttgaaaagtc tacagatgag    60
gctaatactt acttcaagga                                                80

<210> SEQ ID NO 4
<211> LENGTH: 313
<212> TYPE: PRT
<213> ORGANISM: Homo sapiens

<400> SEQUENCE: 4

```
Met Asn Gln Leu Ser Phe Leu Leu Phe Leu Ile Ala Thr Thr Arg Gly
1               5                   10                  15

Trp Ser Thr Asp Glu Ala Asn Thr Tyr Phe Lys Glu Trp Thr Cys Ser
            20                  25                  30

Ser Ser Pro Ser Leu Pro Arg Ser Cys Lys Glu Ile Lys Asp Glu Cys
        35                  40                  45

Pro Ser Ala Phe Asp Gly Leu Tyr Phe Leu Arg Thr Glu Asn Gly Val
    50                  55                  60

Ile Tyr Gln Thr Phe Cys Asp Met Thr Ser Gly Gly Gly Gly Trp Thr
65                  70                  75                  80

Leu Val Ala Ser Val His Glu Asn Asp Met Arg Gly Lys Cys Thr Val
                85                  90                  95

Gly Asp Arg Trp Ser Ser Gln Gln Gly Ser Lys Ala Val Tyr Pro Glu
            100                 105                 110

Gly Asp Gly Asn Trp Ala Asn Tyr Asn Thr Phe Gly Ser Ala Glu Ala
        115                 120                 125

Ala Thr Ser Asp Asp Tyr Lys Asn Pro Gly Tyr Tyr Asp Ile Gln Ala
    130                 135                 140

Lys Asp Leu Gly Ile Trp His Val Pro Asn Lys Ser Pro Met Gln His
145                 150                 155                 160

Trp Arg Asn Ser Ser Leu Leu Arg Tyr Arg Thr Asp Thr Gly Phe Leu
                165                 170                 175

Gln Thr Leu Gly His Asn Leu Phe Gly Ile Tyr Gln Lys Tyr Pro Val
            180                 185                 190

Lys Tyr Gly Glu Gly Lys Cys Trp Thr Asp Asn Gly Pro Val Ile Pro
        195                 200                 205

Val Val Tyr Asp Phe Gly Asp Ala Gln Lys Thr Ala Ser Tyr Tyr Ser
    210                 215                 220

Pro Tyr Gly Gln Arg Glu Phe Thr Ala Gly Phe Val Gln Phe Arg Val
225                 230                 235                 240

Phe Asn Asn Glu Arg Ala Ala Asn Ala Leu Cys Ala Gly Met Arg Val
                245                 250                 255

Thr Gly Cys Asn Thr Glu His His Cys Ile Gly Gly Gly Gly Tyr Phe
            260                 265                 270

Pro Glu Ala Ser Pro Gln Gln Cys Gly Asp Phe Ser Gly Phe Asp Trp
        275                 280                 285

Ser Gly Tyr Gly Thr His Val Gly Tyr Ser Ser Ser Arg Glu Ile Thr
```

```
                        290                 295                 300
        Glu Ala Ala Val Leu Leu Phe Tyr Arg
        305                 310

<210> SEQ ID NO 5
<211> LENGTH: 325
<212> TYPE: PRT
<213> ORGANISM: Homo sapiens

<400> SEQUENCE: 5

Met Leu Ser Met Leu Arg Thr Met Thr Arg Leu Cys Phe Leu Leu Phe
1               5                   10                  15

Phe Ser Val Ala Thr Ser Gly Cys Ser Ala Ala Ala Ser Ser Leu
            20                  25                  30

Glu Met Leu Ser Arg Glu Phe Glu Thr Cys Ala Phe Ser Phe Ser Ser
        35                  40                  45

Leu Pro Arg Ser Cys Lys Glu Ile Lys Glu Arg Cys His Ser Ala Gly
    50                  55                  60

Asp Gly Leu Tyr Phe Leu Arg Thr Lys Asn Gly Val Val Tyr Gln Thr
65                  70                  75                  80

Phe Cys Asp Met Thr Ser Gly Gly Gly Gly Trp Thr Leu Val Ala Ser
                85                  90                  95

Val His Glu Asn Asp Met Arg Gly Lys Cys Thr Val Gly Asp Arg Trp
            100                 105                 110

Ser Ser Gln Gln Gly Asn Lys Ala Asp Tyr Pro Glu Gly Asp Gly Asn
        115                 120                 125

Trp Ala Asn Tyr Asn Thr Phe Gly Ser Ala Glu Ala Ala Thr Ser Asp
    130                 135                 140

Asp Tyr Lys Asn Pro Gly Tyr Tyr Asp Ile Gln Ala Lys Asp Leu Gly
145                 150                 155                 160

Ile Trp His Val Pro Asn Lys Ser Pro Met Gln His Trp Arg Asn Ser
                165                 170                 175

Ala Leu Leu Arg Tyr Arg Thr Asn Thr Gly Phe Leu Gln Arg Leu Gly
            180                 185                 190

His Asn Leu Phe Gly Ile Tyr Gln Lys Tyr Pro Val Lys Tyr Arg Ser
        195                 200                 205

Gly Lys Cys Trp Asn Asp Asn Gly Pro Ala Ile Pro Val Val Tyr Asp
    210                 215                 220

Phe Gly Asp Ala Lys Lys Thr Ala Ser Tyr Tyr Ser Pro Tyr Gly Gln
225                 230                 235                 240

Arg Glu Phe Val Ala Gly Phe Val Gln Phe Arg Val Phe Asn Asn Glu
                245                 250                 255

Arg Ala Ala Asn Ala Leu Cys Ala Gly Ile Lys Val Thr Gly Cys Asn
            260                 265                 270

Thr Glu His His Cys Ile Gly Gly Gly Phe Phe Pro Gln Gly Lys
        275                 280                 285

Pro Arg Gln Cys Gly Asp Phe Ser Ala Phe Asp Trp Asp Gly Tyr Gly
    290                 295                 300

Thr His Val Lys Ser Ser Cys Ser Arg Glu Ile Thr Glu Ala Ala Val
305                 310                 315                 320

Leu Leu Phe Tyr Arg
                325

<210> SEQ ID NO 6
<211> LENGTH: 313
```

<212> TYPE: PRT
<213> ORGANISM: Mus musculus

<400> SEQUENCE: 6

```
Met Thr Gln Leu Gly Phe Leu Leu Phe Ile Met Val Ala Thr Arg Gly
1               5                   10                  15

Cys Ser Ala Ala Glu Glu Asn Leu Asp Thr Asn Arg Trp Gly Asn Ser
            20                  25                  30

Phe Phe Ser Ser Leu Pro Arg Ser Cys Lys Glu Ile Lys Gln Glu His
        35                  40                  45

Thr Lys Ala Gln Asp Gly Leu Tyr Phe Leu Arg Thr Lys Asn Gly Val
    50                  55                  60

Ile Tyr Gln Thr Phe Cys Asp Met Thr Thr Ala Gly Gly Gly Trp Thr
65                  70                  75                  80

Leu Val Ala Ser Val His Glu Asn Asn Met Arg Gly Lys Cys Thr Val
                85                  90                  95

Gly Asp Arg Trp Ser Ser Gln Gln Gly Asn Arg Ala Asp Tyr Pro Glu
            100                 105                 110

Gly Asp Gly Asn Trp Ala Asn Tyr Asn Thr Phe Gly Ser Ala Glu Ala
        115                 120                 125

Ala Thr Ser Asp Asp Tyr Lys Asn Pro Gly Tyr Phe Asp Ile Gln Ala
    130                 135                 140

Glu Asn Leu Gly Ile Trp His Val Pro Asn Lys Ser Pro Leu His Asn
145                 150                 155                 160

Trp Arg Lys Ser Ser Leu Leu Arg Tyr Arg Thr Phe Thr Gly Phe Leu
                165                 170                 175

Gln His Leu Gly His Asn Leu Phe Gly Leu Tyr Lys Lys Tyr Pro Val
            180                 185                 190

Lys Tyr Gly Glu Gly Lys Cys Trp Thr Asp Asn Gly Pro Ala Leu Pro
        195                 200                 205

Val Val Tyr Asp Phe Gly Asp Ala Arg Lys Thr Ala Ser Tyr Tyr Ser
    210                 215                 220

Pro Ser Gly Gln Arg Glu Phe Thr Ala Gly Tyr Val Gln Phe Arg Val
225                 230                 235                 240

Phe Asn Asn Glu Arg Ala Ala Ser Ala Leu Cys Ala Gly Val Arg Val
                245                 250                 255

Thr Gly Cys Asn Thr Glu His His Cys Ile Gly Gly Gly Gly Phe Phe
            260                 265                 270

Pro Glu Gly Asn Pro Val Gln Cys Gly Asp Phe Ala Ser Phe Asp Trp
        275                 280                 285

Asp Gly Tyr Gly Thr His Asn Gly Tyr Ser Ser Arg Lys Ile Thr
    290                 295                 300

Glu Ala Ala Val Leu Leu Phe Tyr Arg
305                 310
```

<210> SEQ ID NO 7
<211> LENGTH: 313
<212> TYPE: PRT
<213> ORGANISM: Mus musculus

<400> SEQUENCE: 7

```
Met Thr Gln Leu Gly Phe Leu Leu Phe Ile Met Ile Ala Thr Arg Val
1               5                   10                  15

Cys Ser Ala Ala Glu Glu Asn Leu Asp Thr Asn Arg Trp Gly Asn Ser
            20                  25                  30
```

```
Phe Phe Ser Ser Leu Pro Arg Ser Cys Lys Glu Ile Lys Gln Glu Asp
            35                  40                  45

Thr Lys Ala Gln Asp Gly Leu Tyr Phe Leu Arg Thr Glu Asn Gly Val
 50                  55                  60

Ile Tyr Gln Thr Phe Cys Asp Met Thr Thr Ala Gly Gly Gly Trp Thr
 65                  70                  75                  80

Leu Val Ala Ser Val His Glu Asn Asn Leu Arg Gly Arg Cys Thr Val
                 85                  90                  95

Gly Asp Arg Trp Ser Ser Gln Gln Gly Asn Arg Ala Asp Tyr Pro Glu
            100                 105                 110

Gly Asp Gly Asn Trp Ala Asn Tyr Asn Thr Phe Gly Ser Ala Glu Gly
        115                 120                 125

Ala Thr Ser Asp Asp Tyr Lys Asn Pro Gly Tyr Phe Asp Ile Gln Ala
130                 135                 140

Glu Asn Leu Gly Ile Trp His Val Pro Asn Asn Ser Pro Leu His Thr
145                 150                 155                 160

Trp Arg Asn Ser Ser Leu Leu Arg Tyr Arg Thr Phe Thr Gly Phe Leu
                165                 170                 175

Gln Arg Leu Gly His Asn Leu Phe Gly Leu Tyr Gln Lys Tyr Pro Val
            180                 185                 190

Lys Tyr Gly Glu Gly Lys Cys Trp Thr Asp Asn Gly Pro Ala Phe Pro
        195                 200                 205

Val Val Tyr Asp Phe Gly Asp Ala Gln Lys Thr Ala Ser Tyr Tyr Ser
    210                 215                 220

Pro Ser Gly Arg Asn Glu Phe Thr Ala Gly Tyr Val Gln Phe Arg Val
225                 230                 235                 240

Phe Asn Asn Glu Arg Ala Ala Ser Ala Leu Cys Ala Gly Val Arg Val
                245                 250                 255

Thr Gly Cys Asn Thr Glu His His Cys Ile Gly Gly Gly Gly Phe Phe
            260                 265                 270

Pro Glu Phe Asp Pro Glu Cys Gly Asp Phe Ala Ala Phe Asp Ala
        275                 280                 285

Asn Gly Tyr Gly Thr His Ile Arg Tyr Ser Asn Ser Arg Glu Ile Thr
290                 295                 300

Glu Ala Ala Val Leu Leu Phe Tyr Arg
305                 310

<210> SEQ ID NO 8
<211> LENGTH: 322
<212> TYPE: PRT
<213> ORGANISM: Ovis aries

<400> SEQUENCE: 8

Met Pro Ala Gln Gly Pro Gly Val Arg Phe Cys Leu Leu Phe Leu
 1               5                  10                  15

Ser Leu Ala Ala Arg Gly Arg Gly Ala Val Thr Pro Ser Val Gly Lys
                 20                  25                  30

Phe Trp Gly Asn Glu Ile Cys Ala Pro Phe Leu Ser Phe Leu Pro Arg
            35                  40                  45

Thr Cys Lys Glu Ile Lys Glu Thr Cys His Ser Ala Gly Asp Gly Leu
 50                  55                  60

Tyr His Leu Arg Thr Glu Asn Gly Val Ile Tyr Gln Thr Phe Cys Asp
 65                  70                  75                  80

Met Thr Ser Gly Gly Gly Gly Trp Thr Leu Val Ala Ser Ile His Glu
                 85                  90                  95
```

```
Asn Asn Met Arg Gly Lys Cys Thr Leu Gly Asp Arg Trp Ser Ser Gln
                100                 105                 110

Gln Gly Asn Arg Ala Asp Tyr Pro Glu Gly Asp Gly Asn Trp Ala Asn
            115                 120                 125

Tyr Asn Thr Phe Gly Ser Ala Glu Ala Ala Thr Ser Asp Asp Tyr Lys
        130                 135                 140

Asn Pro Gly Tyr Tyr Asp Ile Gln Ala Gln Asp Leu Gly Ile Trp His
145                 150                 155                 160

Val Pro Asn Lys Ser Pro Leu Gln His Trp Arg Asn Ser Ser Leu Leu
                165                 170                 175

Arg Tyr His Thr Asn Thr Gly Phe Phe Arg Arg Leu Gly His Asn Leu
            180                 185                 190

Phe Gly Leu Tyr Gln Lys Phe Pro Val Lys Tyr Gly Ala Gly Lys Cys
        195                 200                 205

Trp Thr Asp Asn Gly Pro Ala Ile Pro Val Asp Tyr Asp Phe Gly Asp
210                 215                 220

Ala Glu Lys Thr Ala Ser Tyr Tyr Ser Pro Asn Gly Gln Arg Glu Phe
225                 230                 235                 240

Val Ala Gly Phe Val Gln Phe Arg Val Phe Asn Asn Glu Gly Ala Ala
                245                 250                 255

Asn Ala Leu Cys Ala Gly Met Arg Val Thr Gly Cys Asn Thr Glu Phe
            260                 265                 270

His Cys Ile Gly Gly Gly Gly Tyr Phe Pro Glu Ser Ser Pro Trp Gln
        275                 280                 285

Cys Gly Asp Phe Ser Ser Phe Asp Trp Asn Gly Tyr Gly Ala His Arg
290                 295                 300

Gly Tyr Ser Ser Ser Arg Glu Ile Thr Glu Val Ala Val Leu Leu Phe
305                 310                 315                 320

Tyr Arg

<210> SEQ ID NO 9
<211> LENGTH: 339
<212> TYPE: PRT
<213> ORGANISM: Xenopus laevis

<400> SEQUENCE: 9

Met Leu Ser Tyr Ser Leu Leu Leu Ala Leu Ala Phe Pro Ala Gly
1               5                   10                  15

His Ala Gly Ser Cys Glu Gln Ala Ser Ile Ser Glu Lys Lys Glu Lys
            20                  25                  30

Ile Leu Asn Leu Leu Ala Cys Trp Thr Glu Gly Asn Ala Asp Asn Ser
        35                  40                  45

Leu Ser Arg Ser Gly Gly Ser Pro Thr Gly Asp Met Asn Tyr Gly Tyr
    50                  55                  60

Arg Ser Cys Asn Glu Ile Lys Ser Ser Asp Ser Arg Ala Pro Asp Gly
65                  70                  75                  80

Ile Tyr Thr Leu Ala Thr Glu Asp Gly Glu Ser Tyr Gln Thr Phe Cys
                85                  90                  95

Asp Met Thr Thr Asn Gly Gly Trp Thr Leu Val Ala Ser Val His
            100                 105                 110

Glu Asn Asn Met Phe Gly Lys Cys Thr Val Gly Asp Arg Trp Ser Thr
        115                 120                 125

Gln Gln Gly Asn Met Leu Gln Asn Pro Glu Gly Asp Gly Asn Trp Ala
    130                 135                 140
```

```
Asn Tyr Ala Thr Phe Gly Leu Pro Glu Gly Ala Thr Ser Asp Asp Tyr
145                 150                 155                 160

Lys Asn Pro Gly Tyr Tyr Asp Ile Glu Ala Lys Asn Leu Ala Leu Trp
                165                 170                 175

His Val Pro Asn Lys Thr Pro Met Val Met Trp Arg Asn Ser Ser Ile
            180                 185                 190

Leu Arg Tyr Arg Thr Gln Asn Gly Phe Leu Thr Glu Glu Gly Gly Asn
        195                 200                 205

Leu Phe Glu Leu Tyr Lys Lys Tyr Pro Val Lys Tyr Asp Ile Gly Lys
    210                 215                 220

Cys Leu Ala Asp Asn Gly Pro Ala Val Pro Val Val Tyr Asp Leu Gly
225                 230                 235                 240

Ser Ala Glu Lys Thr Ala Ser Leu Tyr Ser Pro Asn Gly Arg Ser Glu
                245                 250                 255

Phe Thr Pro Gly Phe Val Gln Phe Arg Ala Val Asn Ser Glu Arg Ala
            260                 265                 270

Thr Leu Ala Leu Cys Ala Gly Val Lys Val Lys Gly Cys Asn Val Glu
        275                 280                 285

His His Cys Ile Gly Gly Gly Tyr Ile Pro Glu Gly Ser Pro Arg
    290                 295                 300

Gln Cys Gly Asp Phe Ala Ala Leu Asp Trp Asp Gly Tyr Gly Thr Asn
305                 310                 315                 320

Leu Gly Trp Ser Ala Ser Lys Gln Ile Ile Glu Ala Ala Val Met Leu
                325                 330                 335

Phe Tyr Arg

<210> SEQ ID NO 10
<211> LENGTH: 314
<212> TYPE: PRT
<213> ORGANISM: Artificial sequence
<220> FEATURE:
<223> OTHER INFORMATION: Synthetic consensus sequence
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
```

<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (218)..(218)
<223> OTHER INFORMATION: Xaa can be any naturally occurring amino acid
<220> FEATURE:
<221> NAME/KEY: misc_feature
<222> LOCATION: (227)..(227)
<223> OTHER INFORMATION: Xaa can be any naturally occurring amino acid
<220> FEATURE:
<221> NAME/KEY: misc_feature
<222> LOCATION: (272)..(272)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid

<400> SEQUENCE: 10

```
Met Leu Gln Leu Xaa Phe Leu Leu Xaa Xaa Xaa Ala Leu Thr Arg Gly
1               5                   10                  15

Cys Ser Ala Ala Glu Glu Asn Asp Leu Xaa Xaa Trp Gly Asn Ser Leu
            20                  25                  30

Leu Ser Xaa Xaa Ser Leu Pro Arg Ser Cys Lys Glu Ile Lys Xaa Leu
        35                  40                  45

Cys Xaa Ser Ala Xaa Ser Gly Leu Tyr Leu Leu Arg Leu Glu Asn Gly
    50                  55                  60

Val Ile Tyr Gln Thr Phe Cys Asp Met Thr Xaa Gly Gly Gly Gly Trp
65                  70                  75                  80

Thr Leu Val Ala Ser Val His Glu Asn Asn Met Arg Gly Lys Cys Thr
                85                  90                  95

Val Gly Asp Arg Trp Ser Ser Gln Gln Gly Asn Arg Ala Asp Tyr Pro
            100                 105                 110

Glu Gly Asp Gly Asn Trp Ala Asn Tyr Asn Thr Phe Gly Ser Ala Glu
        115                 120                 125

Ala Ala Thr Ser Asp Asp Tyr Lys Asn Pro Gly Tyr Tyr Asp Ile Gln
130                 135                 140

Ala Lys Xaa Leu Gly Ile Trp His Val Pro Asn Lys Ser Pro Val Gln
            150                 155                 160
145

His Trp Arg Asn Ser Ser Leu Leu Arg Tyr Arg Thr Xaa Thr Gly Phe
            165                 170                 175

Leu Gln Thr Leu Gly His Asn Leu Phe Gly Ile Tyr Gln Lys Tyr Pro
        180                 185                 190

Val Lys Tyr Gly Glu Gly Lys Cys Trp Thr Asp Asn Gly Pro Val Ile
    195                 200                 205

Pro Val Val Tyr Asp Phe Gly Asp Ala Xaa Lys Thr Ala Ser Tyr Tyr
210                 215                 220

Ser Pro Xaa Gly Gln Arg Glu Phe Thr Ala Gly Phe Val Gln Phe Arg
225                 230                 235                 240

Val Phe Asn Asn Glu Arg Ala Ala Asn Ala Leu Cys Ala Gly Val Arg
                245                 250                 255

Val Thr Gly Cys Asn Thr Glu His His Cys Ile Gly Gly Gly Gly Xaa
            260                 265                 270

Phe Pro Glu Gly Ser Pro Arg Gln Cys Gly Asp Phe Xaa Ala Phe Asp
        275                 280                 285
```

```
Trp Asp Gly Tyr Gly Thr His Val Gly Tyr Ser Ser Ser Arg Glu Ile
            290                 295                 300

Thr Glu Ala Ala Val Leu Leu Phe Tyr Arg
305                 310
```

<210> SEQ ID NO 11
<211> LENGTH: 299
<212> TYPE: PRT
<213> ORGANISM: Homo sapiens

<400> SEQUENCE: 11

```
Met Asp Leu Leu Trp Ile Leu Pro Ser Leu Trp Leu Leu Leu Leu Gly
1               5                   10                  15

Gly Pro Ala Cys Leu Lys Thr Gln Glu His Pro Ser Cys Pro Gly Pro
            20                  25                  30

Arg Glu Leu Glu Ala Ser Lys Val Val Leu Leu Pro Ser Cys Pro Gly
        35                  40                  45

Ala Pro Gly Ser Pro Gly Glu Lys Gly Ala Pro Gly Pro Gln Gly Pro
    50                  55                  60

Pro Gly Pro Pro Gly Lys Met Gly Pro Lys Gly Glu Pro Gly Asp Pro
65                  70                  75                  80

Val Asn Leu Leu Arg Cys Gln Glu Gly Pro Arg Asn Cys Arg Glu Leu
                85                  90                  95

Leu Ser Gln Gly Ala Thr Leu Ser Gly Trp Tyr His Leu Cys Leu Pro
            100                 105                 110

Glu Gly Arg Ala Leu Pro Val Phe Cys Asp Met Asp Thr Glu Gly Gly
        115                 120                 125

Gly Trp Leu Val Phe Gln Arg Arg Gln Asp Gly Ser Val Asp Phe Phe
    130                 135                 140

Arg Ser Trp Ser Ser Tyr Arg Ala Gly Phe Gly Asn Gln Glu Ser Glu
145                 150                 155                 160

Phe Trp Leu Gly Asn Glu Asn Leu His Gln Leu Thr Leu Gln Gly Asn
                165                 170                 175

Trp Glu Leu Arg Val Glu Leu Glu Asp Phe Asn Gly Asn Arg Thr Phe
            180                 185                 190

Ala His Tyr Ala Thr Phe Arg Leu Leu Gly Glu Val Asp His Tyr Gln
        195                 200                 205

Leu Ala Leu Gly Lys Phe Ser Glu Gly Thr Ala Gly Asp Ser Leu Ser
    210                 215                 220

Leu His Ser Gly Arg Pro Phe Thr Thr Tyr Asp Ala Asp His Asp Ser
225                 230                 235                 240

Ser Asn Ser Asn Cys Ala Val Ile Val His Gly Ala Trp Trp Tyr Ala
                245                 250                 255

Ser Cys Tyr Arg Ser Asn Leu Asn Gly Arg Tyr Ala Val Ser Glu Ala
            260                 265                 270

Ala Ala His Lys Tyr Gly Ile Asp Trp Ala Ser Gly Arg Gly Val Gly
        275                 280                 285

His Pro Tyr Arg Arg Val Arg Met Met Leu Arg
    290                 295
```

<210> SEQ ID NO 12
<211> LENGTH: 313
<212> TYPE: PRT
<213> ORGANISM: Homo sapiens

<400> SEQUENCE: 12

Met Glu Leu Asp Arg Ala Val Gly Val Leu Gly Ala Ala Thr Leu Leu
1               5                   10                  15

Leu Ser Phe Leu Gly Met Ala Trp Ala Leu Gln Ala Ala Asp Thr Cys
            20                  25                  30

Pro Glu Val Lys Met Val Gly Leu Glu Gly Ser Asp Lys Leu Thr Ile
            35                  40                  45

Leu Arg Gly Cys Pro Gly Leu Pro Gly Ala Pro Gly Pro Lys Gly Glu
50                  55                  60

Ala Gly Thr Asn Gly Lys Arg Gly Glu Arg Gly Pro Pro Gly Pro Pro
65                  70                  75                  80

Gly Lys Ala Gly Pro Pro Gly Pro Asn Gly Ala Pro Gly Glu Pro Gln
                85                  90                  95

Pro Cys Leu Thr Gly Pro Arg Thr Cys Lys Asp Leu Leu Asp Arg Gly
            100                 105                 110

His Phe Leu Ser Gly Trp His Thr Ile Tyr Leu Pro Asp Cys Arg Pro
        115                 120                 125

Leu Thr Val Leu Cys Asp Met Asp Thr Asp Gly Gly Gly Trp Thr Val
130                 135                 140

Phe Gln Arg Arg Val Asp Gly Ser Val Asp Phe Tyr Arg Asp Trp Ala
145                 150                 155                 160

Thr Tyr Lys Gln Gly Phe Gly Ser Arg Leu Gly Glu Phe Trp Leu Gly
                165                 170                 175

Asn Asp Asn Ile His Ala Leu Thr Ala Gln Gly Thr Ser Glu Leu Arg
            180                 185                 190

Val Asp Leu Val Asp Phe Glu Asp Asn Tyr Gln Phe Ala Lys Tyr Arg
        195                 200                 205

Ser Phe Lys Val Ala Asp Glu Ala Glu Lys Tyr Asn Leu Val Leu Gly
210                 215                 220

Ala Phe Val Glu Gly Ser Ala Gly Asp Ser Leu Thr Phe His Asn Asn
225                 230                 235                 240

Gln Ser Phe Ser Thr Lys Asp Gln Asp Asn Asp Leu Asn Thr Gly Asn
                245                 250                 255

Cys Ala Val Met Phe Gln Gly Ala Trp Trp Tyr Lys Asn Cys His Val
            260                 265                 270

Ser Asn Leu Asn Gly Arg Tyr Leu Arg Gly Thr His Gly Ser Phe Ala
        275                 280                 285

Asn Gly Ile Asn Trp Lys Ser Gly Lys Gly Tyr Asn Tyr Ser Tyr Lys
290                 295                 300

Val Ser Glu Met Lys Val Arg Pro Ala
305                 310

<210> SEQ ID NO 13
<211> LENGTH: 326
<212> TYPE: PRT
<213> ORGANISM: Homo sapiens

<400> SEQUENCE: 13

Met Glu Leu Ser Gly Ala Thr Met Ala Arg Gly Leu Ala Val Leu Leu
1               5                   10                  15

Val Leu Phe Leu His Ile Lys Asn Leu Pro Ala Gln Ala Ala Asp Thr
            20                  25                  30

Cys Pro Glu Val Lys Val Val Gly Leu Glu Gly Ser Asp Lys Leu Thr
            35                  40                  45

Ile Leu Arg Gly Cys Pro Gly Leu Pro Gly Ala Pro Gly Pro Lys Gly

```
            50                  55                  60
Glu Ala Gly Val Ile Gly Glu Arg Gly Glu Arg Gly Leu Pro Gly Ala
 65                  70                  75                  80

Pro Gly Lys Ala Gly Pro Val Gly Pro Lys Gly Asp Arg Gly Glu Lys
                 85                  90                  95

Gly Met Arg Gly Glu Lys Gly Asp Ala Gly Gln Ser Gln Ser Cys Ala
                100                 105                 110

Thr Gly Pro Arg Asn Cys Lys Asp Leu Leu Asp Arg Gly Tyr Phe Leu
                115                 120                 125

Ser Gly Trp His Thr Ile Tyr Leu Pro Asp Cys Arg Pro Leu Thr Val
            130                 135                 140

Leu Cys Asp Met Asp Thr Asp Gly Gly Gly Trp Thr Val Phe Gln Arg
145                 150                 155                 160

Arg Met Asp Gly Ser Val Asp Phe Tyr Arg Asp Trp Ala Ala Tyr Lys
                165                 170                 175

Gln Gly Phe Gly Ser Gln Leu Gly Glu Phe Trp Leu Gly Asn Asp Asn
            180                 185                 190

Ile His Ala Leu Thr Ala Gln Gly Ser Ser Glu Leu Arg Val Asp Leu
        195                 200                 205

Val Asp Phe Glu Gly Asn His Gln Phe Ala Lys Tyr Lys Ser Phe Lys
210                 215                 220

Val Ala Asp Glu Ala Glu Lys Tyr Lys Leu Val Leu Gly Ala Phe Val
225                 230                 235                 240

Gly Gly Ser Ala Gly Asn Ser Leu Thr Gly His Asn Asn Phe Phe
                245                 250                 255

Ser Thr Lys Asp Gln Asp Asn Asp Val Ser Ser Asn Cys Ala Glu
                260                 265                 270

Lys Phe Gln Gly Ala Trp Trp Tyr Ala Asp Cys His Ala Ser Asn Leu
            275                 280                 285

Asn Gly Leu Tyr Leu Met Gly Pro His Glu Ser Tyr Ala Asn Gly Ile
        290                 295                 300

Asn Trp Ser Ala Ala Lys Gly Tyr Lys Tyr Ser Tyr Lys Val Ser Glu
305                 310                 315                 320

Met Lys Val Arg Pro Ala
                325

<210> SEQ ID NO 14
<211> LENGTH: 318
<212> TYPE: PRT
<213> ORGANISM: Artificial sequence
<220> FEATURE:
<223> OTHER INFORMATION: Synthetic consensus sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(16)
```

```
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(75)
<223> OTHER INFORMATION: Xaa can be any naturally occurring amino acid
<220> FEATURE:
<221> NAME/KEY: misc_feature
<222> LOCATION: (77)..(78)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (106)..(107)
<223> OTHER INFORMATION: Xaa can be any naturally occurring amino acid
<220> FEATURE:
<221> NAME/KEY: misc_feature
<222> LOCATION: (109)..(111)
<223> OTHER INFORMATION: Xaa can be any naturally occurring amino acid
<220> FEATURE:
<221> NAME/KEY: misc_feature
```

```
<222> LOCATION: (114)..(117)
<223> OTHER INFORMATION: Xaa can be any naturally occurring amino acid
<220> FEATURE:
<221> NAME/KEY: misc_feature
<222> LOCATION: (119)..(126)
<223> OTHER INFORMATION: Xaa can be any naturally occurring amino acid
<220> FEATURE:
<221> NAME/KEY: misc_feature
<222> LOCATION: (133)..(134)
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (140)..(144)
<223> OTHER INFORMATION: Xaa can be any naturally occurring amino acid
<220> FEATURE:
<221> NAME/KEY: misc_feature
<222> LOCATION: (147)..(149)
<223> OTHER INFORMATION: Xaa can be any naturally occurring amino acid
<220> FEATURE:
<221> NAME/KEY: misc_feature
<222> LOCATION: (152)..(153)
<223> OTHER INFORMATION: Xaa can be any naturally occurring amino acid
<220> FEATURE:
<221> NAME/KEY: misc_feature
<222> LOCATION: (155)..(158)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (168)..(169)
<223> OTHER INFORMATION: Xaa can be any naturally occurring amino acid
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (174)..(176)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (181)..(182)
<223> OTHER INFORMATION: Xaa can be any naturally occurring amino acid
<220> FEATURE:
<221> NAME/KEY: misc_feature
<222> LOCATION: (186)..(187)
<223> OTHER INFORMATION: Xaa can be any naturally occurring amino acid
<220> FEATURE:
<221> NAME/KEY: misc_feature
<222> LOCATION: (190)..(191)
<223> OTHER INFORMATION: Xaa can be any naturally occurring amino acid
<220> FEATURE:
<221> NAME/KEY: misc_feature
<222> LOCATION: (193)..(196)
<223> OTHER INFORMATION: Xaa can be any naturally occurring amino acid
<220> FEATURE:
<221> NAME/KEY: misc_feature
<222> LOCATION: (199)..(200)
<223> OTHER INFORMATION: Xaa can be any naturally occurring amino acid
<220> FEATURE:
```

```
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (210)..(210)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
<222> LOCATION: (224)..(224)
<223> OTHER INFORMATION: Xaa can be any naturally occurring amino acid
<220> FEATURE:
<221> NAME/KEY: misc_feature
<222> LOCATION: (230)..(230)
<223> OTHER INFORMATION: Xaa can be any naturally occurring amino acid
<220> FEATURE:
<221> NAME/KEY: misc_feature
<222> LOCATION: (237)..(237)
<223> OTHER INFORMATION: Xaa can be any naturally occurring amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (242)..(244)
<223> OTHER INFORMATION: Xaa can be any naturally occurring amino acid
<220> FEATURE:
<221> NAME/KEY: misc_feature
<222> LOCATION: (246)..(246)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid
<220> FEATURE:
<221> NAME/KEY: misc_feature
<222> LOCATION: (255)..(255)
<223> OTHER INFORMATION: Xaa can be any naturally occurring amino acid
<220> FEATURE:
<221> NAME/KEY: misc_feature
<222> LOCATION: (257)..(258)
<223> OTHER INFORMATION: Xaa can be any naturally occurring amino acid
<220> FEATURE:
<221> NAME/KEY: misc_feature
<222> LOCATION: (261)..(261)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (272)..(274)
<223> OTHER INFORMATION: Xaa can be any naturally occurring amino acid
<220> FEATURE:
<221> NAME/KEY: misc_feature
<222> LOCATION: (276)..(276)
<223> OTHER INFORMATION: Xaa can be any naturally occurring amino acid
<220> FEATURE:
<221> NAME/KEY: misc_feature
<222> LOCATION: (278)..(279)
<223> OTHER INFORMATION: Xaa can be any naturally occurring amino acid
```

```
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (283)..(284)
<223> OTHER INFORMATION: Xaa can be any naturally occurring amino acid
<220> FEATURE:
<221> NAME/KEY: misc_feature
<222> LOCATION: (287)..(287)
<223> OTHER INFORMATION: Xaa can be any naturally occurring amino acid
<220> FEATURE:
<221> NAME/KEY: misc_feature
<222> LOCATION: (289)..(290)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (313)..(313)
<223> OTHER INFORMATION: Xaa can be any naturally occurring amino acid
<220> FEATURE:
<221> NAME/KEY: misc_feature
<222> LOCATION: (316)..(316)
<223> OTHER INFORMATION: Xaa can be any naturally occurring amino acid
<220> FEATURE:
<221> NAME/KEY: misc_feature
<222> LOCATION: (318)..(318)
<223> OTHER INFORMATION: Xaa can be any naturally occurring amino acid

<400> SEQUENCE: 14

Xaa Xaa Met Leu Xaa Leu Xaa Phe Leu Leu Phe Leu Xaa Xaa Gly Xaa
1               5                   10                  15

Ala Gly Xaa Xaa Gln Ala Ala Xaa Xaa Cys Pro Glu Val Lys Xaa Trp
            20                  25                  30

Leu Glu Gly Ser Asp Lys Xaa Ser Leu Leu Arg Ser Cys Pro Xaa Ile
        35                  40                  45

Xaa Gly Xaa Xaa Gly Pro Lys Xaa Leu Asp Gly Leu Tyr Xaa Leu Arg
50                  55                  60

Xaa Leu Xaa Gly Xaa Pro Xaa Gln Xaa Xaa Xaa Asp Xaa Xaa Leu Gly
65                  70                  75                  80

Gly Gly Gly Trp Ile Leu Val Ala Ser Val His Glu Asn Xaa Met Arg
                85                  90                  95

Gly Lys Cys Leu Val Gly Xaa Arg Trp Xaa Xaa Gln Xaa Xaa Xaa Arg
            100                 105                 110

Gly Xaa Xaa Xaa Xaa Gly Xaa Xaa Xaa Xaa Xaa Xaa Xaa Xaa Leu Glu
        115                 120                 125

Gly Leu Pro Leu Xaa Xaa Leu Xaa Asp Xaa Tyr Xaa Xaa Xaa Xaa Xaa
130                 135                 140

Met Asp Xaa Xaa Xaa Gly Gly Xaa Xaa Val Xaa Xaa Xaa Xaa Asn Xaa
145                 150                 155                 160

Gly Xaa Val Asp Glu Trp Arg Xaa Xaa Ser Leu Xaa Arg Xaa Xaa Xaa
            165                 170                 175

Leu Gln Xaa Gly Xaa Xaa Trp Leu Gly Xaa Xaa Asn Leu Xaa Xaa Leu
        180                 185                 190

Xaa Xaa Xaa Xaa Pro Val Xaa Xaa Arg Val Gly Xaa Cys Asp Glu Asp
195                 200                 205

Asn Xaa Pro Xaa Leu Xaa Val Xaa Tyr Asp Ile Gly Xaa Ala Asp Xaa
```

```
            210                 215                 220
Ile Ala Ser Tyr Tyr Xaa Pro Ile Gly Glu Leu Leu Xaa Gly Ala Xaa
225                 230                 235                 240

Cys Xaa Xaa Xaa Phe Xaa Asn Glu Arg Ala Leu Ser Xaa Leu Xaa Ala
                245                 250                 255

Xaa Xaa Asp Val Xaa Gly Cys Asn Cys Xaa His His Cys Leu Gly Xaa
            260                 265                 270

Xaa Xaa Tyr Xaa Pro Xaa Ser Xaa Asn Xaa Xaa Gly Asp Xaa Ala
            275                 280                 285

Xaa Xaa Asp Trp Asp Gly Tyr Gly Leu Gly Leu Gly Trp Ser Ser Ser
            290                 295                 300

Xaa Gly Leu Leu Glu Ala Xaa Val Xaa Leu Leu Xaa Arg Xaa
305                 310                 315
```

<210> SEQ ID NO 15
<211> LENGTH: 285
<212> TYPE: PRT
<213> ORGANISM: Homo sapiens

<400> SEQUENCE: 15

```
Trp Thr Cys Ser Ser Pro Ser Leu Pro Arg Ser Cys Lys Glu Ile
1               5                   10                  15

Lys Asp Glu Cys Pro Ser Ala Phe Asp Gly Leu Tyr Phe Leu Arg Thr
                20                  25                  30

Glu Asn Gly Val Ile Tyr Gln Thr Phe Cys Asp Met Thr Ser Gly Gly
                35                  40                  45

Gly Gly Trp Thr Leu Val Ala Ser Val His Glu Asn Asp Met Arg Gly
50                  55                  60

Lys Cys Thr Val Gly Asp Arg Trp Ser Ser Gln Gln Gly Ser Lys Ala
65                  70                  75                  80

Val Tyr Pro Glu Gly Asp Gly Asn Trp Ala Asn Tyr Asn Thr Phe Gly
                85                  90                  95

Ser Ala Glu Ala Ala Thr Ser Asp Asp Tyr Lys Asn Pro Gly Tyr Tyr
                100                 105                 110

Asp Ile Gln Ala Lys Asp Leu Gly Ile Trp His Val Pro Asn Lys Ser
                115                 120                 125

Pro Met Gln His Trp Arg Asn Ser Ser Leu Leu Arg Tyr Arg Thr Asp
130                 135                 140

Thr Gly Phe Leu Gln Thr Leu Gly His Asn Leu Phe Gly Ile Tyr Gln
145                 150                 155                 160

Lys Tyr Pro Val Lys Tyr Gly Glu Gly Lys Cys Trp Thr Asp Asn Gly
                165                 170                 175

Pro Val Ile Pro Val Val Tyr Asp Phe Gly Asp Ala Gln Lys Thr Ala
                180                 185                 190

Ser Tyr Tyr Ser Pro Tyr Gly Gln Arg Glu Phe Thr Ala Gly Phe Val
                195                 200                 205

Gln Phe Arg Val Phe Asn Asn Glu Arg Ala Ala Asn Ala Leu Cys Ala
                210                 215                 220

Gly Met Arg Val Thr Gly Cys Asn Thr Glu His His Cys Ile Gly Gly
225                 230                 235                 240

Gly Gly Tyr Phe Pro Glu Ala Ser Pro Gln Gln Cys Gly Asp Phe Ser
                245                 250                 255

Gly Phe Asp Trp Ser Gly Tyr Gly Thr His Val Gly Tyr Ser Ser Ser
                260                 265                 270
```

```
Arg Glu Ile Thr Glu Ala Ala Val Leu Leu Phe Tyr Arg
        275                 280                 285
```

<210> SEQ ID NO 16
<211> LENGTH: 217
<212> TYPE: PRT
<213> ORGANISM: Homo sapiens

<400> SEQUENCE: 16

```
Pro Cys Leu Thr Gly Pro Arg Thr Cys Lys Asp Leu Leu Asp Arg Gly
1               5                   10                  15

His Phe Leu Ser Gly Trp His Thr Ile Tyr Leu Pro Asp Cys Arg Pro
            20                  25                  30

Leu Thr Val Leu Cys Asp Met Asp Thr Asp Gly Gly Gly Trp Thr Val
        35                  40                  45

Phe Gln Arg Arg Val Asp Gly Ser Val Asp Phe Tyr Arg Asp Trp Ala
    50                  55                  60

Thr Tyr Lys Gln Gly Phe Gly Ser Arg Leu Gly Glu Phe Trp Leu Gly
65                  70                  75                  80

Asn Asp Asn Ile His Ala Leu Thr Ala Gln Gly Thr Ser Glu Leu Arg
                85                  90                  95

Val Asp Leu Val Asp Phe Glu Asp Asn Tyr Gln Phe Ala Lys Tyr Arg
            100                 105                 110

Ser Phe Lys Val Ala Asp Glu Ala Glu Lys Tyr Asn Leu Val Leu Gly
        115                 120                 125

Ala Phe Val Glu Gly Ser Ala Gly Asp Ser Leu Thr Phe His Asn Asn
    130                 135                 140

Gln Ser Phe Ser Thr Lys Asp Gln Asp Asn Asp Leu Asn Thr Gly Asn
145                 150                 155                 160

Cys Ala Val Met Phe Gln Gly Ala Trp Trp Tyr Lys Asn Cys His Val
                165                 170                 175

Ser Asn Leu Asn Gly Arg Tyr Leu Arg Gly Thr His Gly Ser Phe Ala
            180                 185                 190

Asn Gly Ile Asn Trp Lys Ser Gly Lys Gly Tyr Asn Tyr Ser Tyr Lys
        195                 200                 205

Val Ser Glu Met Lys Val Arg Pro Ala
    210                 215
```

<210> SEQ ID NO 17
<211> LENGTH: 942
<212> TYPE: DNA
<213> ORGANISM: Homo sapiens

<400> SEQUENCE: 17

```
atgaaccaac tcagcttcct gctgtttctc atagcgacca ccagaggatg gagtacagat      60
gaggctaata cttacttcaa ggaatggacc tgttcttcgt ctccatctct gcccagaagc     120
tgcaaggaaa tcaaagacga atgtcctagt gcatttgatg gcctgtattt tctccgcact     180
gagaatggtg ttatctacca gaccttctgt gacatgacct tggggggtgg cggctggacc     240
ctggtggcca gcgtgcacga gaatgacatg cgtgggaagt gcacggtggg cgatcgctgg     300
tccagtcagc agggcagcaa agcagtctac ccagaggggg acggcaactg gccaactac      360 aacacctttg gatctgcaga ggcggccacg agcgatgact acaagaaccc tggctactac     420
gacatccagg ccaaggacct gggcatctgg cacgtgccaa taagtccccc catgcagcac     480
tggagaaaca gctccctgct gaggtaccgc acggacactg gcttcctcca gacactggga     540
```

-continued

```
cataatctgt ttggcatcta ccagaaatat ccagtgaaat atggagaagg aaagtgttgg    600
actgacaacg gcccggtgat ccctgtggtc tatgattttg gcgacgccca gaaaacagca    660
tcttattact caccctatgg ccagcgggaa ttcactgcgg gatttgttca gttcagggta    720
tttaataacg agagagcagc caacgccttg tgtgctggaa tgagggtcac cggatgtaac    780
actgagcacc actgcattgg tggaggagga tactttccag aggccagtcc ccagcagtgt    840
ggagattttt ctggttttga ttggagtgga tatggaactc atgttggtta cagcagcagc    900
cgtgagataa ctgaggcagc tgtgcttcta ttctatcgtt ga                       942
```

<210> SEQ ID NO 18
<211> LENGTH: 313
<212> TYPE: PRT
<213> ORGANISM: Homo sapiens

<400> SEQUENCE: 18

```
Met Asn Gln Leu Ser Phe Leu Leu Phe Leu Ile Ala Thr Thr Arg Gly
1               5                   10                  15

Trp Ser Thr Asp Glu Ala Asn Thr Tyr Phe Lys Glu Trp Thr Cys Ser
                20                  25                  30

Ser Ser Pro Ser Leu Pro Arg Ser Cys Lys Glu Ile Lys Asp Glu Cys
            35                  40                  45

Pro Ser Ala Phe Asp Gly Leu Tyr Phe Leu Arg Thr Glu Asn Gly Val
        50                  55                  60

Ile Tyr Gln Thr Phe Cys Asp Met Thr Ser Gly Gly Gly Gly Trp Thr
65                  70                  75                  80

Leu Val Ala Ser Val His Glu Asn Asp Met Arg Gly Lys Cys Thr Val
                85                  90                  95

Gly Asp Arg Trp Ser Ser Gln Gln Gly Ser Lys Ala Val Tyr Pro Glu
            100                 105                 110

Gly Asp Gly Asn Trp Ala Asn Tyr Asn Thr Phe Gly Ser Ala Glu Ala
        115                 120                 125

Ala Thr Ser Asp Asp Tyr Lys Asn Pro Gly Tyr Tyr Asp Ile Gln Ala
    130                 135                 140

Lys Asp Leu Gly Ile Trp His Val Pro Asn Lys Ser Pro Met Gln His
145                 150                 155                 160

Trp Arg Asn Ser Ser Leu Leu Arg Tyr Arg Thr Asp Thr Gly Phe Leu
                165                 170                 175

Gln Thr Leu Gly His Asn Leu Phe Gly Ile Tyr Gln Lys Tyr Pro Val
            180                 185                 190

Lys Tyr Gly Glu Gly Lys Cys Trp Thr Asp Asn Gly Pro Val Ile Pro
        195                 200                 205

Val Val Tyr Asp Phe Gly Asp Ala Gln Lys Thr Ala Ser Tyr Tyr Ser
    210                 215                 220

Pro Tyr Gly Gln Arg Glu Phe Thr Ala Gly Phe Val Gln Phe Arg Val
225                 230                 235                 240

Phe Asn Asn Glu Arg Ala Ala Asn Ala Leu Cys Ala Gly Met Arg Val
                245                 250                 255

Thr Gly Cys Asn Thr Glu His His Cys Ile Gly Gly Gly Gly Tyr Phe
            260                 265                 270

Pro Glu Ala Ser Pro Gln Gln Cys Gly Asp Phe Ser Gly Phe Asp Trp
        275                 280                 285

Ser Gly Tyr Gly Thr His Val Gly Tyr Ser Ser Ser Arg Glu Ile Thr
    290                 295                 300
```

Glu Ala Ala Val Leu Leu Phe Tyr Arg
305                 310

<210> SEQ ID NO 19
<211> LENGTH: 1114
<212> TYPE: DNA
<213> ORGANISM: Homo sapiens

<400> SEQUENCE: 19

```
gcaggggagc tccgagtgtc cacaggaagg gaactatcag ctcctggcat ctgtaaggat     60
gctgtccatg ctgaggacaa tgaccagact ctgcttcctg ttattcttct ctgtggccac    120
cagtgggtgc agtgcagcag cagcctcttc tcttgagatg ctctcgaggg aattcgaaac    180
ctgtgccttc tccttttctt ccctgcctag aagctgcaaa gaaatcaagg aacgctgcca    240
tagtgcaggt gatggcctgt attttctccg caccaagaat ggtgttgtct accagacctt    300
ctgtgacatg acttctgggg gtggcggctg gaccctggtg ccagcgtgc acgagaatga     360
catgcgtggg aagtgcacgg tgggtgatcg ctggtccagt cagcagggca acaaagcaga    420
ctacccagag ggggatggca actgggccaa ctacaacacc tttggatctg cagaggcggc    480
cacgagcgat gactacaaga accctggcta ctacgacatc caggccaagg acctgggcat    540
ctggcatgtg cccaacaagt cccccatgca gcattggaga acagcgcccc tgctgaggta    600
ccgcaccaac actggcttcc tccagagact gggacataat ctgtttggca tctaccagaa    660
atacccagtg aaatacagat cagggaaatg ttggaatgac aatggcccag ccatacctgt    720
ggtctatgac tttggtgatg ctaagaagac tgcatcttat tactcaccgt atggtcaacg    780
ggaatttgtt gcaggattcg ttcagttccg ggtgtttaat aacgagagag cagccaacgc    840
cctttgtgct gggataaaag ttactggctg taacactgag catcactgca tcggtggagg    900
agggttcttc ccacagggca aacccctgtca gtgtgggac ttctccgcct ttgactggga    960
tggatatgga actcacgtta agagcagctg cagtcgggag ataacggagg cggctgtact   1020
cttgttctat agatgagaca gagctctgcg gtgtcagggc gagaacccat cttccaaccc   1080
cggctatttg gagacggaaa aactggaatt ctaa                               1114
```

<210> SEQ ID NO 20
<211> LENGTH: 369
<212> TYPE: PRT
<213> ORGANISM: Homo sapiens

<400> SEQUENCE: 20

Gln Gly Ser Ser Glu Cys Pro Gln Glu Gly Asn Tyr Gln Leu Leu Ala
1               5                   10                  15

Ser Val Arg Met Leu Ser Met Leu Arg Thr Met Thr Arg Leu Cys Phe
                20                  25                  30

Leu Leu Phe Phe Ser Val Ala Thr Ser Gly Cys Ser Ala Ala Ala Ala
            35                  40                  45

Ser Ser Leu Glu Met Leu Ser Arg Glu Phe Glu Thr Cys Ala Phe Ser
        50                  55                  60

Phe Ser Ser Leu Pro Arg Ser Cys Lys Glu Ile Lys Glu Arg Cys His
65                  70                  75                  80

Ser Ala Gly Asp Gly Leu Tyr Phe Leu Arg Thr Lys Asn Gly Val Val
                85                  90                  95

Tyr Gln Thr Phe Cys Asp Met Thr Ser Gly Gly Gly Trp Thr Leu
                100                 105                 110

Val Ala Ser Val His Glu Asn Asp Met Arg Gly Lys Cys Thr Val Gly

```
                  115                 120                 125
Asp Arg Trp Ser Ser Gln Gln Gly Asn Lys Ala Asp Tyr Pro Glu Gly
    130                 135                 140

Asp Gly Asn Trp Ala Asn Tyr Asn Thr Phe Gly Ser Ala Glu Ala Ala
145                 150                 155                 160

Thr Ser Asp Asp Tyr Lys Asn Pro Gly Tyr Tyr Asp Ile Gln Ala Lys
                165                 170                 175

Asp Leu Gly Ile Trp His Val Pro Asn Lys Ser Pro Met Gln His Trp
            180                 185                 190

Arg Asn Ser Ala Leu Leu Arg Tyr Arg Thr Asn Thr Gly Phe Leu Gln
        195                 200                 205

Arg Leu Gly His Asn Leu Phe Gly Ile Tyr Gln Lys Tyr Pro Val Lys
    210                 215                 220

Tyr Arg Ser Gly Lys Cys Trp Asn Asp Asn Gly Pro Ala Ile Pro Val
225                 230                 235                 240

Val Tyr Asp Phe Gly Asp Ala Lys Lys Thr Ala Ser Tyr Tyr Ser Pro
                245                 250                 255

Tyr Gly Gln Arg Glu Phe Val Ala Gly Phe Val Gln Phe Arg Val Phe
            260                 265                 270

Asn Asn Glu Arg Ala Ala Asn Ala Leu Cys Ala Gly Ile Lys Val Thr
        275                 280                 285

Gly Cys Asn Thr Glu His His Cys Ile Gly Gly Gly Phe Pro
    290                 295                 300

Gln Gly Lys Pro Arg Gln Cys Gly Asp Phe Ser Ala Phe Asp Trp Asp
305                 310                 315                 320

Gly Tyr Gly Thr His Val Lys Ser Ser Cys Ser Arg Glu Ile Thr Glu
                325                 330                 335

Ala Ala Val Leu Leu Phe Tyr Arg Asp Arg Ala Leu Arg Cys Gln Gly
            340                 345                 350

Glu Asn Pro Ser Ser Asn Pro Gly Tyr Leu Glu Thr Glu Lys Leu Glu
        355                 360                 365

Phe

<210> SEQ ID NO 21
<211> LENGTH: 1149
<212> TYPE: DNA
<213> ORGANISM: Mus musculus

<400> SEQUENCE: 21
ggagcctcag cagagaaagg ttcctgccat tactcagcta gcaactctca gctcctgcct    60
ggtgcagagg gaagaccacc atgacccaac tgggattcct gctgtttatc atggttgcta   120
ccagaggttg cagtgcagct gaagagaacc tggacaccaa caggtggggc aattcttttct  180 tttcctctct gcccagaagc tgcaaggaaa tcaagcagga gcacacaaag cacaagatg    240 gtctctattt cctgcgcacg aagaatggtg tcatctacca gaccttctgt gacatgacca   300
ctgcaggtgg tggctggacc ctggtggcta gtgtgcatga gaacaacatg cgtgggaagt   360
gcactgtggg tgatcgctgg tccagtcagc aaggcaacag agctgactac ccagaggggg   420
atggcaactg ggccaactac aacacctttg gtctgcaga ggctgccaca agtgatgact    480
acaagaaccc tggctacttt gacatccagg ctgagaacct gggcatctgg cacgtgccca   540
acaaaagccc cctgcacaac tggaggaaga gctccctgct gaggtaccgc accttcactg   600
gcttcctgca gcacttggga cataatctgt ttggcctcta caagaagtac ccagtgaaat   660
```

-continued

```
acggagaagg aaagtgttgg actgacaatg cccagcatt acctgtggtc tatgactttg    720
gtgatgctcg gaagacagcc tcttattact cccctctgg ccagagggaa tttactgcag    780
gatatgttca gttcagagtg tttaataatg agagagcggc cagtgccttg tgtgctggcg    840
tgagggtcac tggatgtaat actgaacatc actgcatcgg tggaggagga ttcttcccag    900
aaggtaaccc cgtgcagtgt ggagactttg cgtcatttga ttgggatgga tatggaactc    960
acaatgggta cagcagtagc cggaagataa ctgaagcagc tgtgcttctg ttttatcgct    1020
gagaactctg cgggattggc cctgacttct ccattgtggg ctccaaggca tgagaaacac    1080
tgacttagta actggaatgc taatgagcaa taaagcagga taaatcatgt tccttgcaaa    1140
aaaaaaaaa                                                            1149
```

<210> SEQ ID NO 22
<211> LENGTH: 376
<212> TYPE: PRT
<213> ORGANISM: Mus musculus

<400> SEQUENCE: 22

```
Arg Ser Leu Ser Arg Glu Arg Phe Leu Pro Leu Leu Ser Gln Leu Ser
1               5                   10                  15

Ala Pro Ala Trp Cys Arg Gly Lys Thr Thr Met Thr Gln Leu Gly Phe
            20                  25                  30

Leu Leu Phe Ile Met Val Ala Thr Arg Gly Cys Ser Ala Ala Glu Glu
        35                  40                  45

Asn Leu Asp Thr Asn Arg Trp Gly Asn Ser Phe Phe Ser Ser Leu Pro
    50                  55                  60

Arg Ser Cys Lys Glu Ile Lys Gln Glu His Thr Lys Ala Gln Asp Gly
65                  70                  75                  80

Leu Tyr Phe Leu Arg Thr Lys Asn Gly Val Ile Tyr Gln Thr Phe Cys
                85                  90                  95

Asp Met Thr Thr Ala Gly Gly Gly Trp Thr Leu Val Ala Ser Val His
            100                 105                 110

Glu Asn Asn Met Arg Gly Lys Cys Thr Val Gly Asp Arg Trp Ser Ser
        115                 120                 125

Gln Gln Gly Asn Arg Ala Asp Tyr Pro Glu Gly Asp Gly Asn Trp Ala
    130                 135                 140

Asn Tyr Asn Thr Phe Gly Ser Ala Glu Ala Thr Ser Asp Asp Tyr
145                 150                 155                 160

Lys Asn Pro Gly Tyr Phe Asp Ile Gln Ala Glu Asn Leu Gly Ile Trp
                165                 170                 175

His Val Pro Asn Lys Ser Pro Leu His Asn Trp Arg Lys Ser Ser Leu
            180                 185                 190

Leu Arg Tyr Arg Thr Phe Thr Gly Phe Leu Gln His Leu Gly His Asn
        195                 200                 205

Leu Phe Gly Leu Tyr Lys Lys Tyr Pro Val Lys Tyr Gly Glu Gly Lys
    210                 215                 220

Cys Trp Thr Asp Asn Gly Pro Ala Leu Pro Val Val Tyr Asp Phe Gly
225                 230                 235                 240

Asp Ala Arg Lys Thr Ala Ser Tyr Tyr Ser Pro Ser Gly Gln Arg Glu
                245                 250                 255

Phe Thr Ala Gly Tyr Val Gln Phe Arg Val Phe Asn Asn Glu Arg Ala
            260                 265                 270

Ala Ser Ala Leu Cys Ala Gly Val Arg Val Thr Gly Cys Asn Thr Glu
        275                 280                 285
```

His His Cys Ile Gly Gly Gly Phe Phe Pro Glu Gly Asn Pro Val
    290                 295                 300

Gln Cys Gly Asp Phe Ala Ser Phe Asp Trp Asp Gly Tyr Gly Thr His
305                 310                 315                 320

Asn Gly Tyr Ser Ser Ser Arg Lys Ile Thr Glu Ala Ala Val Leu Leu
                325                 330                 335

Phe Tyr Arg Glu Leu Cys Gly Ile Gly Pro Asp Phe Ser Ile Val Gly
            340                 345                 350

Ser Lys Ala Glu Thr Leu Thr Leu Glu Cys Ala Ile Lys Gln Asp Lys
        355                 360                 365

Ser Cys Ser Leu Gln Lys Lys Lys
    370                 375

<210> SEQ ID NO 23
<211> LENGTH: 1136
<212> TYPE: DNA
<213> ORGANISM: Mus musculus

<400> SEQUENCE: 23
cagagaaagg ttcctgtcat tactcagcta gcaactctca gctcctgcct ggtccagagg      60
gaagaccacc atgacccaac tgggcttcct gctgtttatc atgattgcca cgagagtgtg     120
cagtgcagct gaagagaacc tggacaccaa cagatggggc aattctttct tttcctctct     180
gcccagaagc tgtaaggaaa tcaagcagga ggacacaaag gcacaagatg gtctctattt     240
cctgcgcacg gagaatggtg tcatctacca gaccttctgt gacatgacca ctgcaggtgg     300
tggctggacc ctggtggcta gtgtgcacga gaacaacctg cgtgggaggt gcactgtggg     360
tgatcgctgg tccagtcagc aaggcaacag agctgattac ccagagggga tggcaactg      420 ggccaactac aacacctttg gtctgcagag ggtgccaca agtgatgact acaagaaccc      480
tggctacttc gacatccagg cagagaacct gggcatctgg catgtgccca acaacagccc     540
cctgcacacc tggaggaaca gctccctgct gaggtaccgc accttcactg cttcctgca      600 gcgcttgggc cataatctgt ttggtctcta ccagaagtat ccggtgaaat atggagaagg     660
aaagtgttgg actgacaatg cccagcatt tcctgtggtc tatgactttg gtgatgctca      720
gaagacagcc tcttattact ctccctctgg ccggaatgaa ttcactgcag gatatgttca     780
gttcagagtg ttcaataatg agagagcagc cagtgccttg tgtgctggcg tgagggtcac     840
tggatgtaat actgaacatc actgcatcgg tggaggagga ttcttcccag aatttgaccc     900
cgaggagtgt ggagactttg ctgcatttga tgcgaatgga tatggaactc acattcggta     960
cagcaatagc cggagataa ctgaagcagc tgtgcttctg ttttatcgct gagaactctg    1020
tgggattggc cctgacttct ccaatctatg gctccaagg catgagaaac tctgacatag    1080
taacttcaat gctaatgagc aataaagcag aataaatcat gttccttgca aaaaaa       1136

<210> SEQ ID NO 24
<211> LENGTH: 374
<212> TYPE: PRT
<213> ORGANISM: Mus musculus

<400> SEQUENCE: 24

Arg Glu Arg Phe Leu Ser Leu Leu Ser Gln Leu Ser Ala Pro Ala Trp
1               5                   10                  15

Ser Arg Gly Lys Thr Thr Met Thr Gln Leu Gly Phe Leu Leu Phe Ile
            20                  25                  30

-continued

```
Met Ile Ala Thr Arg Val Cys Ser Ala Ala Glu Glu Asn Leu Asp Thr
             35                  40                  45
Asn Arg Trp Gly Asn Ser Phe Phe Ser Ser Leu Pro Arg Ser Cys Lys
 50                  55                  60
Glu Ile Lys Gln Glu Asp Thr Lys Ala Gln Asp Gly Leu Tyr Phe Leu
 65                  70                  75                  80
Arg Thr Glu Asn Gly Val Ile Tyr Gln Thr Phe Cys Asp Met Thr Thr
                 85                  90                  95
Ala Gly Gly Gly Trp Thr Leu Val Ala Ser Val His Glu Asn Asn Leu
                100                 105                 110
Arg Gly Arg Cys Thr Val Gly Asp Arg Trp Ser Ser Gln Gln Gly Asn
                115                 120                 125
Arg Ala Asp Tyr Pro Glu Gly Asp Gly Asn Trp Ala Asn Tyr Asn Thr
            130                 135                 140
Phe Gly Ser Ala Glu Gly Ala Thr Ser Asp Asp Tyr Lys Asn Pro Gly
145                 150                 155                 160
Tyr Phe Asp Ile Gln Ala Glu Asn Leu Gly Ile Trp His Val Pro Asn
                165                 170                 175
Asn Ser Pro Leu His Thr Trp Arg Asn Ser Ser Leu Leu Arg Tyr Arg
            180                 185                 190
Thr Phe Thr Gly Phe Leu Gln Arg Leu Gly His Asn Leu Phe Gly Leu
            195                 200                 205
Tyr Gln Lys Tyr Pro Val Lys Tyr Gly Glu Gly Lys Cys Trp Thr Asp
            210                 215                 220
Asn Gly Pro Ala Phe Pro Val Val Tyr Asp Phe Gly Asp Ala Gln Lys
225                 230                 235                 240
Thr Ala Ser Tyr Tyr Ser Pro Ser Gly Arg Asn Glu Phe Thr Ala Gly
            245                 250                 255
Tyr Val Gln Phe Arg Val Phe Asn Asn Glu Arg Ala Ala Ser Ala Leu
            260                 265                 270
Cys Ala Gly Val Arg Val Thr Gly Cys Asn Thr Glu His His Cys Ile
            275                 280                 285
Gly Gly Gly Gly Phe Phe Pro Glu Phe Asp Pro Glu Glu Cys Gly Asp
            290                 295                 300
Phe Ala Ala Phe Asp Ala Asn Gly Tyr Gly Thr His Ile Arg Tyr Ser
305                 310                 315                 320
Asn Ser Arg Glu Ile Thr Glu Ala Ala Val Leu Leu Phe Tyr Arg Glu
                325                 330                 335
Leu Cys Gly Ile Gly Pro Asp Phe Ser Asn Leu Trp Ala Pro Arg His
            340                 345                 350
Glu Lys Leu His Ser Asn Phe Asn Ala Asn Glu Gln Ser Arg Ile Asn
            355                 360                 365
His Val Pro Cys Lys Lys
            370
```